(12) United States Patent
Adam et al.

(10) Patent No.: US 7,129,234 B2
(45) Date of Patent: Oct. 31, 2006

(54) PHENYL HETEROCYCLYL ETHERS

(75) Inventors: Mavis D. Adam, Niantic, CT (US);
Mark D. Andrews, Sandwich (GB);
Geoffrey E. Gymer, Sandwich (GB);
David Hepworth, Sandwich (GB);
Harry R. Howard, Jr., Bristol, CT
(US); Donald S. Middleton, Sandwich
(GB); Alan Stobie, Sandwich (GB)

(73) Assignee: Pfizer Inc., New York, NY (US)

( * ) Notice: Subject to any disclaimer, the term of this patent is extended or adjusted under 35 U.S.C. 154(b) by 329 days.

(21) Appl. No.: 10/723,478

(22) Filed: Nov. 25, 2003

(65) Prior Publication Data

US 2004/0106594 A1 Jun. 3, 2004

Related U.S. Application Data

(63) Continuation of application No. 10/122,698, filed on Apr. 11, 2002, now abandoned.

(60) Provisional application No. 60/292,408, filed on May 21, 2001.

(30) Foreign Application Priority Data

Apr. 11, 2001 (GB) ................................ 0109103.2

(51) Int. Cl.
*C07D 213/65* (2006.01)
*A61K 31/44* (2006.01)
*C07D 211/62* (2006.01)
(52) U.S. Cl. .................. 514/210.2; 514/337; 514/351; 546/268.1; 546/280.1; 546/281.1; 546/300
(58) Field of Classification Search ............. 546/268.1, 546/280.1, 281.1, 300; 514/210.2, 337, 351
See application file for complete search history.

(56) References Cited

FOREIGN PATENT DOCUMENTS

| WO | WO 0050380 | 8/2000 |
| WO | WO 0076984 | 12/2000 |
| WO | WO 0127068 | 4/2001 |

OTHER PUBLICATIONS

Motofei, A binormal model of normal sexual stimulation; the etiology of premature ejaculation, Medical Hypotheses, 57(1), pp. 93-95, 2001.*
Steggall et al., ScienceDirect Abstract, 2005.*
West, Solid Solutions, Solid state chemistry and it's applications, Wiley, New York, pp. 358 and 365, 1988.*
Vippagunta et al., Crystalline solids, Advanced Drug Delivery Reviews, 48 (2001), pp. 3-26, 2001.*
Damasio, "Alzheimer's Disease and Related Dementias", Cecil Textbook of Medicine, 20th Edition, vol. 2, pp. 1992-1995 (1996).
Gainetdinov, et al., PubMed Abstract (Trends Pharmacol Sci), 23(8), pp. 367-373, Aug. 2002.
Layzer, "Degenerative Diseases of the Nervous System", Cecil Textbook of Medicine, 20th Edition, vol. 2, pp. 2050-2057 (1996).
Flatmark, et al., "Catecholamine Metabolism: An update on Key Biosynthesis Enzymes and Vesicular Monoamine Transporters", Ann. N.Y. Acad. Sci., vol. 971, pp. 69-75 (2002).

* cited by examiner

*Primary Examiner*—Deepak Rao
(74) *Attorney, Agent, or Firm*—A. Dean Olson; Martha G. Munchhof; Thomas A. Wootton

(57) ABSTRACT

The invention relates to compounds of formula I

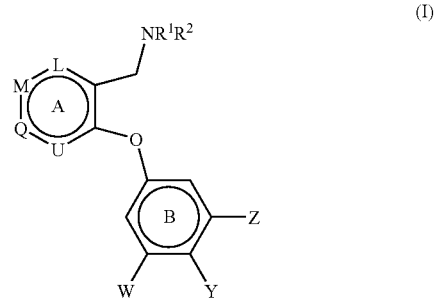

18 Claims, No Drawings

PHENYL HETEROCYCLYL ETHERS

This application is a continuation of U.S. application Ser. No. 10/122,698 which was filed on Apr. 11, 2002, now abandoned, which claims priority from United Kingdom Application No. 0109103.2 filed on Apr. 11, 2001 and U.S. Provisional Application No. 60/292,408 filed May 21, 2001.

This invention relates to novel compounds which inhibit monoamine re-uptake. In particular compounds of the present invention exhibit activity as selective serotonin re-uptake inhibitors (SSRIs) and have utility therefore in a variety of therapeutic areas. Notably the compounds of the present invention are useful in the treatment or prevention of a variety of disorders, including those in which the regulation of monoamine transporter function is implicated, such as depression, attention deficit hyperactivity disorder, obsessive-compulsive disorder, post-traumatic stress disorder, substance abuse disorders and sexual dysfunction including premature ejaculation, and to pharmaceutical formulations containing such compounds.

U.S. Pat. No. 5,190,956 discloses a class of phenoxyphenyl compounds which are a class of dopamine antagonists.

According to a first aspect the invention provides a compound of general formula (I), pharmaceutically acceptable salts, solvates or polymorphs thereof;

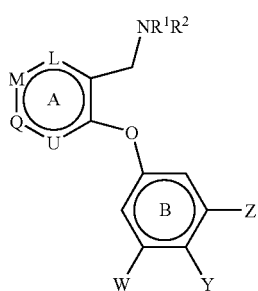

wherein;

L and U, which may be the same or different, are —N—, —N$^+$(—O$^-$)— or —C(H)—;

M and Q, which may be the same or different, are —N—, —N$^+$(—O$^-$)— or —C(R$^4$)—; wherein ring A contains 1 or 2 nitrogen atoms, and wherein when L, U, M or Q is —N$^+$(—O$^-$)—, ring A contains no other nitrogen atom;

R$^1$ and R$^2$, which may be the same or different, are hydrogen, C$_{1-6}$alkyl, (CH$_2$)$_m$(C$_{3-6}$cycloalkyl) wherein m=0, 1, 2 or 3, or R$^1$ and R$^2$ together with the nitrogen to which they are attached form an azetidine ring;

W, Y and Z, which may be the same or different, are hydrogen, halogen, C$_{1-6}$alkyl, CF$_3$, OCF$_3$, C$_{1-4}$alkylthio or C$_{1-4}$alkoxy; or Y and Z are linked so that, together with the interconnecting atoms, Y and Z form a fused 5 to 7-membered carbocyclic or heterocyclic ring which may be saturated, unsaturated or aromatic, and wherein when Y and Z form a heterocyclic ring, in addition to carbon atoms, the linkage contains one or two heteroatoms independently selected from oxygen, sulfur and nitrogen; and wherein W, Y and Z are not all hydrogen; and each R$^4$ is independently:

A-X, wherein A=—(CH$_2$)$_p$— where p is 0, 1 or 2; X is hydrogen, CONR$^6$R$^7$, SO$_2$NR$^6$R$^7$, SO$_2$NHC(=O)R$^6$, hydroxy, C$_{1-4}$alkoxy, NR$^8$SO$_2$R$^9$, NO$_2$, NR$^6$R$^{11}$, CN, CO$_2$R$^{10}$, SR$^{10}$, S(O)R$^9$ or SO$_2$R$^{10}$; R$^6$, R$^7$, R$^8$ and R$^{10}$, which may be the same or different, are hydrogen or C$_{1-6}$alkyl optionally substituted independently by one or more R$^{12}$; R$^9$ is C$_{1-6}$ alkyl optionally substituted independently by one or more R$^{12}$; R$^{11}$ is hydrogen, C$_{1-6}$alkyl optionally substituted independently by one or more R$^{12}$, C(O)R$^6$, CO$_2$R$^9$, C(O)NHR$^6$ or SO$_2$NR$^6$R$^7$; R$^{12}$ is fluoro (preferably up to 3), hydroxy, CO$_2$H, C$_{3-6}$cycloalkyl, NH$_2$, CONH$_2$, C$_{1-6}$alkoxy, C$_{1-6}$alkoxycarbonyl or a 5- or 6-membered heterocyclic ring containing 1, 2 or 3 heteroatoms selected from N, S and O optionally substituted independently by one or more R$^{13}$; or R$^6$ and R$^7$, together with the nitrogen to which they are attached, form a 4-, 5- or 6-membered heterocyclic ring optionally substituted independently by one or more R$^{13}$; or a 5- or 6-membered heterocyclic ring containing 1, 2 or 3 heteroatoms selected from N, S and O, optionally substituted independently by one or more R$^{13}$;

wherein R$^{13}$ is hydroxy, C$_1$–C$_4$alkoxy, fluoro, C$_1$–C$_6$alkyl, haloalkyl, haloalkoxy, —NH$_2$, —NH(C$_1$–C$_6$alkyl) or —N(C$_1$–C$_6$alkyl)$_2$; or when both M and Q are CR$^4$, the R$^4$ groups are linked so that together with the interconnecting atoms, the R$^4$ groups form a fused 5- to 7-membered carbocyclic or heterocyclic ring which may be saturated, unsaturated or aromatic (preferably the linkage is —(CH)$_4$—).

Unless otherwise indicated, any alkyl group may be straight or branched and is of 1 to 6 carbon atoms, preferably 1 to 4 and particularly 1 to 3 carbon atoms.

Unless otherwise indicated, any heterocyclyl group contains 5 to 7 ring-atoms up to 4 of which may be hetero-atoms such as nitrogen, oxygen and sulfur, and may be saturated, unsaturated or aromatic. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl.

The term heterocyclic should be similarly construed.

Unless otherwise indicated, any carbocyclyl group contains 3 to 8 ring-atoms, and may be saturated, unsaturated or aromatic. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocyclic should be similarly construed. In addition, the term carbocyclyl includes any fused combination of carbocyclyl groups, for example naphthyl, phenanthryl, indanyl and indenyl.

Preferably only one of L, U, M and Q is —N— or —N$^+$(—O$^-$)—. More preferably L is —C(H)—.

Preferably R$^1$ and R$^2$, which may be the same or different, are hydrogen or C$_1$–C$_6$alkyl (preferably methyl) or R$^1$ and R$^2$, together with the nitrogen to which they are attached, form an azetidine ring. More preferably, R$^1$ is methyl and R$^2$ is hydrogen or methyl, or R$^1$ and R$^2$, together with the nitrogen to which they are attached, form an azetidine ring. More preferably still $R^1$ is methyl and $R^2$ is hydrogen or methyl.

Preferably W is hydrogen, $C_{1-6}$alkyl (preferably methyl or ethyl), $C_{1-4}$alkoxy (preferably methoxy or ethoxy) or halogen (preferably chloro, fluoro or bromo) and Y and Z are as defined in the first aspect.

More preferably W is hydrogen, methyl or ethyl; and Y and Z, which may be the same or different, are hydrogen, methyl, ethyl, $CF_3$, $OCF_3$, methylthio, ethylthio, methoxy, ethoxy, chloro, fluoro or bromo; or Y and Z are linked so that, together with the interconnecting atoms, Y and Z form a fused 5 to 7-membered carbocyclic or heterocyclic ring which may be saturated, unsaturated or aromatic, and wherein when Y and Z form a heterocyclic ring, in addition to carbon atoms, the linkage contains one or two heteroatoms independently selected from oxygen, sulfur and nitrogen; wherein W, Y and Z are not all hydrogen.

More preferably still W is hydrogen; and Y and Z, which may be the same or different, are hydrogen, fluoro, chloro, methyl, ethyl, methylthio, ethylthio, methoxy or ethoxy; or Y and Z are linked so that, together with the interconnecting atoms, Z and Y form a fused 5 to 7-membered heterocyclic ring containing one or more sulfur atoms; wherein Y and Z are not both hydrogen.

When Y and Z are linked so that, together with the interconnecting atoms, Z and Y form a fused 5 to 7-membered heterocyclic ring containing one or more sulfur atoms, preferred linkages forming the fused ring are —S(CH$_2$)$_2$—, —CH$_2$S—CH$_2$— or —S(CH$_2$)$_2$O— wherein either end of these linkages corresponds to either group Y or Z.

Preferably when present each $R^4$ is independently —(CH$_2$)$_p$—X, where p is 0, 1 or 2 (preferably 0 or 1); X is hydrogen, CONR$^6$R$^7$, SO$_2$NR$^6$R$^7$, SO$_2$NH(C=O)R$^6$, hydroxy, $C_{1-4}$alkoxy, NR$^8$SO$_2$R$^9$, NO$_2$, NR$^6$R$^{11}$, CN, CO$_2$R$^{10}$, SR$^{10}$, S(O)R$^9$ or SO$_2$R$^{10}$; wherein R$^6$, R$^7$, R$^8$, R$^{10}$ or R$^{11}$, which may be the same or different, are hydrogen or $C_{1-6}$alkyl (preferably methyl or ethyl); and R$^9$ is $C_{1-6}$alkyl (preferably methyl or ethyl).

More preferably when present each $R^4$ is independently —(CH$_2$)$_p$—X, where p is 0 or 1; X is hydrogen, CONR$^6$R$^7$, SO$_2$NR$^6$R$^7$, NR$^8$SO$_2$R$^9$, hydroxy or NR$^6$R$^{11}$; wherein R$^6$, R$^7$, R$^8$, or R$^{11}$, which may be the same or different, are hydrogen or $C_{1-6}$alkyl (preferably methyl or ethyl); and R$^9$ is $C_{1-6}$alkyl (preferably methyl or ethyl). More preferably still, each $R^4$ is hydrogen or methyl.

Preferably
only one of L, U, M and Q is —N— or —N$^+$(—O$^-$)—;
$R^1$ and $R^2$, which may be the same or different, are hydrogen or $C_1$–$C_6$alkyl; or $R^1$ and $R^2$, together with the nitrogen to which they are attached, form an azetidine ring;
W is hydrogen, $C_{1-6}$alkyl (preferably methyl or ethyl), $C_{1-4}$alkoxy (preferably methoxy or ethoxy) or halogen (preferably chloro, fluoro or bromo) and Y and Z are as defined in the first aspect; and
when present each $R^4$ is independently —(CH$_2$)$_p$—X, where p is 0, 1 or 2 (preferably 0 or 1); X is hydrogen, CONR$^6$R$^7$, SO$_2$NR$^6$R$^7$, SO$_2$NH(C=O)R$^6$, hydroxy, $C_{1-4}$alkoxy, NR$^8$SO$_2$R$^9$, NO$_2$, NR$^6$R$^{11}$, CN, CO$_2$R$^{10}$, SR$^{10}$, S(O)R$^9$ or SO$_2$R$^{10}$; wherein R$^6$, R$^7$ R$^8$, R$^{10}$ or R$^{11}$ which may be the same or different, are hydrogen or $C_{1-6}$alkyl (preferably methyl or ethyl); and R$^9$ is $C_{1-6}$alkyl (preferably methyl or ethyl).

More preferably
L is —C(H)—;
U is —C(H)— or —N—;
M and Q, which may be the same or different, are —N— or —C(R$^4$)—;
$R^1$ is methyl;
$R^2$ is hydrogen or methyl;
W is hydrogen;
Y and Z, which may be the same or different, are hydrogen, fluoro, chloro, methyl, ethyl, methylthio, methoxy or ethyl; or Y and Z are linked so that, together with the interconnecting atoms, Z and Y form a fused 5 to 7-membered heterocyclic ring containing one or more sulfur atoms (preferred linkages are —S(CH$_2$)$_2$—, —CH$_2$S—CH$_2$— or —S(CH$_2$)$_2$O— wherein either end of these linkages corresponds to either group Y or Z); and
each $R^4$ is independently —(CH$_2$)$_p$—X, where p is 0 or 1; X is hydrogen, CONR$^6$R$^7$, SO$_2$NR$^6$R$^7$, NR$^8$SO$_2$R$^9$, hydroxy or NR$^6$R$^{11}$; wherein R$^6$, R$^7$, R$^8$, or R$^{11}$, which may be the same or different, are hydrogen or $C_{1-6}$alkyl (preferably methyl or ethyl); and R$^9$ is $C_{1-6}$alkyl (preferably methyl or ethyl) (preferably each $R^4$ is hydrogen or methyl).

Preferred compounds are:
N-methyl-N-({4-[4-(methylsulfanyl)phenoxy]-3-pyridinyl}methyl)amine,
N-{[4-(2,3-dihydro-1-benzothien-5-yloxy)-3-pyridinyl]methyl}-N-methylamine,
N-({4-[3-chloro-4-(methylsulfanyl)phenoxy]-3-pyridinyl}methyl)-N-methylamine,
N-methyl-N-({3-[4-(methylsulfanyl)phenoxy]-4-pyridinyl}methyl)amine,
N-methyl-N-({3-[3-methyl-4-(methylsulfanyl)phenoxy]-4-pyridinyl}methyl)amine,
N-{[4-(2,3-Dihydro-1,4-benzoxathiin-7-yloxy)-6-methyl-3-pyridinyl]methyl}-N-methylamine,
N-methyl-N-({6-methyl-4-[3-methyl-4-(methylsulfanyl)phenoxy]-3-pyridinyl}methyl)amine,
N-({4-[3-chloro-4-(methylsulfanyl)phenoxy]-3-pyridinyl}methyl)-N,N-dimethylamine,
N-({4-[3-fluoro-4-(methylsulfanyl)phenoxy]-3-pyridinyl}methyl)-N,N-dimethylamine,
N,N-dimethyl-N-({3-[4-(methylsulfanyl)phenoxy]-4-pyridinyl}methyl)amine,
N-{[4-(2,3-dihydro-1-benzothien-5-yloxy)-3-pyridinyl]methyl}-N,N-dimethylamine,
N-({4-[3-Methoxy-4-(methylsulfanyl)phenoxy]-3-pyridinyl}methyl)-N,N-dimethylamine,
N,N-dimethyl-N-({4-[4-(trifluoromethyl)phenoxy]-3-pyridinyl}methyl)amine,
N,N-dimethyl-N-({4-[4-(methylsulfanyl)phenoxy]-3-pyridinyl}methyl)amine, and
N,N-dimethyl-N-({4-[3-methyl-4-(methylsulfanyl)phenoxy]-3-pyridinyl}methyl)amine.

For the avoidance of doubt, unless otherwise indicated, the term substituted means substituted by one or more defined groups. In the case where groups may be selected from a number of alternatives groups, the selected groups may be the same or different. For the avoidance of doubt, the term independently means that where more than one substituent is selected from a number of possible substituents, those substituents may be the same or different.

The pharmaceutically or veterinarily acceptable salts of the compounds of formula I include suitable acid addition salts, which are formed from acids which form non-toxic salts and examples are the hydrochloride/chloride, hydrobromide/bromide, hydroiodide/iodide, sulphate, bisulphate, nitrate, phosphate, hydrogen phosphate, acetate, fumarate, pamoate, aspartate, besylate, bicarbonate/carbonate, camsylate, D and L-lactate, D and L-tartrate, edisylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate and pamoate salts.

Suitable base salts are formed from bases which form non-toxic salts and examples are the sodium, potassium, aluminium, calcium, magnesium, zinc, choline, diolamine, olamine, arginine, glycine, tromethamine, benzathine, lysine, meglumine and diethylamine salts. For reviews on suitable pharmaceutical salts see Berge et al, J. Pharm, Sci., 66, 1–19, 1977; Bighley et al, International Journal of Pharmaceutics, 33 (1986), 201–217; and P L Gould, Encyclopedia of Pharmaceutical Technology, Marcel Debker Inc, New York 1996, Volume 13, page 453–497.

The pharmaceutically acceptable solvates of the compounds of the invention include the hydrates thereof.

Also included within the scope of the compound and various salts of the invention are polymorphs thereof.

Hereinafter, compounds their pharmaceutically acceptable salts, their solvates or polymorphs, defined in any aspect of the invention (except intermediate compounds in chemical processes) are referred to as "compounds of the invention".

The compounds of the invention have the advantage that they are selective inhibitors of the re-uptake of serotonin (SRIs) (and so are likely to have reduced side effects), they have a rapid onset of action (making them suitable for administration shortly before an effect is required), they have desirable potency and associated properties. Compounds that selectively inhibit the re-uptake of serotonin, but not noradrenaline or dopamine, are preferred.

The compounds of the invention may possess one or more chiral centres and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

The compounds of the invention may exist in one or more tautomeric forms. All tautomers and mixtures thereof are included in the scope of the present invention. For example, a claim to 2-hydroxypyridinyl would also cover its tautomeric form, α-pyridonyl.

The invention also includes radiolabelled compounds.

It will be appreciated by those skilled in the art that certain protected derivatives of compounds of the invention, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention.

All protected derivatives and prodrugs of compounds of the invention are included within the scope of the invention. Examples of suitable pro-drugs for the compounds of the present invention are described in Drugs of Today, Volume 19, Number 9, 1983, pp 499–538 and in Topics in Chemistry, Chapter 31, pp 306–316 and in "Design of Prodrugs" by H. Bundgaard, Elsevier, 1985, Chapter 1 (the disclosures in which documents are incorporated herein by reference).

It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Compounds of the invention may be prepared, in known manner in a variety of ways. In the following reaction schemes and hereafter, unless otherwise stated $R^1$ to $R^{13}$, L, U, M, Q, W, Y and Z are as defined in the first aspect. These processes form further aspects of the invention.

Throughout the specification, general formulae are designated by Roman numerals I, II, III, IV etc. Subsets of these general formulae are defined as Ia, Ib, Ic etc, . . . IVa, IVb, IVc etc.

Compounds of general formula I may be prepared from compounds of general formula II by a variety of methods (see Scheme 1)

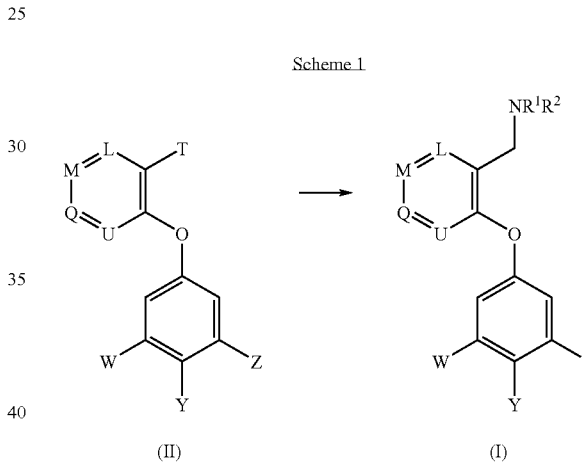

Scheme 1 i) Compounds of general formula I may be prepared from compounds of general formula II where T is —CHO, by reaction with an amine of formula $HNR^1R^2$ (or a salt thereof), followed by reduction with a hydride reducing agent in a suitable solvent. When either $R^1$ or $R^2$ is hydrogen, suitable solvents include protic solvents such as ethanol, and sodium borohydride is an appropriate reducing agent as exemplified by Examples 18 to 33 and 56 to 57 herein. When neither $R^1$ or $R^2$ are hydrogen, tetrahydrofuran/dichloromethane is a suitable solvent system and sodium triacetoxyborohydride is a suitable reducing agent. In such reactions the use of a salt form of $HNR^1R^2$, such as the hydrochloride or acetate is preferable, and an auxiliary base, to aid solubility of the $HNR^1R^2$ salt, such as triethylamine may optionally be added along with acetic acid, as exemplified by Examples 94 to 99 and 101 herein.

ii) Compounds of general formula I may be prepared from compounds of general formula II where T is —$CO_2R^{10}$ and $R^{10}$=methyl or ethyl, by reaction with an amine of general formula $NHR^1R^2$ to form an amide, followed by reduction to provide an amine.

iii) Compounds of general formula I may be prepared from compounds of general formula II where T is cyano, by reduction to its corresponding amine of formula —$CH_2NH_2$, using hydride reducing agents such as $BH_3$.THF or lithium aluminium hydride (as exemplified by Examples 1 to 16) or by hydrogenation with a suitable metal catalyst for example Raney Nickel (see Example 17).

iv) Compounds of general formula I may be prepared from compounds of general formula II where T is —C(O)$NR^1R^2$, by reduction to provide an amine, for example with a hydride reducing agent such as $BH_3$.THF or lithium aluminium hydride (see Examples 38 and 48 to 54).

Alternatively, compounds of general formula I having a particular $NR^1R^2$ group may be converted into other compounds of general formula I having a different $NR^1R^2$ group. For example:

i) Compounds of formula I wherein either $R^1$ or $R^2$ is hydrogen, can be converted into a compound of formula I wherein neither $R^1$ nor $R^2$ is hydrogen, by reaction with an aldehyde and a hydride reducing agent. Suitable aldehydes include formaldehyde, suitable reducing agents include sodium tri(acetoxy)borohydride and the reaction is preferably conducted in a solvent which does not interfere with the reaction, such as dichloromethane at or below room temperature, as exemplified by Examples 59 to 93 and the method described for Example 58.

ii) Compounds of formula I wherein $R^1$ or $R^2$ is hydrogen, can be converted into a compound of formula I wherein $R^1$ or $R^2$ is methyl, by reaction with a formylating agent, for example pentafluorophenyl formate, in a suitable solvent, followed by subsequent reduction of the intermediate N-formyl compound with a hydride reducing agent such as $BH_3$.THF or lithium aluminium hydride in an inert solvent, preferably at elevated temperature. Suitable formylating agents include pentafluorophenyl formate (formed from formic acid, pentafluorophenol and dicyclohexylcarbodiimide) and suitable solvents for the formylation include dichloromethane. Suitable reducing agents include borane-tetrahydrofuran complex and suitable inert solvents for the reduction include tetrahydrofuran as exemplified by Examples 34 to 47 and 55 herein.

Compounds of formula I where M or 0 is —$C(R^4)$— may be prepared from the corresponding halo compound by a variety of methods:

i) Compounds of formula I where M or Q is —C(CN)— may be prepared by reaction of the corresponding halo compound with a cyanide salt in the presence of a Pd(0) or (II)catalyst in a high boiling solvent at elevated temperatures. Suitable Pd catalysts include palladium tetrakis (triphenylphosphine), suitable cyanide salts include $Zn(CN)_2$ and suitable high boiling solvents which do not adversely affect the reaction include dimethylformamide.

ii) Compounds of formula I where M or Q is —$C(CO_2R)$— may be prepared by reacting the corresponding halo compound with carbon monoxide at high pressure with a Pd(0) or (II) catalyst, in an alcohol solvent (ROH wherein R is $C_1$–$C_4$ alkyl), in the presence of a base at elevated temperatures. For example the reaction may be carried out at pressures in the region of about 100 to 200 p.s.i, whilst suitable Pd catalysts include dichloro[1-1'-bis(diphenylphosphino)ferrocene]-palladium (II) chloride dichloromethane adduct, suitable bases include triethylamine and suitable alcohol solvents include methanol as exemplified by Example 107 herein.

Alternatively compounds of formula I where M or Q is —$C(R^4)$— may be prepared from the corresponding compound of formula I where M or Q is —$C(R^4)$— by a variety of methods.

i) Compounds of formula I where M or Q is —$C(NH_2)$— may be prepared from the corresponding compounds of formula I where M or Q is —$C(NO_2)$— by treatment with a reducing agent in a protic solvent at, or above, room temperature. Suitable reducing agents include iron powder/calcium chloride, suitable protic solvents include aqueous ethanol or acetic acid.

ii) Compounds of formula I where M or Q is —$C(NHSO_2R^9)$— may be prepared from the corresponding compounds of formula I where M or Q is —$C(NH_2)$— by reaction with a sulfonylating agent in the presence of a base in an inert solvent which does not adversely affect the reaction at, or below, room temperature. Suitable sulfonylating agents include methanesulfonyl chloride, suitable bases include triethylamine and suitable inert solvents include dichloromethane.

iii) Compounds of formula I where M or Q is —$C(NR^8SO_2R^9)$— may be prepared from the corresponding compounds of formula I where M or Q is —$C(NHSO_2R^9)$—, by treatment with an alkylating agent and a base in a suitable inert solvent. Examples of suitable alkylating agents include methyl iodide, suitable bases include potassium carbonate and suitable inert solvents include acetonitrile.

iv) Compounds of formula I where M or Q is —C(C(=O)$NH_2$)— may be prepared from the corresponding compounds of formula I where M or Q is —C(CN)—, by hydrolysis under basic, oxidative or acid conditions. Basic hydrolysis is preferably conducted with a hydroxide salt such as potassium hydroxide in a protic solvent such as t-butanol at elevated temperatures.

v) Compounds of formula I where M or Q is —$C(CH_2OH)$— may be prepared from the corresponding compounds of formula I where M or Q is —$C(CO_2R^{10})$—, by treatment with a hydride reducing agent, such as lithium aluminium hydride.

vi) Compounds of formula I where M or Q is —$C(CO_2H)$— may be prepared from the corresponding compounds of formula I where M or Q is —$C(CO_2R^9)$—, by treatment with a suitable hydroxide salt in the presence of water and a suitable co-solvent. Suitable hydroxide salts include lithium hydroxide and suitable co-solvents include methanol as exemplified by the method for Example 108 herein.

vii) Compounds of formula I where M or Q is —$C(CONR^6R^7)$— may be prepared from the corresponding compounds of formula I where M or Q is —$C(CO_2H)$—, by treatment with a coupling agent, a base and an amine $HNR^6R^7$ in a suitable inert solvent which does not adversely affect the reaction. Suitable coupling agents include 1-(3-dimethylaminopropyl)-3-ethylcarbodiimide hydrochloride in the presence of 1-hydroxybenzotriazole, suitable bases include N,N-diisopropylethylamine and suitable solvents include dichloromethane as exemplified by Example 108 herein.

viii) Compounds of formula I where M or Q is —$C(CO_2H)$— may be prepared from the corresponding compounds of formula I where M or Q is —C(Me)—, by treatment with a suitable oxidising agent in a suitable solvent which does not adversely affect the reaction.

Compounds of formula II may be prepared in turn from the coupling of compounds of general formula IV with compounds of general formula III, wherein LG is a suitable leaving group such as halogen (F, Cl, Br or I) or a sulfonate ester such as trifluoromethanesulfonate or methanesulfonate (preferably LG is F or Cl) (See Scheme 2). Such coupling reaction may be accomplished by techniques known in the art, such as via reaction with potassium carbonate in a suitable solvent such as dimethylformamide under appropriate reaction conditions such as elevated temperature and in an inert atmosphere (see Preparations 18 to 63). This process forms a further aspect of the invention.

Scheme 2

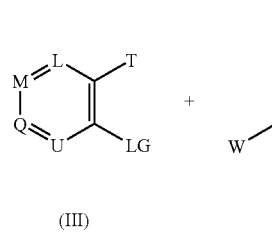

(III)        (IV)

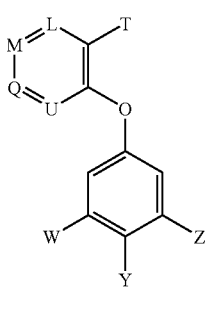

(II)

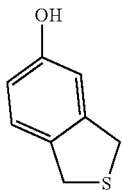
(IVa)

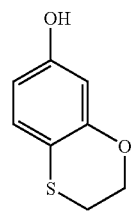
(IVb)

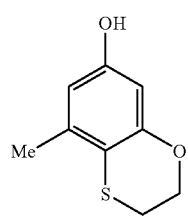
(IVc)

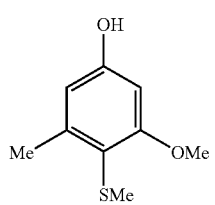
(IVd)

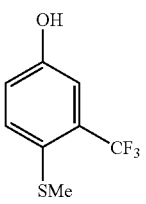
(IVe)

Alternatively compounds of formula II where T is —CONR$^1$R$^2$ may be prepared from the corresponding compounds of formula II where T is —CO$_2$H, by treatment with a coupling agent and an amine HNR$^1$R$^2$ in a suitable inert solvent which does not adversely affect the reaction. Suitable coupling agents include carbonyldiimidazole, suitable amines include methylamine and suitable solvents include tetrahydrofuran as exemplified by Preparation 64 herein. Compounds of formula II where T is —CO$_2$H may themselves be formed from compounds of formula II where T is —CN by treatment with a suitable hydroxide salt in the presence of water and a suitable co-solvent at an appropriate temperature. Suitable hydroxide salts include sodium hydroxide and suitable co-solvents include ethanol as exemplified by Preparation 64 herein.

Many compounds of formula IV are either known and available from commercial sources or are available from commercially available materials using known techniques (see Examples hereinafter). However some compounds of formula IV are novel. According to a further aspect, the invention provides the following compounds of general formula IV:

Compounds of formula III are either known and available from commercial sources or are available from commercially available materials using known techniques (see Examples hereinafter). In particular compounds of formula III where M or Q are —C(R$^4$)— may be prepared from the corresponding halo compound, in analogous fashion to the methods described above to prepare compounds of formula I. Alternatively compounds of formula III where M or Q are —C(R$^4$)— may be prepared from the corresponding compound of formula III, in analogous fashion to the methods described above to prepare compounds of formula I.

The skilled person will appreciate that in appropriate cases introduction/elaboration of R$^4$ can be performed prior to conversion of T to —CH$_2$NR$^1$R$^2$.

Further, the skilled person will appreciate that the ether coupling (see Scheme 2) may be performed after conversion of the group T to the group —CH$_2$NR$^1$R$^2$.

The skilled chemist will appreciate that diaryl ethers may be prepared using a number of synthetic methodologies. For a review of methodologies see J S Sawyer, *Tetrahedron,* 56 (2000) 5045–5065, incorporated herein by reference. In particular, compounds of general formula II may be prepared from compounds V and VI, wherein LG is a suitable leaving group such as halogen (F, Cl, Br or I) or a sulfonate ester such as trifluoromethanesulfonate or methanesulfonate (preferably LG is F or Cl) (see Scheme 3). Suitable reaction conditions are similar to those described above for the coupling reaction shown in Scheme 2, optionally in the presence of a suitable metal catalyst.

Scheme 3

(V) + (VI) →

(II)

Compounds of formulae V and VI are either known and available from commercial sources or are available from commercially available materials using known techniques (see Examples hereinafter).

It will be apparent to those skilled in the art that sensitive functional groups may need to be protected and deprotected during synthesis of a compound of formula I. This may be achieved by conventional techniques, for example as described in 'Protective Groups in Organic Synthesis', 3rd edition, by T W Greene and P G M Wuts, John Wiley and Sons Inc, 1999.

The compounds of the invention are useful because they have pharmacological activity in mammals, including humans. More particularly, they are useful in the treatment or prevention of a disorder in which the regulation of monoamine transporter function is implicated. Disease states that may be mentioned include hypertension, depression (e.g. depression in cancer patients, depression in Parkinson's patients, postmyocardial infarction depression, subsyndromal symptomatic depression, depression in infertile women, paediatric depression, major depression, single episode depression, recurrent depression, child abuse induced depression, post partum depression and grumpy old man syndrome), generalized anxiety disorder, phobias (e.g. agoraphobia, social phobia and simple phobias), posttraumatic stress syndrome, avoidant personality disorder, premature ejaculation, eating disorders (e.g. anorexia nervosa and bulimia nervosa), obesity, chemical dependencies (e.g. addictions to alcohol, cocaine, heroin, phenobarbital, nicotine and benzodiazepines), cluster headache, migraine, pain, Alzheimer's disease, obsessive-compulsive disorder, panic disorder, memory disorders (e.g. dementia, amnestic disorders, and age-related cognitive decline (ARCD)), Parkinson's diseases (e.g. dementia in Parkinson's disease, neuroleptic-induced parkinsonism and tardive dyskinesias), endocrine disorders (e.g. hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania, headache (associated with vascular disorders), emotional lability, pathological crying, sleeping disorder (cataplexy) and shock.

Disorders of particular interest include depression, attention deficit hyperactivity disorder, obsessive-compulsive disorder, post-traumatic stress disorder, substance abuse disorders and sexual dysfunction including (in particular) premature ejaculation. Premature ejaculation may be defined as persistent or recurrent ejaculation before, upon or shortly after penile penetration of a sexual partner. It may also be defined as ejaculation occurring before the individual wishes [see 'The Merck Manual', 16$^{th}$ edition, p 1576, published by Merck Research Laboratories, 1992].

Thus, according to further aspects, the invention provides:

i) A compound of formula (I), as defined in the first aspect, pharmaceutically acceptable salts, solvates or polymorphs thereof, for use as a medicament.

ii) The use of a compound of formula (I), as defined in the first aspect, pharmaceutically acceptable salts, solvates or polymorphs thereof, in the preparation of a medicament for the treatment or prevention of a disorder in which the regulation of monoamine transporter function is implicated, for example hypertension, depression, generalized anxiety disorder, phobias, posttraumatic stress syndrome, avoidant personality disorder, premature ejaculation, eating disorders, obesity, chemical dependencies, cluster headache, migraine, pain, Alzheimer's disease, obsessive-compulsive disorder, panic disorder, memory disorders, Parkinson's diseases, endocrine disorders, vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania, headache (associated with vascular disorders), emotional lability, pathological crying, sleeping disorder (cataplexy) and shock.

iii) The use of a compound of formula (I), as defined in the first aspect, pharmaceutically acceptable salts, solvates or polymorphs thereof, in the preparation of a medicament for the treatment or prevention of a disorder in which the regulation of monoamine transporter function is implicated where that disorder is depression, attention deficit hyperactivity disorder, obsessive-compulsive disorder, post-traumatic stress disorder, substance abuse disorders or sexual dysfunction.

iv)

iii) The use of a compound of general formula (I) as defined in the first aspect, pharmaceutically acceptable salts, solvates or polymorphs thereof, in the manufacture of a medicament for the treatment or prevention of premature ejaculation, and also provides a method of treatment or prevention of premature ejaculation comprising the administration of this compound to a patient in need of such treatment or prevention.

iv) A method of treatment or prevention of depression, attention deficit hyperactivity disorder, obsessive-compulsive disorder, post-traumatic stress disorder, substance abuse disorders or sexual dysfunction including premature ejaculation, which comprises administering a therapeutically effective amount of a compound of formula (I) as defined in the first aspect, pharmaceutically acceptable salts, solvates or polymorphs thereof, to a patient in need of such treatment or prevention.

v) A method of increasing ejaculatory latency which comprises the administration of an effective amount of a compound of formula (I) as defined in the first aspect, pharmaceutically acceptable salts, solvates or polymorphs thereof, to a male desiring increased ejaculatory latency.

vi) A compound of formula (I) as defined in the first aspect, pharmaceutically acceptable salts, solvates or polymorphs thereof, for the treatment or prevention of a disorder in which the regulation of monoamine transporter function is implicated, for example depression, attention deficit hyperactivity disorder, obsessive-compulsive disorder, post-traumatic stress disorder, substance abuse disorders or sexual dysfunction including premature ejaculation.

It is to be appreciated that all references herein to treatment include curative, palliative and prophylactic treatment.

The compounds of the invention may be administered alone or as part of a combination therapy. If a combination of active agents are administered, then they may be administered simultaneously, separately or sequentially. In particular, the compounds of the invention may be combined with the following for the treatment of PE:

Alpha-blockers (e.g. phentolamine, doxazasim, tansulosin, terazasin, prazasin and Example 19 of WO9830560;

Apomorphine—teachings on the use of apomorphine as a pharmaceutical may be found in U.S. Pat. No. 5,945,117;

Dopamine D2 agonists (e.g. Premiprixal, Pharmacia Upjohn compound number PNU95666);

Melanocortin receptor agonists (e.g. Melanotan II);

PGE1 receptor agonists (e.g. alprostadil);

Mono amine transport inhibitors, particularly Noradrenaline Re-uptake Inhibitors (NRIs) (e.g. Reboxetine), other Serotonin Re-uptake Inhibitors (SRI) (e.g. paroxetine) or Dopamine Re-uptake Inhibitors (DRIs);

5-HT$_{1A}$ antagonists (e.g. robalzotan)

PDE inhibitors such as PDE2 (e.g. erythro-9-(2-hydroxyl-3-nonyl)-adenine) and Example 100 of EP 0771799-incorporated herein by reference) and in particular a PDE5 inhibitor (e.g. sildenafil, 1-{[3-(3,4-dihydro-5-methyl-4-oxo-7-propylimidazo[5,1-f]-as-trazin-2-yl)-4-ethoxyphenyl]sulfonyl}-4-ethylpiperazine i.e. vardenafil/ Bayer BA 38-9456 or IC351 (see structure below, Icos Lilly)).

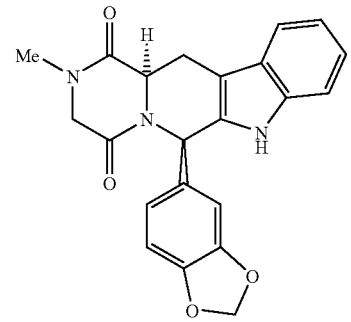

IC351 (Icos Lilly)

For human use the compounds of the invention can be administered alone but in human therapy will generally be administered in admixture with a suitable pharmaceutical excipient, diluent or carrier selected with regard to the intended route of administration and standard pharmaceutical practice. Accordingly the present invention provides for a composition comprising a compound of formula (I) as disclosed herein, or pharmaceutically acceptable salts, solvates or polymorphs thereof, and a pharmaceutically acceptable diluent or carrier.

For example, the compounds of the invention, can be administered orally, buccally or sublingually in the form of tablets, capsules (including soft gel capsules), ovules, elixirs, solutions or suspensions, which may contain flavouring or colouring agents, for immediate-, delayed-, modified-, sustained-, dual-, controlled-release or pulsatile delivery applications. The compounds of the invention may also be administered via intracavernosal injection. The compounds of the invention may also be administered via fast dispersing or fast dissolving dosage forms.

Such tablets may contain excipients such as microcrystalline cellulose, lactose, sodium citrate, calcium carbonate, dibasic calcium phosphate, glycine, and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention, and their pharmaceutically acceptable salts, may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

The following dosage levels and other dosage levels herein are for the average human subject having a weight range of about 65 to 70 kg. The skilled person will readily be able to determine the dosage levels required for a subject whose weight falls outside this range, such as children and the elderly.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including PE), compounds of the invention may be taken as a single dose on an "as required" basis (i.e. as needed or desired).

Example Tablet Formulation

In general a tablet formulation could typically contain between about 0.01 mg and 500 mg of a compound according to the present invention (or a salt thereof) whilst tablet fill weights may range from 50 mg to 1000 mg. An example formulation for a 10 mg tablet is illustrated:

| Ingredient | % w/w |
| --- | --- |
| Free acid, Free base or Salt of Compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

The compounds of the invention can also be administered intranasally or by inhalation and are conveniently delivered in the form of a dry powder inhaler or an aerosol spray presentation from a pressurised container, pump, spray or nebulizer with the use of a suitable propellant, e.g. dichlorodifluoromethane, trichlorofluoromethane, dichlorotetrafluoro-ethane, a hydrofluoroalkane such as 1, 1, 1,2-tetrafluoroethane (HFA 134A [trade mark]) or 1, 1, 1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the ocular, pulmonary or rectal routes.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters, wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

For oral or parenteral administration to human patients the daily dosage levels of the compounds of the invention will be from 0.01 to 30 mg/kg (in single or divided doses) and preferably will be in the range 0.01 to 5 mg/kg. Thus tablets will contain 1 mg to 0.4 g of compound for administration singly or two or more at a time, as appropriate. The physician will in any event determine the actual dosage which will be most suitable for any particular patient and it will vary with the age, weight and response of the particular patient. The above dosages are, of course only exemplary of the average case and there may be instances where higher or lower doses are merited, and such are within the scope of the invention.

Oral administration is preferred. Preferably, administration takes place shortly before an effect is required.

For veterinary use, a compound of the invention, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

Thus according to a further aspect, the invention provides a pharmaceutical formulation containing a compound of formula (I), as defined in the first aspect, or a pharmaceutically acceptable salt thereof, and a pharmaceutically acceptable adjuvant, diluent or carrier.

The invention is illustrated by the following non-limiting examples in which the following abbreviations and definitions are used:

| | |
|---|---|
| Arbacel ® | filter agent |
| Boc | tert-butoxycarbonyl |
| Celite ® | filter agent |
| CDI | carbonyldiimidazole |
| Δ | heat |
| DCCI | dicyclohexylcarbodiimide |
| DCM | dichloromethane |
| DIBAL | diisobutylaluminium hydride |
| DMF | N,N-dimethylformamide |
| Ex | Example |
| ES+ | electrospray ionisation positive scan |
| ES− | electrospray ionisation negative scan |
| h | hours |
| HOBt | 1-hydroxybenzotriazole |
| m/z | mass spectrum peak |
| min | minutes |
| MS | mass spectrum |
| NMR | nuclear magnetic resonance |
| Prec | Precursor |

-continued

| | |
|---|---|
| Prep | Preparation |
| THF | tetrahydrofuran |
| TS+ | thermospray ionisation positive scan |
| WSCDI | water soluble carbodiimide (1-[3-dimethylaminopropyl]-3-ethylcarbodiimide hydrochloride) |

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; DMSO, dimethylsulphoxide. The abbreviation psi means pounds per square inch and LRMS means low resolution mass spectrometry. Where thin layer chromatography (TLC) has been used it refers to silica gel TLC using silica gel 60 F$_{254}$ plates, R$_f$ is the distance travelled by a compound divided by the distance travelled by the solvent front on a TLC plate. Melting points were determined using a Perkin Elmer DSC7 at a heating rate of 20° C./minute).

Where indicated, compounds were characterised as their hydrochloride salts. A typical procedure for formation of hydrochloride salts is given in Example 48. The procedure can be carried out with other solvents e.g. diethyl ether or DCM.

EXAMPLE 1

{3-[3-Methoxy-4-(methylsulfanyl)phenoxy]-4-pyridinyl}methylamine

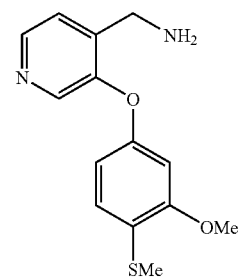

The product from Preparation 57 (1.56 g, 5.73 mmol) was dissolved in THF and treated with borane-THF complex (1M in THF). The resulting yellow solution was heated at reflux for 4.5 h. After cooling to room temperature, the reaction was quenched by the cautious addition of 6M hydrochloric acid (17 mL) and then the mixture was heated at reflux for a further 4 h. The reaction mixture was evaporated to remove most of the THF and the resulting yellow solution was washed with Et$_2$O (2×10 mL). The aqueous fraction was basified to pH 12 using NaOH pellets and extracted with EtOAc (3×20 mL), then DCM (3×20 mL). The combined organic layers were dried (MgSO$_4$) and evaporated to a pink oil. Purification by flash chromatography [SiO$_2$; DCM/MeOH/880 NH$_3$ (95:5:0.5)] afforded the title compound as a rose coloured oil (646 mg, 42%); δ$_H$ (CDCl$_3$, 400 MHz) 2.42 (3H, s), 3.87 (3H, s), 3.92 (2H, s), 6.48 (1H, dd), 6.58 (1H, d), 7.15 (1H, d), 7.41 (1H, d), 8.22 (1H, s), 8.39 (1H, d).

EXAMPLES 2–16

The following compounds of formula Ic, i.e. compounds of general formula I wherein $R^1$ and $R^2$ are hydrogen, were prepared in an analogous fashion to Example 1, starting from the nitrile intermediate indicated.

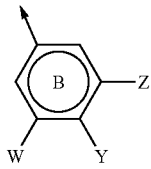

(Ic)

| Ex | Prec | L | M | Q | U | W | Y | Data |
|---|---|---|---|---|---|---|---|---|
| 2 | Prep. 52 | —C(H)— | —C(H)— | —N— | —C(H)— | 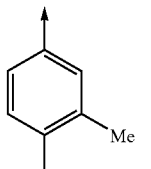 | | $\delta_H$(CDCl$_3$, 400MHz) 8.28 (1H, d), 8.07(1H, s), 7.29 (1H, d), 6.74(1H, d), 6.61 (1H, s), 6.57(1H, m), 4.33 (2H, m), 3.84(2H, s), 3.06 (2H, m), 1.54(2H, brs); MS m/z(TS$^+$)275(MH$^+$) |
| 3 | Prep. 47 | —C(H)— | —C(H)— | —N— | —C(H)— | SMe | Me | Bis HCl salt: $\delta_H$(d$_6$-DMSO, 300MHz) 8.73(3H, brs), 8.50(1H, d), 8.18(1H, s), 7.78(1H, d), 7.27(1H, d), 7.02(2H, m), 4.17(2H, m), 2.48(3H, s), 2.26(3H, s); MS m/z(TS$^+$)261 (MH$^+$) |
| 4 | Prep. 49 | —C(H)— | —C(H)— | —N— | —C(H)— | 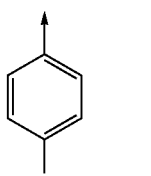 | | $\delta$(CDCl$_3$, 400MHz) 8.26 (1H, d), 8.07(1H, s), 7.29 (1H, d), 7.14(2H, d), 6.78 (2H, d), 3.78(2H, s), 2.35 (3H, s), 1.46(2H, brs); MS m/z(TS$^+$)247(MH$^+$) |
| 5 | Prep. 50 | —N— | —C(H)— | —C(H)— | CH | 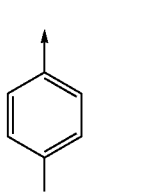 | | $\delta_H$(CDCl$_3$, 300MHz) 8.34 (1H, m), 7.27(2H, d), 7.14 (2H, m), 6.91(2H, d), 4.05 (2H, s), 2.47(3H, s), 1.83 (2H, s); MS m/z(TS$^+$)247 (MH$^+$) |

-continued

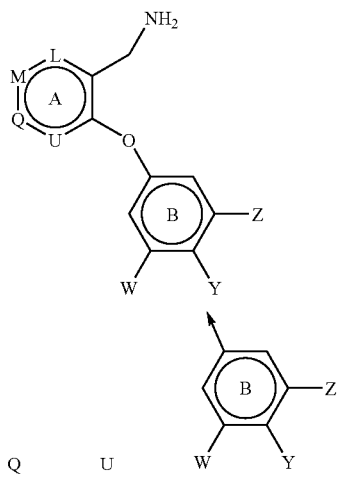

(Ic)

| Ex | Prec | L | M | Q | U | W Y | Data |
|---|---|---|---|---|---|---|---|
| 6 | Prep. 51 | —C(H)— | —C(H)— | —N— | —C(H)— | 3-F, 4-SMe phenyl | Used crude as free base in following step as 50:50 mixture with phenol from prep. 7; δ_H(CDCl_3, 400MHz) 8.40(1H, d), 8.20 (1H, s), 7.42(1H, d), 7.17–7.27 (1H, m), 6.64–6.69 (2H, m), 3.87(2H, s), 2.40 (3H, s) |
| 7 | Prep. 54 | —C(H)— | —C(H)— | —N— | —C(H)— | 3-CF_3, 4-SMe phenyl | δ_H(CDCl_3, 400MHz) 2.45 (3H, s), 3.86(2H, s), 7.00 (1H, dd), 7.23(1H, d), 7.36(1H, d), 7.43(1H, d), 8.17(1H, s), 8.41(1H, d) |
| 8 | Prep. 55 | —C(H)— | —C(H)— | —N— | —C(H)— | 3-SMe, 4-Me phenyl | δ_H(CDCl_3, 400MHz) 2.26 (3H, s), 2.38(3H, s), 3.89 (2H, s), 6.55(1H, dd), 6.78(1H, d), 7.03(1H, d), 7.35(1H, d), 8.14(1H, s), 8.34(1H, d); MS m/z(TS+) 261(MH+) |
| 9 | Prep. 53 | —C(H)— | —C(H)— | —N— | —C(H)— | 4-Et phenyl | δ_H(CDCl_3, 400MHz) 1.20 (3H, t), 2.60(2H, q), 3.88 (2H, s), 6.85(2H, d), 7.12 (2H, d), 7.34(1H, d), 8.13 (1H, s), 8.32(1H, d); MS m/z(TS+)229(MH+) |
| 10 | Prep. 56 | —C(H)— | —C(H)— | —N— | —C(H)— | indanyl | δ_H(CDCl_3, 400MHz) 2.10 (2H, m), 2.41(2H, s), 2.87 (4H, m), 3.95(2H, s), 6.75 (1H, dd), 6.83(1H, s), 7.16(1H, d), 7.38(1H, d), 8.15(1H, s), 8.33(1H, d) |

-continued
(Ic)
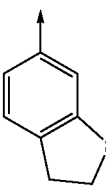
| Ex | Prec | L | M | Q | U | W Y | Data |
|----|------|---|---|---|---|-----|------|
| 11 | 58 | —C(H)— | —C(H)— | —N— | —C(H)— | 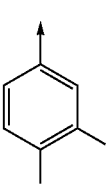 | δ$_H$(CDCl$_3$, 400MHz) 3.23 (2H, t), 3.37(2H, t), 3.88 (2H, s), 6.58(1H, dd), 6.80(1H, s), 7.09(1H, d), 7.37(1H, d), 8.18(1H, d), 8.36(1H, d); MS m/z(TS$^+$) 259(MH$^+$) |
| 12 | 59 | —C(H)— | —C(H)— | —N— | —C(H)— | 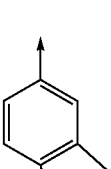 | δ$_H$(CDCl$_3$, 300MHz) 1.23 (3H, t), 2.46(3H, s), 2.76 (2H, q), 3.93(2H, s), 6.78 (1H, dd), 6.86(1H, d), 7.22(1H, d), 7.41(1H, d), 8.20(1H, s), 8.40(1H, d); MS m/z(TS$^+$)275(MH$^+$) |
| 13 | 60 | —C(H)— | —C(H)— | —N— | —C(H)— | 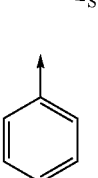 | δ$_H$(CDCl$_3$, 300MHz) 3.95 (2H, s), 4.23(4H, m), 6.85 (2H, m), 7.22(1H, d), 7.43 (1H, d), 8.21(1H, s), 8.41 (1H, d); MS m/z(TS$^+$)259 (MH$^+$) |
| 14 | 61 | —C(H)— | —C(H)— | —N— | —C(H)— | 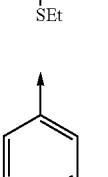 | δ$_H$(CDCl$_3$, 300MHz) 1.33 (3H, t), 2.93(2H, q), 3.93 (2H, s), 6.92(2H, d), 7.36 (2H, d), 7.42(1H, d), 8.21 (1H, s), 8.41(1H, d); MS m/z(TS$^+$)261(MH$^+$) |
| 15 | 62 | —C(H)— | —C(H)— | —N— | —C(H)— |  | δ$_H$(CDCl$_3$, 400MHz) 2.43 (3H, s), 3.85(2H, s), 6.83 (1H, dd), 6.98(1H, d), 7.15(1H, d), 7.40(1H, d), 8.18(1H, s), 8.39(1H, d); MS m/z(ES$^+$)281(MH$^+$) |

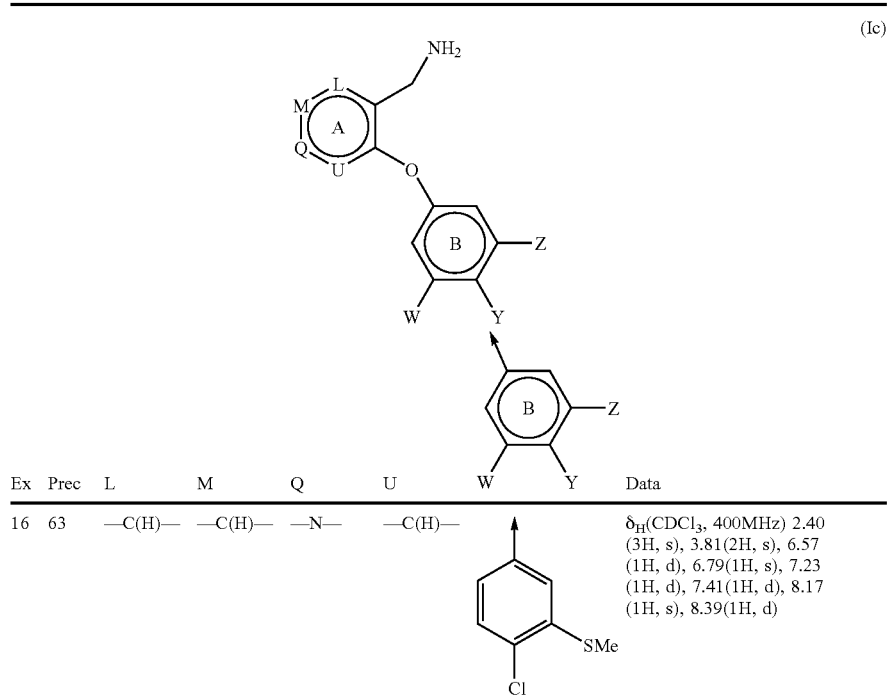

| Ex | Prec | L | M | Q | U | W | Y | Data |
|----|------|---|---|---|---|---|---|------|
| 16 | 63 | —C(H)— | —C(H)— | —N— | —C(H)— | | (3-SMe, 4-Cl phenyl) | $\delta_H$(CDCl$_3$, 400MHz) 2.40 (3H, s), 3.81(2H, s), 6.57 (1H, d), 6.79(1H, s), 7.23 (1H, d), 7.41(1H, d), 8.17 (1H, s), 8.39(1H, d) |

EXAMPLE 17

{3-[4-(Trifluoromethyl)phenoxy]-2-pyrazinyl}methylamine

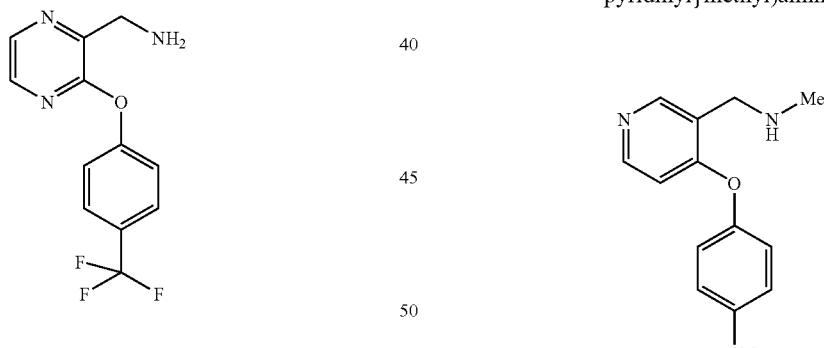

The product from Preparation 48 (500 mg, 1.9 mmol) was dissolved in a mixture of water/acetic acid/pyridine (1:1:2; 15 mL), sodium hypophosphite (1.0 g, 11.4 mmol) was added and the mixture was adjusted to pH ca. 4 by the addition of glacial AcOH. Raney nickel (50% slurry in water, 200 mg) was added and the mixture was heated at 50° C. for 2 h. After cooling to room temperature, the catalyst was removed by filtration and the pH of the filtrate was adjusted to pH 10–11 by the addition of sodium carbonate and water. The mixture was then extracted three times with DCM and the combined organic layers were washed with water, dried (MgSO$_4$) and evaporated. The resulting oil was purified twice by flash chromatography, initially [SiO$_2$; DCM/MeOH, (95:5)] and afterwards [SiO$_2$; EtOAc/pentane/methanol (80:20:2)] to afford the title compound as cream solid (110 mg, 22%); $\delta$(CDCl$_3$, 400 MHz) 8.26 (1H, s), 7.96 (1H, s), 7.67 (2H, d), 7.24 (2H, d), 4.19 (2H, s); MS m/z (TS$^+$) 270 (MH$^+$).

EXAMPLE 18

N-Methyl-N-({4-[4-(methylsulfanyl)phenoxy]-3-pyridinyl}methyl)amine

The product from Preparation 25 (3.73 g, 15 mmol) was dissolved in 8M MeNH$_2$ in ethanol solution (19 mL) and the mixture was stirred at room temperature for 2 h. Sodium borohydride (1.7 g, 45 mmol) was added portionwise over 30 min and the resulting mixture was stirred for 15 h. The mixture was then evaporated to dryness, diluted with water (10 mL) and quenched by the cautious addition of 2M HCl until effervescence ceased. After standing for 5 minutes, the mixture was basified by the addition of 2M sodium hydroxide solution and extracted with EtOAc (2×25 mL) and evaporated to a yellow oil. The title compound was obtained as an oil after purification by flash chromatography [SiO$_2$; DCM/methanol/880 NH$_3$ (93:7:1)] and the hydrochloride salt was formed by dissolution in EtOAc (200 mL) and treatment with 1M HCl in diethyl ether (35 mL). The product was collection by filtration and dried under vacuum (3.40 g, 68%); Bis HCl salt: δ$_H$ (CD$_3$OD, 300 MHz) 2.54 (3H, s), 2.90 (3H, s), 4.60 (2H, s), 7.26 (1H, d), 7.37 (2H, d), 7.48 (2H, d), 8.73 (1H, d), 9.03 (1H, s); MS m/z (TS$^+$) 261 (MH$^+$).

EXAMPLES 19–33

The following compounds of formula Id, i.e. compounds of general formula I where R$^1$ is methyl, R$^2$ is hydrogen, M is —N— and Q, U and L are —C(H)—, were prepared by methods analogous to Example 18 from the aldehyde precursors indicated.

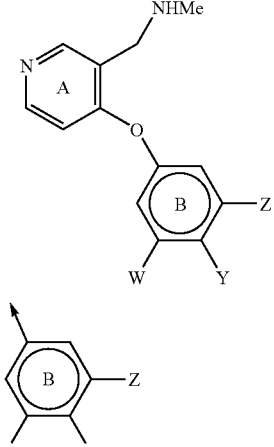

(Id)

| Ex | Precursor aldehyde | W Y Z | Data |
|---|---|---|---|
| 19 | Prep. 22 | 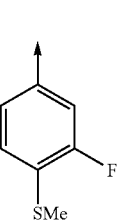 | Bis HCl salt: δ$_H$(CD$_3$OD, 300MHz) 2.39 (3H, s), 2.57(3H, s), 2.91(3H, s), 4.60 (2H, s), 7.23(3H, m), 7.42(1H, d), 8.76 (1H, d), 9.01(1H, s); MS m/z(ES$^+$)275 (MH$^+$) |
| 20 | Prep. 23 | 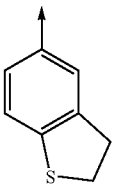 | Bis HCl salt: δ$_H$(CD$_3$OD, 400MHz) 2.50 (3H, s), 2.86(3H, s), 4.53(2H, s), 7.20 (2H, t), 7.27(1H, d), 7.52(1H, t), 8.69(1H, d), 8.95(1H, s); MS m/z(TS$^+$)279(MH$^+$) |
| 21 | Prep. 21 | 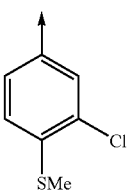 | Bis HCl salt: δ$_H$(CD$_3$OD, 400MHz) 2.86 (3H, s), 3.37(2H, t), 3.43(2H, m), 4.52 (2H, s), 7.08(2H, m), 7.21(1H, s), 7.35 (1H, d), 8.62(1H, d), 8.88(1H, s); MS m/z (TS$^+$)272(M$^+$) |
| 22 | Prep. 27 |  | δ$_H$(CDCl$_3$, 400MHz) 2.42(3H, s), 2.45 (3H, s), 3.83(2H, s), 6.59(1H, d), 6.97 (1H, dd), 7.12(1H, s), 7.20(1H, d), 8.34 (1H, d), 8.48(1H, s); MS m/z(TS$^+$)295, 297(MH$^+$) |

-continued
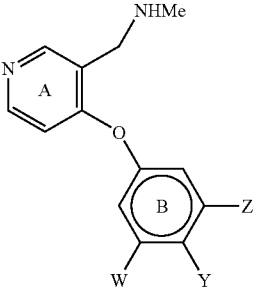
(Id)
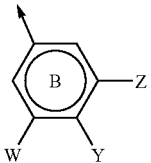
| Ex | Precursor aldehyde | W Y Z (B ring) | Data |
|---|---|---|---|
| 23 | Prep. 24 | 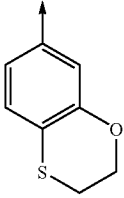 | Free base: δ_H(CDCl_3, 400MHz) 2.45(3H, s), 3.15(2H, m), 3.85(2H, s), 4.42(2H, m), 6.55–6.65(3H, m), 7.03(1H, d), 8.35 (1H, d), 8.47(1H, s); MS m/z(TS⁺)289 (MH⁺) |
| 24 | Prep. 26 | 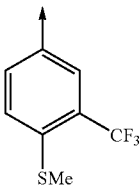 | Bis HCl salt: δ_H(CD_3OD, 400MHz) 2.59 (3H, s), 2.86(3H, s), 4.53(2H, s), 7.25 (1H, d), 7.60(1H, d), 7.70(2H, m), 8.70 (1H, d), 8.98(1H, s); MS m/z(TS⁺)329 (MH⁺) |
| 25 | Prep. 32 | 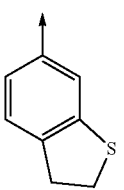 | Bis HCl salt: δ_H(d_6-DMSO, 400MHz)2.64 (3H, s), 3.30(2H, m), 3.49(2H, m), 4.34 (2H, s), 7.02(2H, m), 7.32(1H, s), 7.40 (1H, d), 8.66(1H, d), 8.98(1H, s), 9.60 (2H, brs); MS m/z(TS⁺)273(MH⁺) |
| 26 | Prep. 29 | 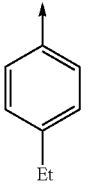 | δ_H(CDCl_3, 400MHz) 1.22(3H, t), 2.45 (3H, s), 2.64(2H, q), 3.86(2H, s), 6.54 (1H, d), 6.95(2H, d), 7.20(2H, d), 8.27 (1H, d), 8.44(1H, s); MS m/z(TS⁺)243 (MH⁺) |
| 27 | Prep. 30 | 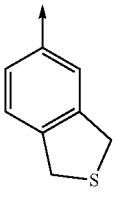 | Bis HCl salt: δ_H(CD_3OD, 400MHz) 2.91 (3H, s), 4.31(4H, s), 4.59(2H, s), 7.22–7.30 (2H, m), 7.33(1H, s), 7.53(1H, d), 8.75(1H, d), 9.00(1H, s); MS m/z(TS⁺) 273(MH⁺) |

-continued

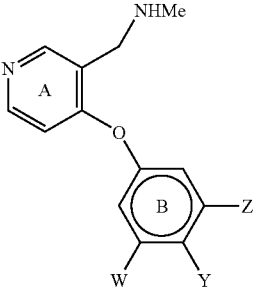

(Id)

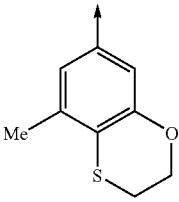

| Ex | Precursor aldehyde | W Y Z (B) | Data |
|---|---|---|---|
| 28 | Prep. 31 | 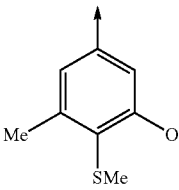 | Bis HCl salt: δ_H(CD_3OD, 400MHz) 2.27 (3H, s), 2.87(3H, s), 3.21(2H, m), 4.41 (2H, m), 4.52(2H, s), 6.71(1H, d), 6.79 (1H, d), 7.24(1H, d), 8.68(1H, d), 8.91 (1H, s); MS m/z 303(MH$^+$) |
| 29 | Prep. 18 | 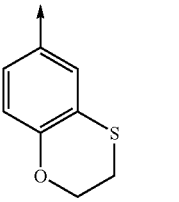 | Bis HCl salt: δ_H(CD_3OD, 400MHz) 2.30 (3H, s), 2.51(3H, s), 2.87(3H, s), 3.88 (3H, s), 4.53(2H, s), 6.86(1H, s), 6.94 (1H, s), 7.28(1H, m), 8.70(1H, m), 8.96 (1H, m); MS m/z(TS$^+$)305(MH$^+$) |
| 30 | Prep. 33 | 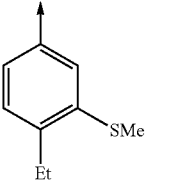 | δ_H(CDCl_3, 400MHz) 2.42(3H, s), 3.10 (2H, m), 3.82(2H, s), 4.38(2H, m), 6.56 (1H, d), 6.65(1H, dd), 6.74(1H, d), 6.80 (1H, d), 8.27(1H, d), 8.42(1H, s); MS m/z (TS$^+$)289(MH$^+$) |
| 31 | Prep. 35 | 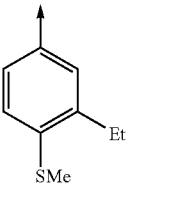 | Bis HCl salt: δ_H(CD_3OD, 400MHz) 1.26 (3H, t), 2.48(3H, s), 2.76(2H, q), 2.90 (3H, s), 4.58(2H, s), 7.06(1H, d), 7.25 (1H, d), 7.28(1H, s), 7.37(1H, d), 8.71 (1H, d), 9.00(1H, s); MS m/z(ES$^+$)289 (MH$^+$) |
| 32 | Prep. 36 |  | Bis HCl salt: δ_H(CD_3OD, 300MHz) 1.26 (3H, t), 2.55(3H, s), 2.80(2H, q), 2.92 (3H, s), 4.59(2H, s), 7.00–7.07(3H, m), 7.46(1H, d), 8.74(1H, d), 9.00(1H, s); MS m/z(TS$^+$)289(MH$^+$) |

-continued

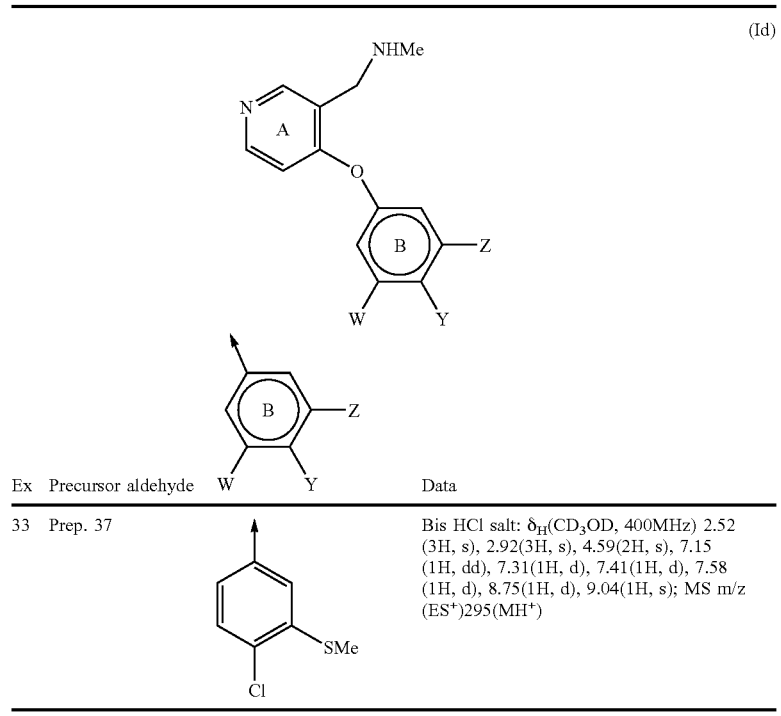

| Ex | Precursor aldehyde | W | Y | Data |
|---|---|---|---|---|
| 33 | Prep. 37 | 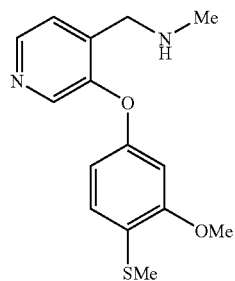 | | Bis HCl salt: $\delta_H$(CD$_3$OD, 400MHz) 2.52 (3H, s), 2.92(3H, s), 4.59(2H, s), 7.15 (1H, dd), 7.31(1H, d), 7.41(1H, d), 7.58 (1H, d), 8.75(1H, d), 9.04(1H, s); MS m/z (ES$^+$)295(MH$^+$) |

EXAMPLE 34

{3-[3-Methoxy-4-(methylsulfanyl)phenoxy]-4-pyridinyl}-N-methylmethanamine

Pentafluorophenol (852 mg, 4.64 mmol) was dissolved in diethyl ether (15 mL) and the solution cooled to 0° C. Formic acid (209 μL, 5.56 mol) was added followed by DCCl (956 mg, 4.64 mmol) and the mixture was stirred for 10 min. The white suspension was filtered off and the filtrate was cooled to 0° C. and treated with a solution of the product from Example 1 (640 mg, 2.32 mmol) in DCM (10 mL) and triethylamine (323 μL, 2.32 mmol). The resulting reaction mixture was stirred at room temperature for 6 h. The solvents were then removed under reduced pressure and the residue was basified with water (10 mL)/880 NH$_3$ (1 mL) and extracted with DCM (4×15 mL). The combined organic extracts were dried (MgSO$_4$) and evaporated to an oily-solid residue (844 mg, ca. 100%); $\delta_H$ (CDCl$_3$, 400 MHz) 2.42 (3H, s), 3.87 (3H, s), 4.55 (2H, s), 5.98 (1H, brs), 6.50 (1H, dd), 6.59 (1H, d), 7.17 (1H, d), 7.31 (1H, d), 8.21 (1H, s), 8.29 (1H, s), 8.38 (1H, d). This material was carried on directly to the reduction stage without further purification. The crude formamide was dissolved in THF (10 mL) and treated with borane-THF complex (1M in THF, 7 mL, 7 mmol). The resulting pale yellow solution was heated at reflux under nitrogen for 3.5 h. After cooling to room temperature, the reaction was quenched by the careful addition of 6 M HCl (7 mL) and the mixture was subsequently heated to reflux for 3 h. Most of the THF was removed by evaporation and the resulting aqueous solution was washed with diethyl ether (2×10 mL) and then basified by the addition of 880 NH$_3$. Extraction with DCM (4×10 mL) followed by drying of the combined extracts (MgSO$_4$) and evaporation afforded a clear oil. Purification by flash chromatography [SiO$_2$; DCM/MeOH/880 NH$_3$ (95:5:0.5)] gave the desired compound as a colourless oil. A portion of this material (300 mg) was dissolved in DCM (5 mL) and treated with 1M HCl in diethyl ether (5 mL) and the resulting mixture was evaporated to dryness twice from DCM. The resulting yellow oil was dissolved in DCM (5 mL) and treated with diethyl ether dropwise to induce precipitation. The solvents were removed under reduced pressure and the resulting pale yellow solid was dried under vacuum (345 mg); Bis HCl salt: $\delta_H$(CD$_3$OD, 400 MHz) 2.39 (3H, s), 2.87 (3H, s), 3.85 (3H, s), 4.58 (2H, s), 6.87 (1H, dd), 6.95 (1H, d), 7.29 (1H, d), 8.06 (1H, d), 8.28 (1H, s), 8.58 (1H, d); MS m/z (TS$^+$) 291 (MH$^+$).

EXAMPLES 35–47

The following compounds of formula Ie, i.e. compounds of general formula I where R$^1$ is methyl, R$^2$ is hydrogen, Q is —N— and U, M and L are —C(H)—, were prepared by methods analogous to Example 34 from the primary amines indicated.

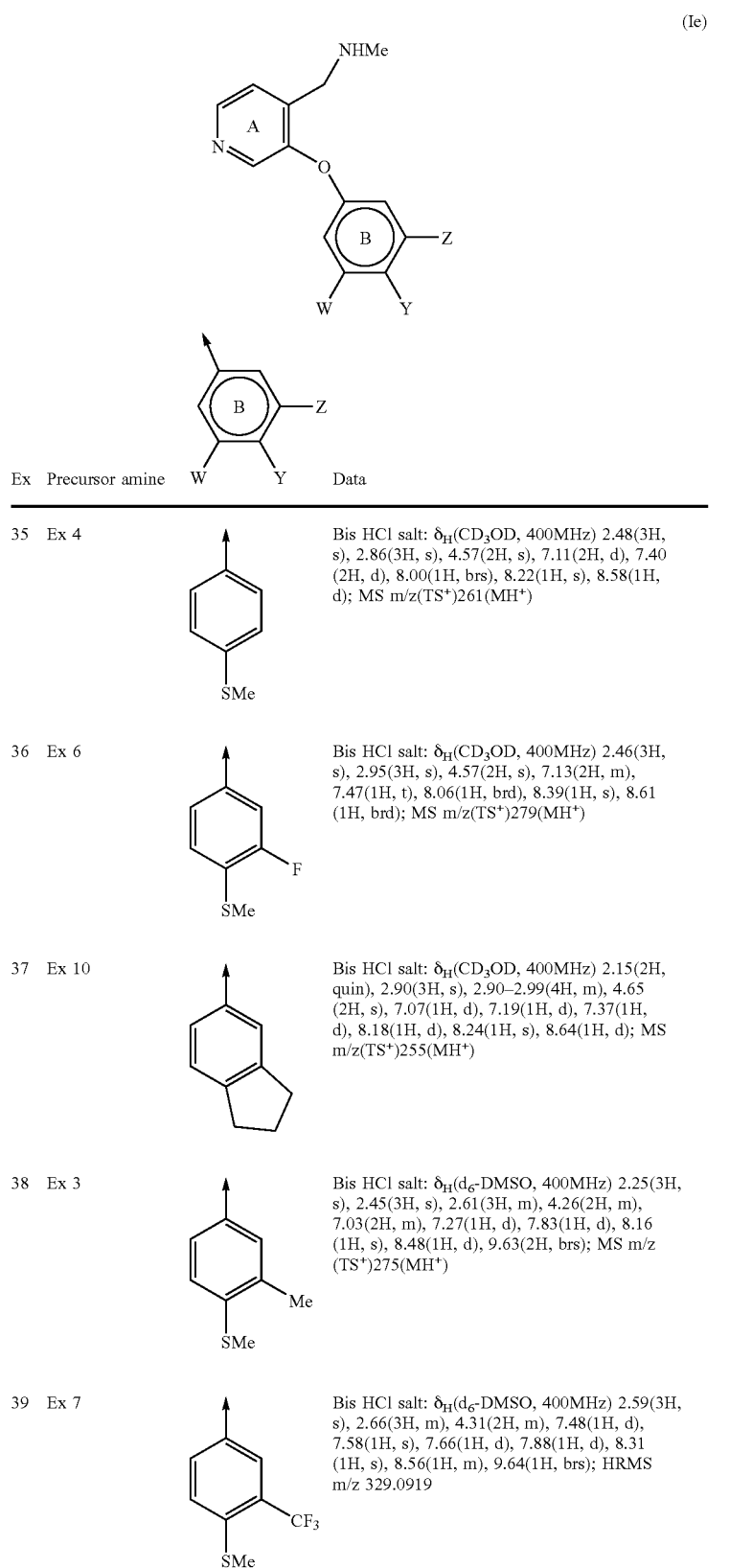

| Ex | Precursor amine | W | Y | Data |
|---|---|---|---|---|
| 35 | Ex 4 | | | Bis HCl salt: δ$_H$(CD$_3$OD, 400MHz) 2.48(3H, s), 2.86(3H, s), 4.57(2H, s), 7.11(2H, d), 7.40 (2H, d), 8.00(1H, brs), 8.22(1H, s), 8.58(1H, d); MS m/z(TS$^+$)261(MH$^+$) |
| 36 | Ex 6 | | | Bis HCl salt: δ$_H$(CD$_3$OD, 400MHz) 2.46(3H, s), 2.95(3H, s), 4.57(2H, s), 7.13(2H, m), 7.47(1H, t), 8.06(1H, brd), 8.39(1H, s), 8.61 (1H, brd); MS m/z(TS$^+$)279(MH$^+$) |
| 37 | Ex 10 | | | Bis HCl salt: δ$_H$(CD$_3$OD, 400MHz) 2.15(2H, quin), 2.90(3H, s), 2.90–2.99(4H, m), 4.65 (2H, s), 7.07(1H, d), 7.19(1H, d), 7.37(1H, d), 8.18(1H, d), 8.24(1H, s), 8.64(1H, d); MS m/z(TS$^+$)255(MH$^+$) |
| 38 | Ex 3 | | | Bis HCl salt: δ$_H$(d$_6$-DMSO, 400MHz) 2.25(3H, s), 2.45(3H, s), 2.61(3H, m), 4.26(2H, m), 7.03(2H, m), 7.27(1H, d), 7.83(1H, d), 8.16 (1H, s), 8.48(1H, d), 9.63(2H, brs); MS m/z (TS$^+$)275(MH$^+$) |
| 39 | Ex 7 | | | Bis HCl salt: δ$_H$(d$_6$-DMSO, 400MHz) 2.59(3H, s), 2.66(3H, m), 4.31(2H, m), 7.48(1H, d), 7.58(1H, s), 7.66(1H, d), 7.88(1H, d), 8.31 (1H, s), 8.56(1H, m), 9.64(1H, brs); HRMS m/z 329.0919 |

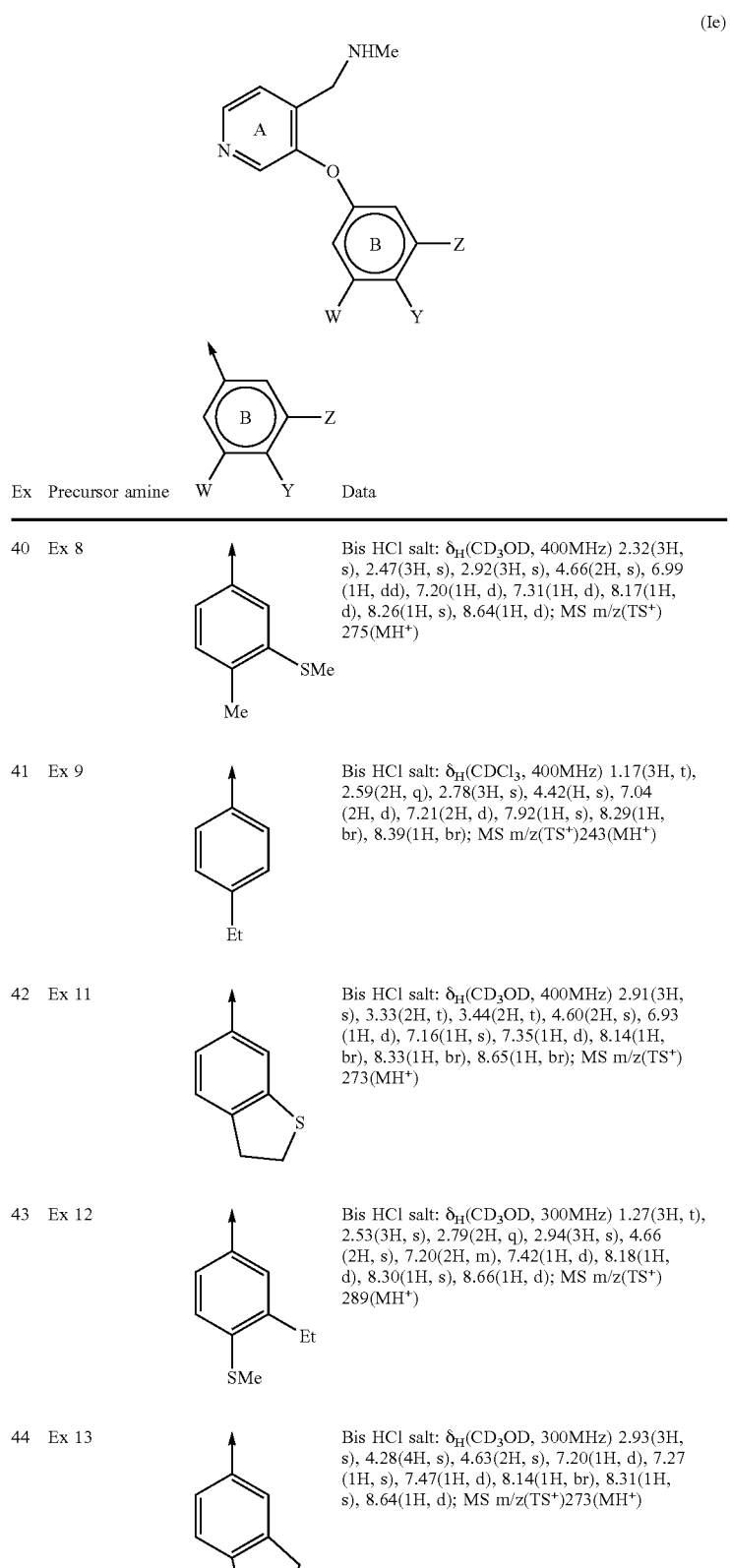

| Ex | Precursor amine | W | Y | Data |
|---|---|---|---|---|
| 40 | Ex 8 | | SMe, Me | Bis HCl salt: δ$_H$(CD$_3$OD, 400MHz) 2.32(3H, s), 2.47(3H, s), 2.92(3H, s), 4.66(2H, s), 6.99 (1H, dd), 7.20(1H, d), 7.31(1H, d), 8.17(1H, d), 8.26(1H, s), 8.64(1H, d); MS m/z(TS$^+$) 275(MH$^+$) |
| 41 | Ex 9 | | Et | Bis HCl salt: δ$_H$(CDCl$_3$, 400MHz) 1.17(3H, t), 2.59(2H, q), 2.78(3H, s), 4.42(H, s), 7.04 (2H, d), 7.21(2H, d), 7.92(1H, s), 8.29(1H, br), 8.39(1H, br); MS m/z(TS$^+$)243(MH$^+$) |
| 42 | Ex 11 | | (2,3-dihydrobenzothiophene) | Bis HCl salt: δ$_H$(CD$_3$OD, 400MHz) 2.91(3H, s), 3.33(2H, t), 3.44(2H, t), 4.60(2H, s), 6.93 (1H, d), 7.16(1H, s), 7.35(1H, d), 8.14(1H, br), 8.33(1H, br), 8.65(1H, br); MS m/z(TS$^+$) 273(MH$^+$) |
| 43 | Ex 12 | | Et, SMe | Bis HCl salt: δ$_H$(CD$_3$OD, 300MHz) 1.27(3H, t), 2.53(3H, s), 2.79(2H, q), 2.94(3H, s), 4.66 (2H, s), 7.20(2H, m), 7.42(1H, d), 8.18(1H, d), 8.30(1H, s), 8.66(1H, d); MS m/z(TS$^+$) 289(MH$^+$) |
| 44 | Ex 13 | | (1,3-dihydrobenzothiophene) | Bis HCl salt: δ$_H$(CD$_3$OD, 300MHz) 2.93(3H, s), 4.28(4H, s), 4.63(2H, s), 7.20(1H, d), 7.27 (1H, s), 7.47(1H, d), 8.14(1H, br), 8.31(1H, s), 8.64(1H, d); MS m/z(TS$^+$)273(MH$^+$) |

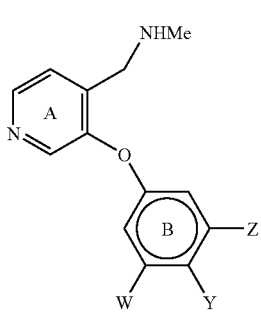

| Ex | Precursor amine | W | Y | Z | Data |
|---|---|---|---|---|---|
| 45 | Ex 14 | | | 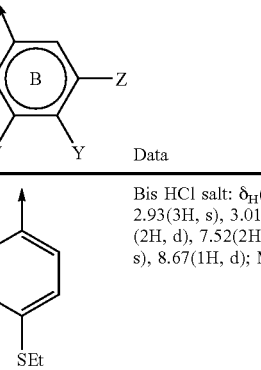 (SEt at para) | Bis HCl salt: δ_H(CD₃OD, 300MHz) 1.36(3H, t), 2.93(3H, s), 3.01(2H, q), 4.65(2H, s), 7.30 (2H, d), 7.52(2H, d), 8.19(1H, d), 8.35(1H, s), 8.67(1H, d); MS m/z(TS⁺)275(MH⁺) |
| 46 | Ex 15 | | | 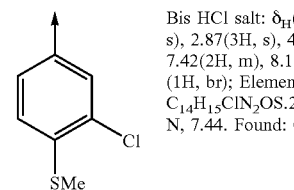 (Cl, SMe) | Bis HCl salt: δ_H(CD₃OD, 400MHz) 2.50(3H, s), 2.87(3H, s), 4.60(2H, s), 7.30(1H, br), 7.42(2H, m), 8.16(1H, br), 8.37(1H, br), 8.64 (1H, br); Elemental analysis calculated for C₁₄H₁₅ClN₂OS.2HCl.0.5H₂O: C, 44.64, H, 4.82, N, 7.44. Found: C, 44.89, H, 4.71, N, 7.29 |
| 47 | Ex 16 | | | 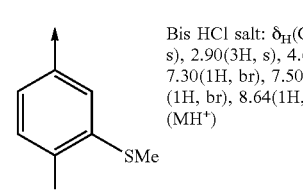 (SMe, Cl) | Bis HCl salt: δ_H(CD₃OD, 400MHz) 2.47(3H, s), 2.90(3H, s), 4.62(2H, s), 7.05(1H, br), 7.30(1H, br), 7.50(1H, br), 8.17(1H, br), 8.36 (1H, br), 8.64(1H, br); MS m/z(ES⁺)295 (MH⁺) |

Alternatively, the amine of Example 38 can be prepared from the amide of Preparation 64 as follows:

BH₃.THF (1M soln in THF, 400 mL, 0.4 mol) was added over 10 min to a solution of preparation 64 (28.3 g, 0.098 mol) in THF (200 mL) at room temperature under nitrogen. The mixture was heated at reflux for 4 h then allowed to cool to room temperature before being quenched by the cautious addition of MeOH (500 mL). After stirring for 30 min the solvent was removed in vacuo and the residue was taken up in MeOH (100 mL) and treated cautiously with 6M HCl (700 mL). The mixture was heated at reflux for 45 min then cooled to room temperature and partially neutralised by the addition of 12M NaOH (300 mL) with cooling. The mixture was taken to pH 6 with Na₂HPO₄ (s) and shaken with EtOAc (800 mL) to give 3 layers. The lower, aqueous layer was basified to pH 10 with 12M NaOH and extracted with EtOAc (2×600 mL). The middle layer was partitioned between 2M NaOH (200 mL) and EtOAc (500 mL) and the combined organic extracts from the lower and middle layers were dried (MgSO₄) and evaporated to give the title compound (18 g, 67%) as a yellow oil. This was taken up in isopropyl alcohol (400 mL) and a solution of L-tartaric acid (9.5 g, 63 mmol) in isopropyl alcohol (300 mL) was added dropwise with stirring. The resulting suspension was heated briefly to reflux until all the solid had dissolved and then allowed to cool to room temperature. The resulting precipitate was filtered, dried in vacuo and recrystallised from EtOH (twice from 200 mL) to give the mono-tartrate salt of Example 38 (20.24 g) as a crystalline solid; δ_H(CD₃OD, 400 MHz) 2.34 (3H, s), 2.46 (3H, s), 2.78 (3H, s), 4.33 (2H, s), 4.40 (2H, s), 7.00 (2H, m), 7.31 (1H, d), 7.58 (1H, d), 8.07 (1H, s), 8.36 (1H, d); MS m/z (ES⁺) 275 (MH⁺)

EXAMPLE 48

N-{[4-(2,3-Dihydro-1,4-benzoxathiin-7-yloxy)-6-methyl-3-pyridinyl]methyl}-N-methylamine

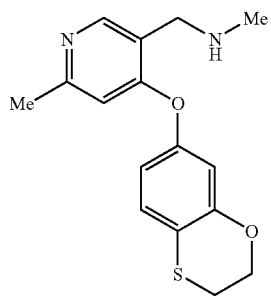

The product from Preparation 40 (1.23 g, 3.89 mmol) was treated with borane-THF complex (1M in THF) (10 mL, 10 mmol) and the mixture was heated at reflux for 2 h. After being cooled to room temperature the reaction was quenched by the addition of methanol (10 mL). The resulting solution was evaporated to a yellow oil which was treated with 6M hydrochloric acid (10 mL) and heated at reflux for 1 h. After cooling to room temperature the solution was poured cautiously onto excess solid $K_2CO_3$ and the resulting mixture was extracted with DCM (2×30 mL). The combined organic layers were dried ($MgSO_4$) and evaporated to a clear oil. Purification of this oil by flash chromatography [$SiO_2$; DCM/MeOH/880 $NH_3$(93:7:1)] afforded the product as a clear oil. This was re-dissolved in EtOAc (30 mL) and treated with 1M HCl in diethyl ether (10 mL, 10 mmol) to form the bis hydrochloride salt which was collected by filtration and washed with excess diethyl ether (1.026 g, 67%); Bis HCl salt: $\delta_H$ ($CD_3OD$, 400 MHz) 2.61 (3H, s), 2.81 (3H, s), 3.17 (2H, m), 4.41 (2H, m), 4.46 (2H, s), 6.81 (2H, brs), 7.12 (1H, s), 7.20 (1H, d), 8.79 (1H, s); MS m/z ($ES^+$) 303 ($MH^+$).

EXAMPLES 49–52

The following compounds of formula If, i.e. compounds of general formula I where $R^1$ is methyl, $R^2$ is hydrogen, Q is —C(Me)-, M is —N— and L and U are —C(H)—, were prepared by methods analogous to Example 48 from the precursor amide indicated.

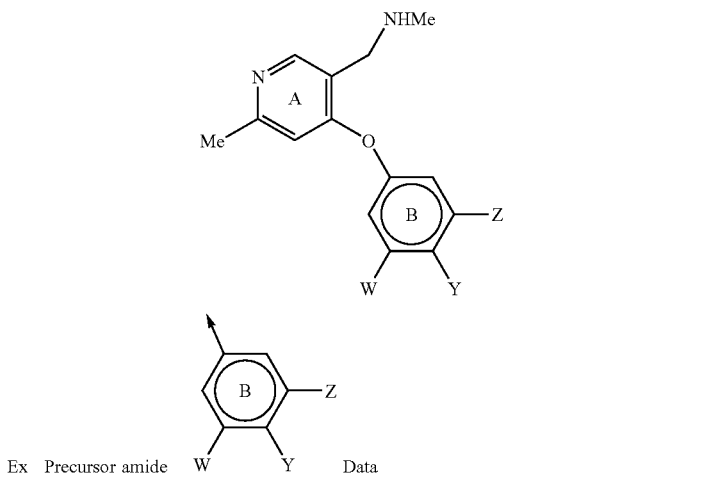

(If)

| Ex | Precursor amide | W | Y | Data |
|---|---|---|---|---|
| 49 | Prep 41 | 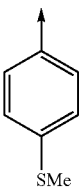 | | Bis HCl salt: $\delta_H$($CD_3OD$, 400MHz) 2.54(3H, s), 2.62(3H, s), 2.87(3H, s), 4.51(2H, s), 7.08 (1H, s), 7.27(2H, d), 7.47(2H, d), 8.81(1H, s); MS m/z($TS^+$)275($MH^+$) |
| 50 | Prep 42 | 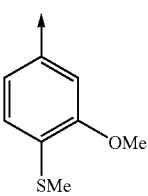 | | Bis HCl salt: $\delta_H$($CDCl_3$, 300MHz) 2.29(3H, s), 2.38(3H, s), 3.02(3H, s), 3.82(3H, s), 4.40 (2H, s), 6.22(3H, brm), 7.16(2H, m); MS m/z ($TS^+$)305($MH^+$) |

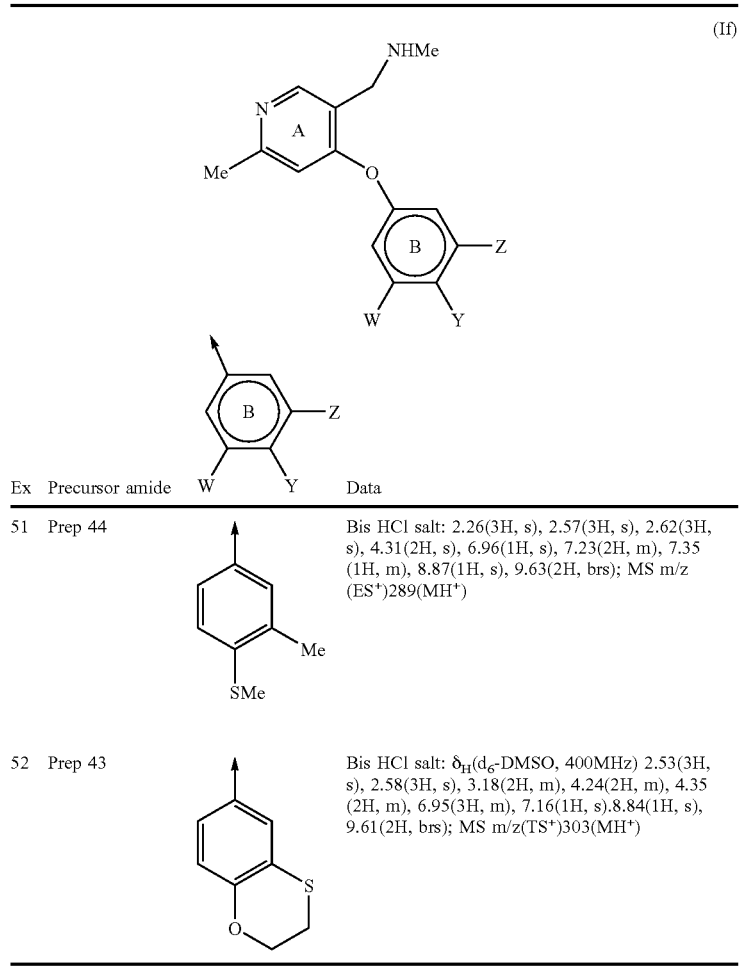

| Ex | Precursor amide | W | Y | Data |
|---|---|---|---|---|
| 51 | Prep 44 | Me | SMe | Bis HCl salt: 2.26(3H, s), 2.57(3H, s), 2.62(3H, s), 4.31(2H, s), 6.96(1H, s), 7.23(2H, m), 7.35 (1H, m), 8.87(1H, s), 9.63(2H, brs); MS m/z (ES$^+$)289(MH$^+$) |
| 52 | Prep 43 | (benzodioxinethiane ring) | | Bis HCl salt: $\delta_H$(d$_6$-DMSO, 400MHz) 2.53(3H, s), 2.58(3H, s), 3.18(2H, m), 4.24(2H, m), 4.35 (2H, m), 6.95(3H, m), 7.16(1H, s).8.84(1H, s), 9.61(2H, brs); MS m/z(TS$^+$)303(MH$^+$) |

EXAMPLE 53

{6-Methyl-4-[4-methyl-3-(methylsulfanyl)phenoxy]-3-pyridinyl}methanamine

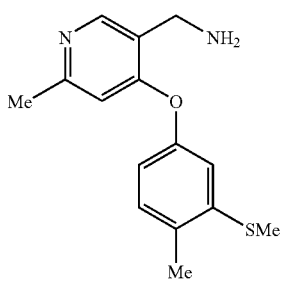

The title compound was prepared from the amide of Preparation 45-by the method of Example 48; $\delta_H$ (CD$_3$OD, 400 MHz) 2.30 (3H, s), 2.36 (3H, s), 2.44 (3H, s), 3.92 (2H, s), 6.48 (1H, s), 6.81 (1H, d), 7.00 (1H, s), 7.23 (1H, d), 8.29 (1H, s).

EXAMPLE 54

{6-Methyl-4-[4-chloro-3-(methylsulfanyl)phenoxy]-3-pyridinyl}methanamine

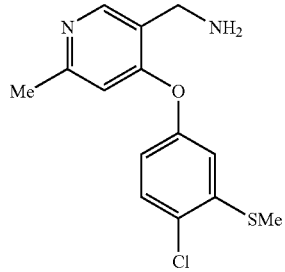

The title compound was prepared from the amide of Preparation 46 by the method of Example 48; δ$_H$ (CDCl$_3$, 400 MHz) 2.39 (3H, s), 2.42 (3H, s), 3.96 (2H, s), 6.39 (1H, s), 6.75 (1H, d), 6.86 (1H, s), 7.34 (1H, d), 8.36 (1H, s); MS m/z (ES$^+$)295 (MH$^+$).

EXAMPLE 55

{4-[4-Chloro-3-(methylsulfanyl)phenoxy]-6-methyl-3-pyridinyl}-N-methylmethanamine

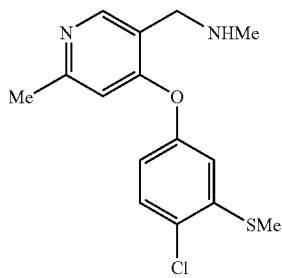

The title compound was prepared from the primary amine of Example 54 by the method of Example 34; δ$_h$ (CD$_3$OD, 400 MHz) 2.47 (3H, s), 2.63 (3H, s), 2.86 (3H, s), 4.50 (2H, s), 7.10 (2H, br), 7.34 (1H, br), 7.54 (1H, br), 8.82 (1H, s); MS m/z (ES$^+$) 309 (MH$^+$).

EXAMPLES 56–57

The following compounds of formula Ig, i.e. compounds of general formula I where R$^1$ is methyl, R$^2$ is hydrogen, U is —N— and L, M and Q are —C(H)—, were prepared by methods analogous to Example 18 from the aldehyde precursors indicated.

EXAMPLE 58

| Ex | Precursor aldehyde | W, Y, Z structure | Data |
|---|---|---|---|
| 56 | Prep 38 | 4-SMe-phenyl | δ$_H$(CD$_3$OD, 400MHz) 2.43(3H, s), 2.48 (3H, s), 3.84(2H, s), 7.03(2H, d), 7.08 (1H, dd), 7.33(2H, d), 7.81(1H, d), 7.98 (1H, d); MS m/z(TS$^+$)261(MH$^+$) |
| 57 | Prep 39 | 3-Me-4-SMe-phenyl | δ$_H$(CD$_3$OD, 400MHz) 2.33(3H, s), 2.43 (3H, s), 2.45(3H, s), 3.83(2H, s), 6.94 (2H, m), 7.09(1H, dd), 7.27(1H, d), 7.81 (1H, d), 7.98(1H, d); MS m/z(TS$^+$)275 (MH$^+$) |

N-{[4-(2,3-Dihydro-1-benzothien-6-yloxy)-3-pyridinyl]methyl}-N,N-dimethylamine

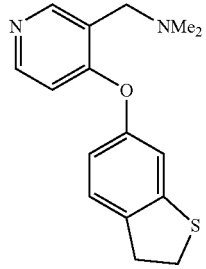

The bis hydrochloride salt of Example 25 (354 mg, 1,02 mmol) was dissolved in DCM (10 mL) and treated with formaldehyde (37% aqueous, 83 μL, 1.02 mmol) and stirred at room temperature for 1 h. Sodium triacetoxyborohydride (435 mg, 2.05 mmol) was added and stirring was maintained for 30 min. The reaction was quenched by the addition of 2M HCl and then basified with 10% aqueous $K_2CO_3$ solution. The resulting mixture was extracted with EtOAc (3×50 mL) and the combined organic fractions were dried over $MgSO_4$, filtered and evaporated to a volume of 50 mL. Ethereal HCl was added while stirring to form the bis hydrochloride salt, and stirring was continued at room temperature for 1 h. The mixture was then evaporated to dryness and the gummy residue stirred in diethyl ether for 30 min. The resulting off-white solid was collected by filtration (220 mg, 60%); Bis HCl salt $\delta_H$ ($CD_3OD$, 400 MHz) 3.06 (6H, s), 3.35 (2H, m), 3.47 (2H, m), 4.72 (2H, s), 7.00 (1H, d), 7.23 (1H, s), 7.31 (1H, d), 7.40 (1H, d), 8.65 (1H, d), 9.11 (1H, s); MS m/z ($TS^+$) 287 ($MH^+$).

EXAMPLES 59–93

The following compounds of formula Ih, i.e. compounds of general formula I where $R^1$ and $R^2$ are methyl were prepared from the appropriate secondary or primary amines indicated, using methods analogous to Example 58. When primary amines were used as starting materials three equivalents of formaldehyde and four equivalents of sodium triacetoxyborohydride were used.

(Ih)

| Ex | Prec amine | L | M | Q | U | W | Y | Data |
|---|---|---|---|---|---|---|---|---|
| 59 | Ex 22 | —C(H)— | —N— | —C(H)— | —C(H)— | 4-SMe, 3-Cl phenyl | | Bis HCl salt: $\delta_H$ ($CDCl_3$, 400MHz) 2.27(6H, s), 2.44 (3H, s), 3.55(2H, s), 6.60(1H, d), 6.96 (1H, d), 7.08(1H, s), 7.19(1H, d), 8.34 (1H, d), 8.53(1H, s); MS m/z($TS^+$)309, 311($MH^+$) |
| 60 | Ex 48 | —C(H)— | —N— | —C(Me)— | —C(H)— | 2,3-dihydro-1,4-benzoxathiin-6-yl | | Bis HCl salt: $\delta_H$ ($CD_3OD$, 400MHz) 2.61(3H, s), 2.98 (6H, s), 3.17(2H, m), 4.41(2H, m), 4.60 (2H, s), 6.81(2H, s+d), 7.08(1H, s), 7.20(1H, d), 8.85 (1H, s); MS m/z ($ES^+$)317($MH^+$) |

-continued

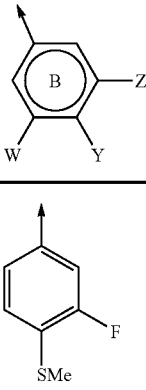

(Ih)

| Ex | Prec amine | L | M | Q | U | W Y | Data |
|---|---|---|---|---|---|---|---|
| 61 | Ex 20 | —C(H)— | —N— | —C(H)— | —C(H)— | 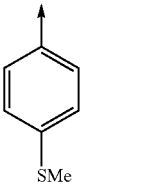 | Bis HCl salt: δ$_H$ (CD$_3$OD, 400MHz) 2.48(3H, s), 3.00 (6H, s), 4.67(2H, s), 7.21(2H, t), 7.32 (1H, d), 7.52(1H, d), 8.73(1H, d), 9.05 (1H, s); MS m/z (TS$^+$)293(MH$^+$) |
| 62 | Ex 49 | —C(H)— | —N— | —C(Me)— | —C(H)— | 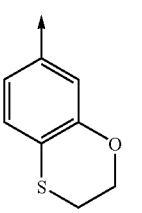 | Bis HCl salt: δ$_H$ (CD$_3$OD, 400MHz) 2.57(3H, s), 2.66 (3H, s), 3.02(6H, s), 4.64(2H, s), 7.08 (1H, s), 7.31(1H, d), 7.47(1H, d), 8.93 (1H, s); MS m/z (ES$^+$)289(MH$^+$) |
| 63 | Ex 23 | —C(H)— | —N— | —C(H)— | —C(H)— | 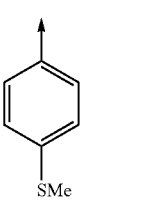 | Bis HCl salt: δ$_H$(d$_6$-DMSO, 400MHz) 2.78(6H, s), 3.19 (2H, m), 4.37(2H, m), 4.46(2H, s), 6.83(1H, d), 6.92 (1H, s), 7.02(1H, d), 7.21(1H, d), 8.63 (1H, d), 9.02(1H, s) |
| 64 | Ex 4 | —C(H)— | —C(H)— | —N— | —C(H)— | 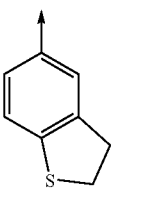 | Bis HCl salt: δ$_H$ (CD$_3$OD, 400MHz) 2.47(3H, s), 3.00 (6H, s), 4.70(2H, s), 7.23(2H, d), 7.40 (2H, d), 8.17(1H, d), 8.28(1H, s), 8.60 (1H, d); MS m/z (ES$^+$)275(MH$^+$) |
| 65 | Ex 21 | —C(H)— | —N— | —C(H)— | —C(H)— |  | Bis HCl salt: δ$_H$ (CD$_3$OD, 400MHz) 3.04(6H, s), 3.37 (2H, m), 3.45(2H, m), 4.68(2H, s), 7.10(1H, d), 7.26 (2H, m), 7.38(1H, d), 8.74(1H, d), 9.05 (1H, s); MS m/z (ES$^+$)287(MH$^+$) |

-continued (Ih)

| Ex | Prec amine | L | M | Q | U | W / Y | Data |
|---|---|---|---|---|---|---|---|
| 66 | Ex 6 | —C(H)— | —C(H)— | —N— | —C(H)— | 3-F, 4-SMe phenyl | Bis HCl salt: $\delta_H$ (CD$_3$OD, 400MHz) 2.44(3H, s), 2.97 (6H, s), 4.59(2H, s), 7.07(2H, m), 7.44 (1H, t), 7.90(1H, d), 8.33(1H, s), 8.56 (1H, d); MS m/z (TS$^+$)293(MH$^+$) |
| 67 | Ex 3 | —C(H)— | —C(H)— | —N— | —C(H)— | 3-Me, 4-SMe phenyl | Bis HCl salt: $\delta_H$(d$_6$-DMSO, 300MHz) 2.26(3H, s), 2.52 (3H, obs), 2.80(6H, s), 4.23(2H, s), 7.06 (2H, m), 7.27(1H, d), 7.96(1H, d), 8.19 (1H, s), 8.50(1H, d); MS m/z(TS$^+$)288 (MH$^+$) |
| 68 | Ex 52 | —C(H)— | —N— | —C(Me)— | —C(H)— | 2,3-dihydro-1,4-benzoxathiin-6-yl | Bis HCl salt: $\delta_H$(d$_6$-DMSO, 400MHz) 2.58(3H, s), 2.77 (6H, s), 3.18(2H, m), 4.34(2H, m), 4.44 (2H, s), 6.94(2H, m), 7.02(1H, s), 7.18 (1H, d), 8.96(1H, s), 11.28(1H, brs); MS m/z(TS$^+$)317(MH$^+$) |
| 69 | Ex 5 | —N— | —C(H)— | —C(H)— | —C(H)— | 4-SMe phenyl | Bis HCl salt: $\delta_H$ (CD$_3$OD, 400MHz) 2.44(3H, s), 3.00 (6H, s), 4.64(2H, s), 7.07(2H, d), 7.34 (3H, m), 7.46(1H, m), 8.41(1H, m); MS m/z(ES$^+$)275(MH$^+$) |
| 70 | Ex 2 | CH | CH | N | CH | 2,3-dihydro-1,4-benzoxathiin-6-yl | Bis HCl salt: $\delta_H$(d$_6$-DMSO, 400MHz) 2.73(6H, s), 3.15 (2H, m), 4.30(2H, m), 4.40(2H, d), 6.83(2H, m), 6.98 (1H, s), 7.91(1H, d), 8.11(1H, s), 8.43 (1H, d), 11.07(1H, brs); MS m/z(TS$^+$) 303(MH$^+$) |

-continued

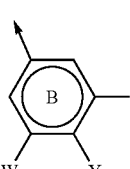

(Ih)

| Ex | Prec amine | L | M | Q | U | W Y | Data |
|---|---|---|---|---|---|---|---|
| 71 | Ex 24 | —C(H)— | —N— | —C(H)— | —C(H)— | 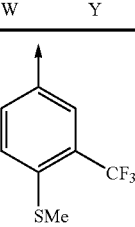 | Bis HCl salt: δ$_H$ (CD$_3$OD, 400MHz) 2.58(3H, s), 3.01 (6H, s), 4.69(2H, s), 7.26(1H, d), 7.60 (1H, d), 7.70(2H, m), 8.72(1H, d), 9.05(1H, s); MS m/z (TS$^+$)343(MH$^+$) |
| 72 | Ex 51 | —C(H)— | —N— | —C(Me)— | —C(H)— | 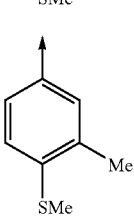 | Bis HCl salt: δ$_H$(d$_6$-DMSO, 400MHz) 2.26(3H, s), 2.49 (3H, s), 2.57(3H, s), 2.80(6H, s), 4.47 (2H, s), 6.98(1H, s), 7.21(2H, m), 7.33 (1H, m), 8.97(1H, s), 11.20(1H, bs); MS m/z(TS$^+$)303(MH$^+$) |
| 73 | Ex 7 | —C(H)— | —C(H)— | —N— | —C(H)— | 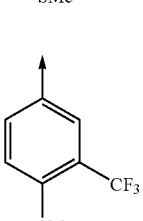 | Bis HCl salt: δ$_H$(d$_6$-DMSO, 400MHz) 2.58(3H, s), 2.82 (6H, s), 4.46(1H, m), 7.47(1H, d), 7.62 (1H, s), 7.65(1H, d), 7.95(1H, d), 8.33 (1H, s), 8.56(1H, d), 11.10(1H, brs); HRMS m/z 343.1099 (MH$^+$) |
| 74 | Ex 8 | —C(H)— | —C(H)— | —N— | —C(H)— | 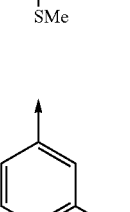 | Bis HCl salt: δ$_H$ (CD$_3$OD, 400MHz) 2.32(3H, s), 2.49 (3H, s), 3.07(6H, s), 4.80(2H, s), 7.00 (1H, dd), 7.24(1H, d), 7.31(1H, d), 8.30 (1H, s), 8.31(1H, d), 8.66(1H, d); MS m/z (TS$^+$)289(MH$^+$) |
| 75 | Ex 29 | —C(H)— | —N— | —C(H)— | —C(H)— | 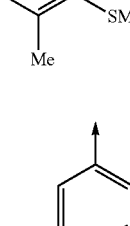 | Bis HCl salt: δ$_H$ (CD$_3$OD, 400MHz) 2.29(3H, s), 2.50 (3H, s), 3.03(6H, s), 3.87(3H, s), 4.70 (2H, s), 6.88(1H, s), 6.99 (1H, s), 7.30 (1H, d), 7.72(1H, d), 9.09(1H, s); MS m/z (ES$^+$)319(MH$^+$) |

-continued (Ih)

| Ex | Prec amine | L | M | Q | U | W Y | Data |
|---|---|---|---|---|---|---|---|
| 76 | Ex 28 | —C(H)— | —N— | —C(H)— | —C(H)— | 8-Me-2,3-dihydro-1,4-benzoxathiin-6-yl (Me, S, O) | Bis HCl salt: δ$_H$ (CD$_3$OD, 400MHz) 2.23(3H, s), 3.00 (6H, s), 3.19(2H, m), 4.39(2H, m), 4.64 (2H, s), 6.69(1H, s), 6.76(1H, s), 7.25 (1H, d), 8.69(1H, d), 8.97(1H, s); MS m/z 317(MH$^+$) |
| 77 | Ex 34 | —C(H)— | —C(H)— | —N— | —C(H)— | 3-OMe-4-SMe-phenyl | Bis HCl salt: δ$_H$ (CD$_3$OD, 400MHz) 2.39(3H, s), 3.02 (6H, s), 3.86(3H, s), 4.71(2H, s), 6.86 (1H, dd), 6.97(1H, d), 7.29(1H, d), 8.13 (1H, d), 8.30(1H, s), 8.59(1H, d); MS m/z (TS$^+$)305(MH$^+$) |
| 78 | Ex 30 | —C(H)— | —N— | —C(H)— | —C(H)— | 2,3-dihydro-1,4-benzoxathiin-6-yl | Bis HCl salt: δ$_H$(D$_6$-DMSO, 400MHz) 2.79(6H, s), 3.16 (2H, m), 4.33(2H, m), 4.49(2H, s), 6.90–7.00(2H, m), 7.02(1H, d), 7.18 (1H, d), 8.66(1H, d), 9.10(1H, s); MS m/z 303(MH$^+$) |
| 79 | Ex 31 | —C(H)— | —N— | —C(H)— | —C(H)— | 3-SMe-4-Et-phenyl | Bis HCl salt: δ$_H$ (CD$_3$OD, 400MHz) 1.26(3H, t), 2.49 (3H, s), 2.77(2H, q), 3.06(6H, s), 4.73 (2H, s), 7.08(1H, d), 7.29(2H, m), 7.38 (1H, d), 8.73(1H, d), 9.09(1H, s); MS m/z (TS$^+$)303(MH$^+$) |
| 80 | Ex 32 | —C(H)— | —N— | —C(H)— | —C(H)— | 3-Et-4-SMe-phenyl | Bis HCl salt: δ$_H$ (CD$_3$OD, 300MHz) 1.27(3H, t), 2.55 (3H, s), 2.80(2H, q), 3.07(6H, s), 4.74 (2H, s), 7.20–7.31 (3H, m), 8.75(1H, d), 9.10(1H, s); MS m/z(ES$^+$)303(MH$^+$) |

-continued (Ih)

| Ex | Prec amine | L | M | Q | U | W Y | Data |
|---|---|---|---|---|---|---|---|
| 81 | Ex 27 | —C(H)— | —N— | —C(H)— | —C(H)— | benzothiophene (2,3-dihydro, S at position) | Bis HCl salt: δ$_H$ (CD$_3$OD, 300MHz) 3.09(6H, s), 4.33 (4H, s), 4.75(2H, s), 7.25(1H, dd), 7.32 (1H, d), 7.37(1H, d), 7.53(1H, d), 8.78 (1H, d), 9.13(1H, s); MS m/z(TS$^+$)287 (MH$^+$) |
| 82 | Ex 33 | —C(H)— | —N— | —C(H)— | —C(H)— | phenyl with Cl and SMe | Bis HCl salt: δ$_H$ (CD$_3$OD, 400MHz) 2.48(3H, s), 3.03 (6H, s), 4.70(2H, s), 7.13(1H, d), 7.30 (1H, d), 7.40(1H, s), 7.46(1H, d), 8.76 (1H, d), 9.10(1H, s); MS m/z(ES$^+$)309 (MH$^+$) |
| 83 | Ex 42 | —C(H)— | —C(H)— | —N— | —C(H)— | 2,3-dihydrobenzothiophene | Bis HCl salt: δ$_H$ (CD$_3$OD, 400MHz) 3.05(6H, s), 3.32 (2H, t), 3.45(2H, t), 4.75(2H, s), 6.95 (1H, d), 7.19(1H, s), 7.36(1H, d), 8.25 (1H, d), 8.35(1H, br), 8.65(1H, br); MS m/z(ES$^+$)287 (MH$^+$) |
| 84 | Ex 43 | —C(H)— | —C(H)— | —N— | —C(H)— | phenyl with Et and SMe | Bis HCl salt: δ$_H$(CD$_3$OD, 300 MHz) 1.26(3H, t), 2.53(3H, s), 2.79 (2H, q), 3.08(6H, s), 4.80(2H, s), 7.21 (2H, m), 7.43(1H, d0, 8.28(1H, d), 8.35 (1H, s), 8.66(1H, d); MS m/z(TS$^+$)303 (MH$^+$) |
| 85 | Ex 44 | —C(H)— | —C(H)— | —N— | —C(H)— | 1,3-dihydroisobenzothiophene | Bis HCl salt: δ$_H$(CD$_3$OD, 300 MHz) 3.04(6H, s), 4.29(4H, s), 4.71 (2H, s), 7.18(1H, dd), 7.24(1H, d), 7.44(1H, d), 8.07 (1H, d), 8.30(1H, s), 8.60(1H, d); MS m/z (TS$^+$)287(MH$^+$) |

-continued

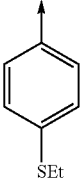

(Ih)

| Ex | Prec amine | L | M | Q | U | W Y | Data |
|---|---|---|---|---|---|---|---|
| 86 | Ex 45 | —C(H)— | —C(H)— | —N— | —C(H)— | 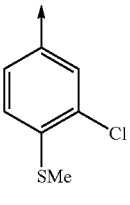 (SEt para) | Bis HCl salt: δ$_H$(CD$_3$OD, 300 MHz) 1.27(3H, t), 2.96(2H, q), 3.01 (6H, s), 4.70(2H, s), 7.23(2H, d), 7.45 (2H, d), 8.13(1H, d), 8.30(1H, s), 8.60 (1H, d); MS m/z (TS$^+$)289(MH$^+$) |
| 87 | Ex 46 | —C(H)— | —C(H)— | —N— | —C(H)— | (Cl, SMe) | Bis HCl salt: δ$_H$(CD$_3$OD, 400 MHz) 2.50(3H, s), 3.01(6H, s), 4.72 (2H, s), 7.30(1H, dd), 7.40(1H, d), 7.45(1H, d), 8.07 (1H, d), 8.39(1H, br), 8.63(1H, br); Elemental analysis calculated for C$_{15}$H$_{17}$ClN$_2$OS.2HCl: C,45.27, H , 5.27, N, 7.04. Found: C, 45.54, H, 5.36, N, 6.67 |
| 88 | Ex 47 | —C(H)— | —C(H)— | —N— | —C(H)— | 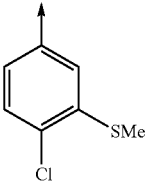 (SMe, Cl) | Bis HCl salt: δ$_H$(CD$_3$OD, 400 MHz) 2.44(3H, s), 2.99(6H, s), 4.62 (2H, s), 6.96(1H, dd), 7.19(1H, s), 7.46(1H, d), 7.92 (1H, d), 8.30(1H, s), 8.54(1H, d); MS m/z (ES$^+$)309(MH$^+$) |
| 89 | Ex 53 | —C(H)— | —N— | —C(Me)— | —C(H)— | 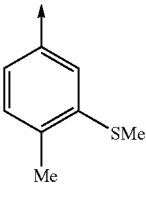 (SMe, Me) | Bis HCl salt: δ$_H$ (CD$_3$OD, 400MHz) 2.35(3H, s), 2.49 (3H, s), 2.66(3H, s), 3.04(6H, s), 4.66 (2H, s), 7.01(1H, dd), 7.10(1H, s), 7.24(1H, d), 7.35 (1H, d), 8.94(1H, s); MS m/z(ES$^-$)373 M+2HCl−H$^+$) |

-continued

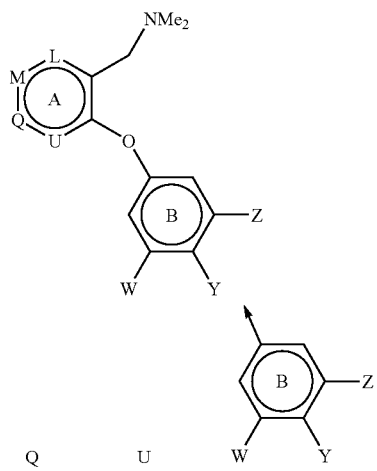

(Ih)

| Ex | Prec amine | L | M | Q | U | W Y | Data |
|----|-----------|---|---|---|---|-----|------|
| 90 | Ex 55 | —C(H)— | —N— | —C(Me)— | —C(H)— | ![3-SMe-4-Cl-phenyl] | Bis HCl salt: δ_H (CD_3OD, 400MHz) 2.47(3H, s), 2.63 (3H, s), 3.02(6H, s), 4.61(2H, s), 7.07 (1H, d), 7.13(1H, s), 7.33(1H, s), 7.55 (1H, d), 8.88(1H, s); MS m/z(ES⁺)323 (MH⁺) |
| 91 | Ex 56 | —C(H)— | —C(H)— | —C(H)— | —N— | ![4-SMe-phenyl] | Bis HCl salt: δ_H (CD_3OD, 400MHz) 2.49(3H, s), 2.98 (6H, s), 4.50(2H, s), 7.15(2H, d), 7.20 (1H, dd), 7.36(2H, d), 8.00(1H, d), 8.19 (1H, d); MS m/z (TS⁺)275(MH⁺) |
| 92 | Ex 57 | —C(H)— | —C(H)— | —C(H)— | —N— | ![3-Me-4-SMe-phenyl] | Bis HCl salt: δ_H (CD_3OD, 400MHz) 2.34(3H, s), 2.47 (3H, s), 2.98(6H, s), 4.50(2H, s), 7.04 (2H, m), 7.20(1H, dd), 7.29(1H, d), 8.01(1H, d), 8.18 (1H, d); MS m/z (TS⁺)289(MH⁺) |
| 93 | Ex 102 | —C(H)— | —N⁺(—O⁻)— | —C(H)— | —C(H)— | ![4-SMe-phenyl] | Bis HCl salt: δ_H (CD_3OD, 300MHz) 2.52(3H, s), 3.05 (6H, s), 4.67(2H, s), 7.20(1H, d), 7.33 (2H, d), 7.47(2H, d), 8.77(1H, d), 9.20 (1H, brs); MS m/z (TS⁺)291(MH⁺) |

EXAMPLE 94

N-({4-[3-Methoxy-4-(methylsulfanyl)phenoxy]-3-pyridinyl}methyl)-N,N-dimethylamine

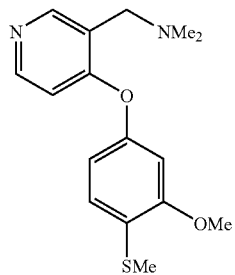

The product from Preparation 28 (527 mg, 1.91 mmol) was dissolved in $CH_2Cl_2$ (10 mL) and treated with triethylamine (0.4 mL, 2.87 mmol), acetic acid (164 μL, 2.87 mmol) and dimethylamine hydrochloride (234 mg, 2.87 mmol). The resulting mixture was stirred at room temperature for 30 min before the addition of sodium triacetoxyborohydride (608 mg, 2.87 mmol) and the solution was left to stir for 18 h. The mixture was basified by the addition of saturated sodium bicarbonate solution and extracted with DCM (3×10 mL). The combined organic layers were dried ($MgSO_4$) and evaporated to an orange oil. Purification by flash chromatography [$SiO_2$; DCM/MeOH/880 $NH_3$ (95:5:0.5)] gave the title compound as a yellow oil. The hydrochloride salt was formed by dissolution in DCM, treatment with excess ethereal HCl and evaporation. The resulting solid was azeotroped twice with DCM to afforded the desired title compound bis hydrochloride salt as a cream solid (56 mg, 77%); Bis HCl salt: $\delta_H$ ($CD_3OD$, 400 MHz) 2.45 (3H, s), 3.08 (6H, s), 3.90 (3H, s), 4.72 (2H, s), 6.97 (1H, d), 7.08 (1H, s), 7.32 (1H, d), 7.35 (1H, d), 8.75 (1H, d), 9.08 (1H, s); MS m/z (TS$^+$) 305 (MH$^+$).

EXAMPLES 95–99

The following compounds of formula Ii, i.e. compounds of general formula I where L, Q and U are —C(H)—, M is —N—, and $R^1$ and $R^2$ are methyl, were prepared by the method described for Example 94 starting from the appropriate aldehyde, as indicated.

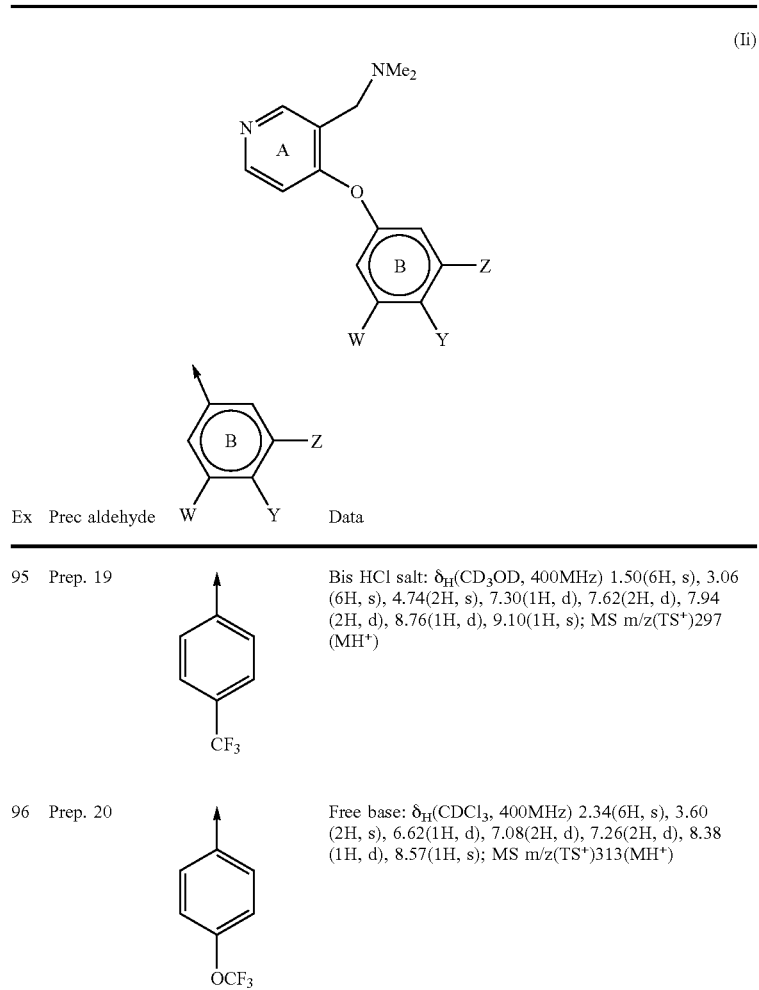

-continued

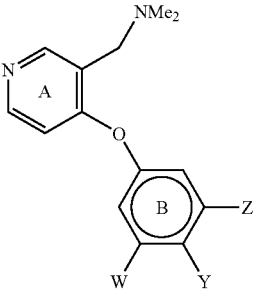

(Ii)

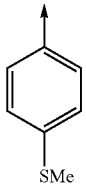

| Ex | Prec aldehyde | W | Y | Data |
|---|---|---|---|---|
| 97 | Prep. 25 | 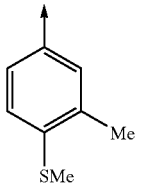 | | Bis HCl salt: δ_H(CD_3OD, 300MHz) 2.55(3H, s), 3.07 (6H, s), 4.74(2H, s), 7.28(1H, d), 7.36(2H, d), 7.48 (2H, d), 8.77(1H, d), 9.06(1H, s); MS m/z(TS$^+$)275 (MH$^+$) |
| 98 | Prep. 22 | 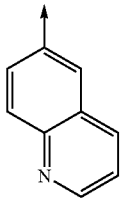 | | Bis HCl salt: δ_H(CD_3OD, 300MHz) 2.39(3H, s), 2.55 (3H, s), 3.07(6H, s), 4.74(2H, s), 7.24(3H, m), 7.42 (1H, d), 8.78(1H, d), 9.12(1H, s); MS m/z(ES$^+$)289 (MH$^+$) |
| 99 | Prep. 34 | 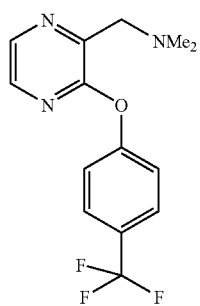 | | Free base: δ_H(CDCl_3, 400MHz) 2.37(6H, s), 3.62 (2H, s), 6.69(1H, d), 7.38–7.50(3H, m), 8.08(1H, d), 8.15(1H, d), 8.38(1H, d), 8.61(1H, s), 8.90(1H, d); MS m/z(TS$^+$)280(MH$^+$) |

EXAMPLE 100

N,N-Dimethyl-N-({3-[4-(trifluoromethyl)phenoxy]-2-pyrazinyl}methyl)amine

The product from Example 17 (110 mg, 0.41 mmol) was dissolved in formic acid (96%, 0.46 mL, 12.3 mmol) and formaldehyde (37% aqueous, 0.34 mL, 12.3 mmol). The mixture was then heated to 80° C. for 3.75 h. The cooled mixture was diluted with 10 mL of water, solid sodium carbonate was slowly added to adjust to pH 11 and the mixture was extracted three times with EtOAc. The combined organic fractions were washed with brine, dried (MgSO_4) and evaporated to a gum. Purification by flash chromatography [SiO_2; EtOAc/pentane/MeOH (80:20:2) afforded the title compound, which was converted to the hydrochloride salt by dissolution in DCM and treatment with excess ethereal HCl. After removal of solvents the material was obtained as a pale cream-brown solid (40 mg, 26%); Free base: δ_H (CDCl_3, 400 MHz) 2.40 (6H, s), 3.80 (2H, s), 7.26 (2H, d), 7.68 (2H, d), 8.00 (1H, s), 8.32 (1H, s); MS m/z (TS$^+$) 298 (MH$^+$).

EXAMPLE 101

3-(1-Azetidinylmethyl)-4-[4-(methylsulfanyl)phenoxy]pyridine

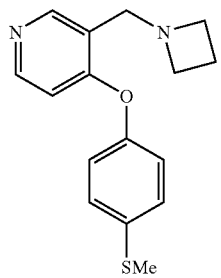

The product from Preparation 25 (500 mg, 2.04 mmol) was dissolved in DCM (5 mL) and treated with THF (5 mL), triethylamine (0.34 mL, 2.45 mmol), azetidine hydrochloride (229 mg, 2.45 mmol) and sodium triacetoxyborohydride (648 mg, 3.06 mmol). The mixture was then stirred for 18 h at room temperature. Sodium hydroxide 1M was added and the mixture was extracted with EtOAc. The organic extracts were dried (MgSO$_4$), and evaporated to a yellow oil. Purification by flash chromatography [SiO$_2$; DCM/MeOH/880 NH$_3$ (93:7:1)] afforded the title compound as a pale yellow oil which solidified on standing (275 mg, 47%); $\delta_H$ (CDCl$_3$, 300 MHz) 2.10 (2H, m), 2.46 (3H, s), 3.34 (4H, t), 3.73 (2H, d), 6.57 (1H, d), 7.00 (2H, d), 7.28 (2H, d), 8.28 (1H, d), 8.51 (1H, s); MS m/z (TS$^+$) 287 (MH$^+$).

EXAMPLE 102

N-Methyl-N-({4-[4-(methylsulfanyl)phenoxy]-1-oxido-3-pyridinyl}methyl)amine

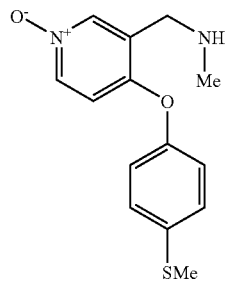

4-(Methylsulfanyl)phenol (400 mg, 2.86 mmol) was combined with the product from Preparation 3 (650 mg, 2.39 mmol) and K$_2$CO$_3$ (500 mg, 3.58 mmol) in DMF (5 mL) and the resulting mixture was heated at 90° C. for 23 h. Further batches of 4-(methylsulfanyl)phenol (200 mg, 1.43 mmol) and K$_2$CO$_3$ (250 mg, 1.79 mmol) were added and the mixture was heated for a further 3 days. After cooling to room temperature the mixture was partitioned between diethyl ether (300 mL) and 1M LiOH (100 mL), the organic layer was separated and the aqueous layer was re-extracted with diethyl ether (2×100 mL). The combined organic extracts were washed with water (5×100 mL), brine, dried (MgSO$_4$), and evaporated. The residue was purified by flash chromatography [SiO$_2$; DCM/MeOH/880 NH$_3$ (95:5:0.5)] to afford the desired product which was azeotroped with DCM (2×300 mL), and diethyl ether (3×100 mL) to afford the desired protected diphenylether as a white solid (510 mg, 57%); $\delta_H$ (CDCl$_3$, 300 MHz) 1.42 (9H, s), 2.48 (3H, s), 3.94 (3H, s), 4.50 (2H, brd), 6.59 (1H, d), 6.99 (2H, d), 7.31 (2H, d), 7.99 (1H, d), 8.13 (1H, s); MS m/z (TS$^+$) 377 (MH$^+$).

A solution of the protected diphenylether from above (460 mg, 1.22 mmol) was dissolved in DCM (150 mL) and the solution was cooled to 0° C. HCl gas was bubbled through the solution until saturated and the reaction was then stirred at room temperature for 1 h. The mixture was then evaporated to dryness, azeotroped with DCM (2×200 mL) and diethyl ether (2×100 mL) to give a white, hygroscopic solid (380 mg, 90%); Bis HCl salt: $\delta_H$ (CD$_3$OD, 300 MHz) 2.54 (3H, s), 2.88 (3H, s), 4.55 (2H, s), 7.20 (1H, d), 7.34 (2H, d), 7.47 (2H, d), 8.80 (1H, d), 9.15 (1H, s); MS m/z (TS$^+$) 277 (MH$^+$).

EXAMPLE 103

[4-(3,4-Dichlorophenoxy)-3-pyridinyl]-N-methyl-methanamine hydrochloride

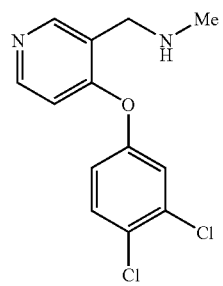

Methylamine (0.75 mL of 2.0 M solution in methanol, Aldrich Chemical Co, 1.5 mmol) in ethanol (4.0 mL) was stirred at room temperature under nitrogen until clear. Titanium (IV) isopropoxide (0.45 mL, 1.5 mmol) was then added via syringe, followed by the product from preparation 66 (0.2 g, 0.75 mmol) in ethanol (6 mL); this mixture was then stirred overnight. To the resulting solution was added sodium borohydride (43 mg, 1.1 mmol), and stirring was continued for an additional 2 h. The reaction was then quenched with 6M HCl (approximately 5 mL) and water (15 mL), the pH was adjusted to 10.0 with saturated aqueous Na$_2$CO$_3$ and stirred another 2 h before extracting with EtOAc. The EtOAc layer was combined with additional extracts of the water layer and the combined organic layers were washed with brine, dried with Na$_2$SO$_4$ and concentrated in vacuo to an oil, 0.188 g; $\delta_H$ (CDCl$_3$, 400 MHz) 2.51 (3H, s), 3.85 (2H, s), 7.01 (2H, m), 7.25 (1H, m), 7.44 (1H, dd), 7.72 (1H, d), 8.04 (1H, dd); MS m/z 283, 285 (MH$^{3o}$).

The oil was dissolved in anhydrous EtOAc and treated with 1 M HCl in Et$_2$O (1.2 mL) and then was stirred at room temperature, the resulting solid (0.188 g) was filtered and washed with Et$_2$O and dried under vacuum, m.p. 198–203° C.; Elemental analysis for C$_{13}$H$_{12}$Cl$_2$N$_2$O.HCl calculated: C, 48.85, H, 4.10, N, 8.76. Found: C, 48.97, H, 4.02, N, 8.60.

EXAMPLE 104

[2-(3,4-Dichlorophenoxy)-3-quinolinyl]-N-methyl-methanamine

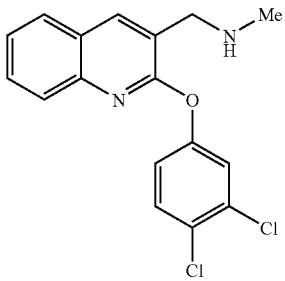

The title compound was prepared from the product from Preparation 67 by the method of example 103. HCl salt: m.p. 224–226° C.; Elemental analysis for $C_{17}H_{14}Cl_2N_2O\cdot HCl0.25H_2O$ calculated: C, 54.57, H, 4.18, N, 7.49; Found C, 54.70, H, 4.29, N 7.56; $\delta_H$ ($d_6$-DMSO, 400 MHz) 2.66 (3H, t), 4.37 (2H, t), 7.42 (1H, dd), 7.53 (1H, m), 7.67 (2H, m), 7.76 (2H, m), 7.95 (1H, d), 8.55 (1H, s), 9.24 (2H, br); MS m/z 333, 335 (MH+)

EXAMPLE 105

[2-(3,4-Dichlorophenoxy)-3-pyridinyl]-N-methyl-methanamine

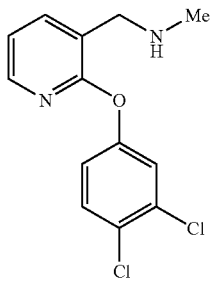

The title compound was prepared from the product from Preparation 65 by the method of Example 103. HCl salt; m.p. 198–203° C.; Elemental analysis for $C_{13}H_{12}Cl_2N_2O\cdot HCl$ calculated: C, 48.85, H, 4.10, N, 8.76; Found C, 48.97, H, 4.02, N, 8.60; $\delta_H$ ($d_6$-DMSO, 400 MHz) 2.65 (3H, s), 4.20 (2H, s), 7.05 (1H, s), 7.19 (1H, m), 7.45 (2H, m), 8.06 (1H, s), 8.13 (1H, s), 9.87 (1H, s); MS m/z 283, 285 (MH+)

EXAMPLE 106

[2-(4-Chlorophenoxy)-3-pyridinyl]-N,N-dimethyl-methanamine hydrochloride

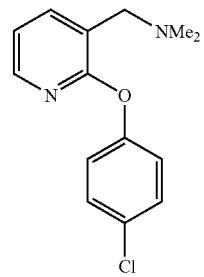

The product from Preparation 68 (0.43 g, 1.55 mmol) in anhydrous THF (20 mL) was stirred under nitrogen at room temperature until clear. Borane-THF complex (4.8 mL of a 1.0 M solution (Aldrich Chemical Co); 4.82 mmol.) was added and the mixture was heated at reflux for 18 h. Additional borane-THF complex (2.4 mL) was added, heating was continued another 8 h and then the mixture was allowed to cool to room temperature overnight. After concentrating the volume to one-half, 6.0 mL of 6N HCl was added and the reaction was heated at reflux for 2 h. After cooling to 25° C., the solution was diluted with water and EtOAc, and made basic with aqueous $Na_2CO_3$. The aqueous layer was extracted with additional EtOAc and the combined organic layers were washed with brine, dried ($MgSO_4$), filtered and concentrated in vacuo to a clear oil, 0.91 g. Chromatography on silica gel (230–400 mesh) using a gradient system of 100% $CHCl_3$ to 95:5 $CHCl_3$:EtOH gave borane-complexed free base, 0.228 g. This oil was dissolved in $Et_2O$ and treated with 1.7 mL of 1.0 M HCl in $Et_2O$ and stirred under $N_2$ at room temperature for 2 h. The resulting granular solid was filtered, washed with fresh $Et_2O$ and dried to a white solid, 0.156 g; m.p. 195–197° C.; Elemental analysis calculated for $C_{14}H_{15}ClN_2O\cdot HCl$: C, 56.20, H, 5.39, N, 9.36. Found: C, 56.45, H, 5.63, N, 9.38; $\delta_H$ ($d_6$-DMSO, 400 MHz) 2.77 (6H, s), 4.37 (2H, br), 7.22 (3H, m), 7.46 (2H, m), 8.09 (1H, dd), 8.15 (1H, dd), 10.48 (1H, br); MS m/z 263, 265 (MH+).

EXAMPLE 107

Methyl 5-[(dimethylamino)methyl]-6-[4-(trifluoromethoxy)phenoxy]nicotinate

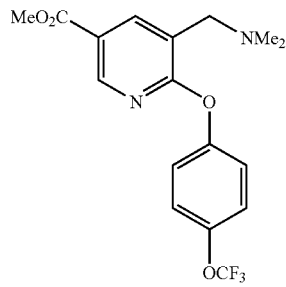

(i) Preparation of {5-Bromo-2-[4-(trifluoromethoxy)phenoxy]-3-pyridinl}-N,N-dimethylmethanamine BH$_3$.THF (1M soln in THF, 3.9 mL, 3.9 mmol) was added to a solution of the bromo compound of preparation 70 (320 mg, 0.79 mmol) in THF (10 mL) and the mixture was heated at 60° C. for 1 h. The mixture was cooled to room temperature, conc. HCl was added until pH 1 and the mixture was stirred for 5 min. The pH was adjusted to 10 with 2M NaOH and the mixture was extracted with EtOAc (3×). The combined organic extracts were washed with brine, dried (MgSO$_4$) and evaporated to give a gum. Purification by column chromatography [SiO$_2$; Pentane/Et$_2$O 2:1] gave {5-bromo-2-[4-(trifluoromethoxy)phenoxy]-3-pyridinyl}-N,N-dimethylmethanamine (205 mg) as a boron complex.

A mixture of the above boron complex (200 mg), Et$_3$N (200 µL, 1.4 mmol) and dichloro[1-1'-bis(diphenylphosphino)ferrocene]palladium (II) chloride dichloromethane adduct (40 mg, 0.05 mmol) in MeOH (15 mL) was heated at 100° C. under 200 psi pressure of CO for 3 h. The solvent was removed in vacuo and the residue was purified by column chromatography [SiO$_2$; Pentane/Et$_2$O 1:2] to give {5-bromo-2-[4-(trifluoromethoxy)phenoxy]-3-pyridinyl}-N,N-dimethylmethanamine (118 mg) as an oil; $\delta_H$ (CDCl$_3$, 400 MHz) 2.31 (6H, s), 3.55 (2H, s), 7.12 (2H, m), 7.23 (2H, m), 7.94 (1H, d), 8.07 (1H, d); MS m/z (TS$^+$) 391, 393 (MH$^+$).

(ii) Preparation of methyl 5-[(dimethylamino)methyl]-6-[4-(trifluoromethoxy)phenoxy]nicotinate A mixture of {5-bromo-2-[4-(trifluoromethoxy)phenoxy]-3-pyridinyl}-N,N-dimethylmethanamine (118 mg), Et$_3$N (200 µL, 1.4 mmol) and dichloro[1-1'-bis(diphenylphosphino)ferrocene]palladium (II) chloride dichloromethane adduct (40 mg, 0.05 mmol) in MeOH (12 mL) was heated at 120° C. under 400–600 psi pressure of CO for 5 h. The solvent was removed in vacuo and the residue was purified by column chromatography [SiO$_2$; Et$_2$O] to give the product ester (90 mg) as a colourless gum; $\delta_H$ (CDCl$_3$, 400 MHz) 2.35 (6H, s), 3.60 (2H, s), 3.92 (3H, s), 7.17 (2H, m), 7.26 (2H, m), 8.38 (1H, d), 8.66 (1H, d); MS m/z (TS$^+$) 371 (MH$^+$).

EXAMPLE 108

5-[(Dimethylamino)methyl]-6-[4-(trifluoromethoxy)phenoxy]nicotinamide

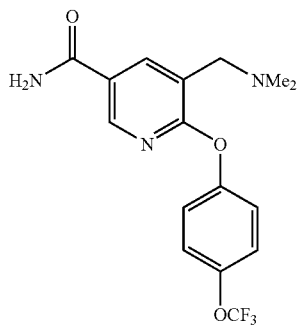

(i) Preparation of 5-[(dimethylamino)methyl]-6-[4-(trifluoromethoxy)phenoxy]-nicotinic acid 1M LiOH (1 mL, 1 mmol) was added to a solution of Example 107 (80 mg, 0.22 mmol) in MeOH (2 mL) and the mixture was heated at 70° C. for 2 h. The solvent was removed in vacuo, the residue was suspended in water and the pH was adjusted to 6 with 2M HCl. The resulting precipitate was collected by filtration and dried to give crude 5-[(dimethylamino)methyl]-6-[4-(trifluoromethoxy)phenoxy]-nicotinic acid (36 mg, 47%) which was used without further purification.

(ii) Preparation of 5-[(dimethylamino)methyl]-6-[4-(trifluoromethoxy)phenoxy]-nicotinamide N-N-Diisopropylethylamine (44 µL, 0.25 mmol), HOBt (20 mg, 0.15 mmol) and WSCDI (23 mg, 0.12 mmol) were added to the acid from step (i) (35 mg, 0.10 mmol) in CH$_2$Cl$_2$ (2 mL) and stirred for 30 min. (NH$_4$)$_2$CO$_3$ (19 mg, 0.20 mmol) was added and the mixture was stirred at room temperature for 16 h. The reaction mixture was partitioned between water (10 mL) and CH$_2$Cl$_2$ (10 mL) and the organic layer was dried (MgSO$_4$) and evaporated. The residue was purified by column chromatography [SiO$_2$; DCM/MeOH/880 NH$_3$ (93:7:1)] and then triturated with Et$_2$O to give the desired product (20 mg, 57%) as a white solid; $\delta_H$ (CDCl$_3$, 400 MHz) 2.35 (6H, s), 3.62 (2H, s), 5.66 (1H, br), 6.00 (1H, br), 7.18 (2H, m), 7.26 (2H, m), 8.23 (1H, d), 8.50 (1H, d); MS m/z (TS$^+$) 356 (MH$^+$).

PREPARATIONS

Preparation 1

4-Chloro-N,6-dimethylnicotinamide

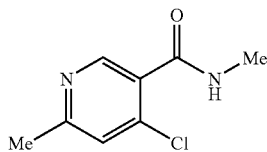

6-Methyl-4-oxo-1,4-dihydro-3-pyridinecarboxylic acid [see JP 57126477; M.
Mittelbach, *Synthesis* 1988, 479] (1.0 g, 6.56 mmol) was dissolved in DCM (32 mL) and treated sequentially with DMF (2 drops) and oxalyl chloride (2.86 mL, 32.8 mmol). The mixture was then stirred at room temperature for 24 h over which time it gradually turned dark blue. The solvents were evaporated and the residue was re-dissolved in DCM (30 mL). This solution was then added dropwise to cooled (0° C.) aqueous methylamine (40%, 10 mL) over 15 min. Stirring was maintained for 15 min at 0° C. then 1 h at room temperature. The reaction was diluted with water (25 mL) and extracted with DCM (3×25 mL). The combined organic fractions were dried (MgSO$_4$) and evaporated to a brown solid which was sufficiently pure for use without further purification (1.11 g, 92%); δ$_H$ (CDCl$_3$, 400 MHz) 2.38 (3H, s), 2.80 (3H, d), 7.01 (1H, s), 8.38 (1H, s); MS m/z (TS$^+$) 185 (MH$^+$).

Preparation 2

4-Chloro-6-methylnicotinamide

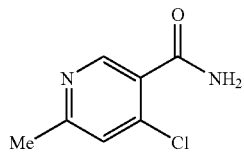

The title compound was prepared by the method of preparation 1 except that the initially formed acid chloride was poured into aqueous NH$_3$ instead of aqueous methylamine. After work up this gave the title amide (68%) as a brown solid; δ$_H$ (CDCl$_3$, 400 MHz) 2.57 (3H, s), 5.96 (1H, br), 6.37 (1H, br), 7.24 (1H, s), 8.92 (1H, s); MS m/z (TS$^+$) 171, 173 (MH$^+$).

Preparation 3 tert-Butyl (4-chloro-1-oxido-3-pyridinyl)methyl(methyl)carbamate

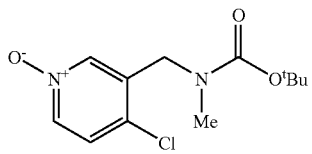

(i) Preparation of tert-butyl (4-chloro-3-pyridinyl)methyl(methyl)carbamate

4-Chloronicotinaldehyde [prepared according to D. Albanese, M. Penso, M. Zenoni, Synthesis 1999, 1294–1296] (1.0 g, 5.6 mmol) was dissolved in ethanol (50 mL) and methylamine in ethanol (8M, 16 mmol) was added, followed by titanium tetra(isopropoxide) (8 g, 28 mmol). The mixture was stirred at room temperature for 30 min and stored overnight in a freezer at −20° C. Sodium borohydride was then added and the mixture was allowed to reach room temperature. After 1 h the mixture set solid and was quenched cautiously by the addition of 3M hydrochloric acid (200 mL). The mixture was then allowed to stand for 30 min before neutralising to pH 7 with 3M NaOH solution. THF (200 mL) was added, followed by triethylamine (2.4 mL, 16.8 mmol) and di-tert-butyl dicarbonate (2.0 g, 9 mmol) and the resulting mixture was stirred rapidly at room temperature for 1 h. The mixture was then diluted with 2M NaOH (200 mL) and extracted with diethyl ether (3×200 mL). The combined organic fractions were washed with brine, dried (MgSO$_4$) and evaporated to an oily solid. The material was purified by flash chromatography twice; initially [SiO$_2$; DCM then 5% MeOH in DCM], then [SiO$_2$; EtOAc in pentane (20%)] to afford the desired compound as a colourless oil (1.12 g, 77%); δ$_H$ (CDCl$_3$, 300 MHz) 1.42 (9H, s), 2.98 (3H, s), 4.58 (2H, s), 7.29 (1H, d), 8.40 (1H, d), 8.43 (1H, s); MS m/z (TS$^+$) 256, 258 (MH$^+$).

(ii) Preparation of tert-butyl (4-chloro-1-oxido-3-pyridinyl)methyl(methyl)-carbamate Phthalic anhydride (566 mg, 3.82 mmol) was dissolved in acetonitrile (10 mL) and treated with urea-hydrogen peroxide complex (360 mg, 3.82 mmol) and the suspension was stirred for 15 min. A portion of the Boc-derivative from stage (i) (890 mg, 3.48 mmol) was added and the suspension was stirred at room temperature for 20 h. The residue was partitioned between potassium carbonate solution (100 mL) and DCM (200 mL). The organic layer was separated and the aqueous layer was re-extracted with DCM (3×50 mL). The combined organic fractions were washed with brine, dried (MgSO$_4$) and evaporated to an oil. Purification by flash chromatography [SiO$_2$; DCM/MeOH/880 NH$_3$ (90:10:1)] afforded the title compound (680 mg, 72%); δ$_H$ (CDCl$_3$, 300 MHz) 1.42 (9H, s), 2.91 (3H, s), 4.44 (2H, s), 7.23 (1H, d), 8.00 (1H, d), 8.08 (1H, s); MS m/z (TS$^+$) 273 (MH$^+$).

Preparation 4

5-(Allyloxy)-3-methyl-2-sulfanylphenol

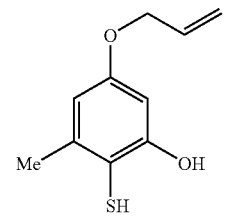

(i) Preparation of 6-hydroxy-4-methyl-1,3-benzoxathiol-2-one

Ammonium thiocyanate (10.71 g, 141 mmol) was added slowly to a solution of 5-methylresorcinol hydrate (5.0 g, 35 mmol) and copper(II) sulfate (17.56 g, 70 mmol) in water (100 mL), and the solution was stirred for 18 h. Diethyl ether (100 mL) was added and the mixture was filtered through Celite®, washing the cake with diethyl ether (100 mL). The diethyl ether layers were separated and the aqueous layer was re-extracted with diethyl ether (100 mL). The combined organic fractions were dried (MgSO$_4$) and evaporated to a yellow-orange solid (5.30 g, 83%). $^1$H NMR showed the material to be 80–90% pure and this was taken on without further purification; δ$_H$ (d$_6$-DMSO, 400 MHz) 2.30 (3H, s), 6.57 (1H, s), 6.65 (1H, s), 9.90 (1H, brs).

(ii) Preparation of 6-(allyloxy)-4-methyl-1,3-benzoxathiol-2-one

The thioxolone from stage (i) (5.30 g, 29 mmol) was dissolved in DMF (30 mL) and treated sequentially with potassium carbonate (4.15 g, 30 mmol) and allyl bromide (2.5 mL, 29 mmol). The resulting mixture was stirred at room temperature for 18 h. The mixture was then diluted with water (100 mL) and extracted with diethyl ether (2×50 mL). The combined extracts were dried (MgSO$_4$) and evaporated to a red/brown oil which was purified by flash chromatography [SiO$_2$; pentane/EtOAc (19:1 to 5:1)] to afford the desired allyl ether (2.95 g, 46%); δ$_H$ (CDCl$_3$, 400 MHz) 2.27 (3H, s), 4.49 (2H, d), 5.27 (1H, d), 5.36 (1H, d), 5.92–6.04 (1H, m), 6.63 (1H, s), 6.70 (1H, s).

(iii) Preparation of
5-(allyloxy)-3-methyl-2-sulfanylphenol

The allyl ether from stage (ii) (2.93 g, 13.2 mmol) was dissolved in THF (80 mL) and the solution was degassed by sparging with nitrogen for 1 h. 2M NaOH solution (previously sparged with nitrogen for 1 h) was added via syringe. The reaction mixture was stirred at room temperature for 3 h before being quenched by the addition of 2 M HCl to pH 2–3. The mixture was diluted with DCM (100 mL) and the organic layer was separated. The aqueous layer was re-extracted with DCM (50 mL) and the combined organic layers were dried (MgSO$_4$) and evaporated to a yellow oil (2.6 g, ca. quant.). $^1$H NMR showed the material to be 80–90% pure and this was taken on without further purification; δ$_H$ (CDCl$_3$, 400 MHz) 2.39 (3H, s), 2.42 (1H, s), 4.45 (2H, d), 5.23 (1H, d), 5.36 (1H, d), 5.94–6.03 (1H, m), 6.40 (2H, s); MS m/z (ES$^-$) 195 (M–H$^+$).

Preparation 5

5-Methyl-2,3-dihydro-1,4-benzoxathiin-7-ol

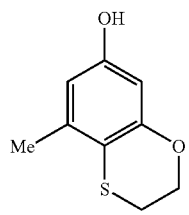

(i) Preparation of 7-(allyloxy)-5-methyl-2,3-dihydro-1,4-benzoxathiine

The product from Preparation 4 (1.70 g, 8.66 mmol) in solution in acetone (20 mL) was added dropwise by syringe pump over 4 h to a stirred mixture of 1,2-dibromoethane (746 µL, 8.66 mmol) and potassium carbonate (2.39 g, 17.32 mmol) in acetone (67 mL) and stirring was continued for a further 10 h. The solvents were evaporated and the residue was partitioned between water and EtOAc (50 mL each). The organic layer was separated and the aqueous layer was re-extracted with EtOAc (50 mL). The combined organic fractions were dried (MgSO$_4$) and evaporated to an oil. Purification by flash chromatography [SiO$_2$; pentane/EtOAc (9:1)] afforded the product as a brown oil (1.40 g, 73%); δ$_H$ (CDCl$_3$, 400 MHz) 2.16 (3H, s), 3.07 (2H, m), 4.34 (2H, m), 4.45 (2H, m), 5.23 (1H, d), 5.34 (1H, d), 5.93–6.03 (1H, m), 6.27 (1H, d), 6.39 (1H, d); MS m/z (TS$^+$) 223 (MH$^+$).

(ii) Preparation of
5-Methyl-2,3-dihydro-1,4-benzoxathiin-7-ol

The allyl ether from stage (i) (1.40 g, 6.3 mmol) was dissolved in THF (63 mL) and treated with sodium borohydride (1.19 g, 31.5 mmol) followed by palladium tetrakis(triphenylphosphine) (730 mg, 0.63 mmol), and the mixture was heated to 40° C. overnight. After cooling to room temperature the THF was evaporated and the residue was partitioned between 2M NaOH (25 mL) and diethyl ether (25 mL). The aqueous layer was separated and the organic layer re-extracted with 2M NaOH (25 mL). The combined aqueous layers were acidified with concentrated hydrochloric acid to pH 7–8 and extracted with EtOAc (2×25 mL). The combined organic extracts were dried (MgSO$_4$) and evaporated to a brown oil (10.73 g, 93%) of the desired title phenol; δ$_H$ (CDCl$_3$, 400 MHz) 2.17 (3H, s), 3.07 (2H, m), 4.33 (2H, m), 6.20 (1H, s), 6.31 (1H, s); MS m/z (TS$^+$) 183 (MH$^+$).

Preparation 6

3-Methoxy-5-methyl-4-(methylsulfanyl)phenol

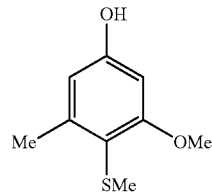

(i) Preparation of 5-(allyloxy)-1-methoxy-3-methyl-2-(methylsulfanyl)benzene

The product from Preparation 4 (930 mg, 4.7 mmol) was dissolved in DMF and MeI (740 µL, 11.75 mL) was added followed by potassium carbonate (1.95 g, 14,1 mmol) and the mixture was stirred for 18 h. The reaction was then diluted with water (100 mL) and ether (100 mL). The organic layer was separated and the aqueous layer was re-extracted with ether (50 mL). The combined organic extracts were washed with brine and dried (MgSO$_4$) before evaporation to a yellow oil (850 mg, 81%), which was taken on without further purification; δ$_H$ (CDCl$_3$, 400 MHz) 2.20 (3H, s), 2.44 (3H, s), 3.82 (3H, s), 4.48 (1H, d), 5.26 (1H, d), 5.37 (1H, d), 5.94–6.05 (1H, m), 6.32 (1H, d), 6.38 (1H, d).

(ii) Preparation of
3-methoxy-5-methyl-4-(methylsulfanyl)phenol

The allyl ether from stage (i) (850 mg, 3.8 mmol) was dissolved in THF (38 mL) and treated with palladium tetrakis(triphenylphosphine) (440 mg, 0.38 mmol) and sodium borohydride (719 mg, 19 mmol). The reaction mixture was then heated to 45° C. for 18 h. After cooling to room temperature most of the THF was evaporated and the residue was partitioned between 2M NaOH (25 mL) and diethyl ether (25 mL). The aqueous layer was separated and the organic layer was re-extracted with 2M NaOH (25 mL). The combined aqueous layers were neutralised to pH 7–8 with concentrated HCl and extracted with EtOAc (2×25 mL). The combined organic extracts were dried (MgSO$_4$) and evaporated to an orange solid of the title phenol (530 mg, 76%); δ$_H$ (CDCl$_3$, 400 MHz) 2.20 (3H, s), 2.41 (3H, s), 3.83 (3H, s), 6.26 (1H, s), 6.29 (1H, s); MS m/z (ES$^-$) 183 (M–H$^+$).

Preparation 7

3-Chloro-4-(methylsulfanyl)phenol

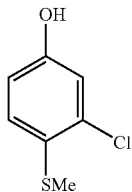

(i) Preparation of 2-chloro-1-(methylsulfanyl)-4-nitrobenzene

To a solution of 4-fluoro-3-chloronitrobenzene (27 g, 156 mmol) in DMF (150 mL) at room temperature was added 5-tert-butyl-4-hydroxy-2-methylphenyl sulfide (100 mg) followed by sodium thiomethoxide (NaSMe) (10 g, 143 mmol) and the reaction was stirred for 6 h. The DMF was removed in vacuo and the residue was partitioned between ether (1 L) and water (1 L). The ether layer was washed with water (1 L) and brine (1 L), dried (MgSO$_4$) and the solvent was removed under reduced pressure. The residue was purified by column chromatography (SiO$_2$; DCM: pentane 1:5 increasing polarity to 3:7) to give the title compound (15.22 g, 49%) as a yellow solid; $\delta_H$ (400 MHz, CDCl$_3$) 2.53 (3H, s), 7.20 (1H, d), 8.09 (1H, dd), 8.20 (1H, d).

(ii) Preparation of 3-chloro-4-(methylsulfanyl)aniline

To a mixture of the compound from stage (i) (14.08 g, 69 mmol) in acetic acid (300 mL) and water (60 mL) was added Fe powder (23 g, 412 mmol) and the reaction mixture was swirled until all the starting material had dissolved. The mixture was left to stand for 1.5 h and the acetic acid was then removed under reduced pressure. The residue was taken up in sat NaHCO$_3$ (aq) (500 mL) and EtOAc (500 mL) and filtered through Arbacel®. The layers were separated, the aqueous phase was extracted with EtOAc (300 mL) and the combined organics were washed with brine, dried (MgSO$_4$) and the solvent was removed in vacuo to give the title compound (11.52 g, 96%) as a beige solid; $\delta_H$ (400 MHz, CDCl$_3$) 2.38 (3H, s), 3.66 (2H, br), 6.53 (1H, dd), 6.70 (1H, d), 7.12 (1H, d); MS m/z (ES$^+$) 174 (MH$^+$).

(iii) Preparation of 3-chloro-4-(methylsulfanyl)phenol

The product from stage (ii) (11.5 g, 66.2 mmol) was dissolved in the minimum THF (~15 mL) and water (500 mL) was added with vigorous stirring, followed by conc H$_2$SO$_4$ (25 mL). The mixture was cooled in an ice-water bath and a solution of NaNO$_2$ (5.0 g, 72.5 mmol) in iced water (10 mL), was added via pipette under the surface of the reaction mixture. The reaction was stirred at 0° C. for 1.5 h and the resulting yellow/brown solution was decanted from the remaining solid into a dropping funnel containing ice (~200 g). This solution was added at a steady rate over 7 min to a vigorously stirred mixture of Cu(NO$_3$)$_2$ (230 g, 0.99 mol) and Cu$_2$O (8.52 g, 67.4 mmol) in water (1 L) at room temperature. After the addition was complete the mixture was stirred for a further 15 min before being extracted with ether (500 mL). The residual red/brown solid in the reaction flask was taken up in MeOH (100 mL) and diluted with ether (300 mL) before being poured into the aqueous layer from above. The ether layer was separated and the combined organic layers were extracted with 1M NaOH (3×100 mL). The aqueous extracts were acidified with conc. HCl and then extracted with ether (2×150 mL). The ether layers were then washed with brine, dried (MgSO$_4$) and the solvent was removed in vacuo to give the phenol (5.465 g, 47%) as a brown crystalline solid; $\delta_H$ (400 MHz, CDCl$_3$) 2.44 (3H, s), 5.08 (1H, br), 6.77 (1H, d), 6.93 (1H, d), 7.18 (1H, d); MS m/z (ES$^-$) 173 (M–H$^+$).

Preparation 8

3-Fluoro-4-(methylsulfanyl)phenol

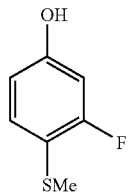

The title compound was prepared using a similar method to that described for Preparation 7 starting from commercially available 3,4-difluoronitrobenzene; $\delta_H$ (CDCl$_3$, 300 MHz) 2.40 (3H, s), 5.03 (1H, br), 6.60 (2H, m), 7.27 (1H, m obscured); MS m/z (ES$^-$) 157 (M–H$^+$).

Preparation 9

2,3-Dihydro-1,4-benzoxathiin-6-ol

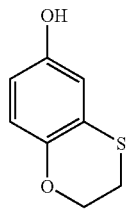

1,2-Dibromoethane (2.3 mL, 26.7 mmol) and K$_2$CO$_3$ (8.21 g, 59.4 mmol) were slurried in acetone (250 mL) and a solution of 2-sulfanyl-1,4-benzenediol (prepared according to *J. Org. Chem.* 1990, 55, 2736) (4.22 g, 29.7 mmol) in acetone (50 mL) was added over 4 h to the stirred mixture. Once the addition was complete stirring was continued for a further 10 h before the solvent was removed in vacuo. The residue was partitioned between water (50 mL) and EtOAc (50 mL), the aqueous layer was extracted with EtOAc (50 mL) and the combined organic layers were dried (MgSO$_4$) and evaporated. Purification of the residue by column chromatography [SiO$_2$; 9:1 (pentane/EtOAc)] gave the title compound (2.48 g, 55%) as a pale orange oil; $\delta_H$ (CDCl$_3$, 400 MHz) 3.08 (2H, m), 4.31 (2H, m), 4.44 (1H, s), 6.42 (1H, d), 6.49 (1H, s), 6.66 (1H, d); MS m/z (ES$^-$) 167 (M–H$^+$).

Preparation 10

2,3-Dihydro-1,4-benzoxathiin-7-ol

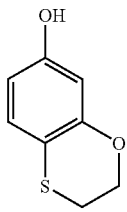

The title compound was prepared in a similar manner to Preparation 9 starting from 4-sulfanyl-1,3-benzenediol (prepared according to *J. Org. Chem.* 1979, 26, 4971–4973); $\delta_H$ (CDCl$_3$, 400 MHz) 3.05 (2H, t), 4.37 (2H, t), 6.32 (1H, s), 6.35 (1H, d), 6.84 (1H, d); MS m/z (TS$^+$) 169 (MH$^+$).

Preparation 11

1,3-Dihydro-2-benzothiophen-5-ol

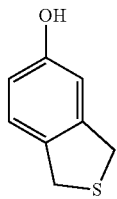

(i) Preparation of [4-(allyloxy)-2-(hydroxymethyl)phenyl]methanol

Dimethyl 4-(allyloxy)phthalate [prepared according to Inouye, M.; Tsuchiya, K.; Kitao, T. *Angew. Chem.* 1992, 104, 198–200 (See also *Angew. Chem., Int. Ed. Engl.*, 1992, 204–205)] (9.9 g, 38 mmol) was dissolved in THF (40 mL) and cooled to 0° C. before the dropwise addition of lithium aluminium hydride (1M in THF, 77 mL, 77 mmol) over 10 min. The mixture was then allowed to stir at room temperature for 3 h before being quenched cautiously by the addition of water (1.4 mL) followed by 2M NaOH (1.4 mL). Excess MgSO$_4$ was then added followed by water until a granular precipitate formed (ca. 5 mL). The mixture was then filtered and evaporated to a brown oil (7.1 g, ca. 95%). $^1$H NMR showed the material to be of ca. 85% purity. It was used directly in the next stage without further purification; $\delta_H$ (CDCl$_3$, 400 MHz) 2.63 (1H, brs), 2.91 (1H, brs), 4.52 (2H, m), 4.67 (4H, m), 5.26 (1H, dd), 5.38 (1H, dd), 5.97–6.09 (1H, m), 6.80 (1H, dd), 6.92 (1H, d), 7.22 (1H, d).

(ii) Preparation of 5-(allyloxy)-1,3-dihydro-2-benzothiophene

Crude diol from stage (i) (3.5 g, 18 mmol) was dissolved in DCM (60 mL) and treated with Et$_3$N (10 mL, 72 mmol) and the solution was cooled to 0° C.

Methanesulfonyl chloride (4.2 mL, 54 mmol) was added dropwise and the solution was stirred for 1 h being allowed to reach room temperature. The reaction was then quenched by the addition of water followed by 2M HCl (50 mL). The DCM layer was separated and the aqueous layer was re-extracted with DCM (50 mL). The combined organic fractions were washed with water (50 mL), dried (MgSO$_4$) and concentrated to a volume of ca. 30 mL. Benzyltriethylammonium chloride (1 g) was added followed by a solution of sodium sulfide (5 g, 91 mmol) in water (50 mL). The mixture was stirred rapidly under a nitrogen atmosphere for 15 h. The organic layer was separated and the aqueous layer was re-extracted with DCM (50 mL). The combined organic layers were dried (MgSO$_4$) and evaporated to a yellow oil. Flash chromatography afforded two fractions; the first was pure product and the second contained product contaminated with dimeric material. Trituration of the second fraction with pentane caused crystallisation of the dimeric material which was removed by filtration. The filtrate was combined with the first chromatography fraction to afford the desired product (800 mg, 23%); $\delta_H$ (CDCl$_3$, 400 MHz) 4.16 (2H, s), 4.19 (2H, s), 4.48 (2H, m), 5.26 (1H, d), 5.37 (1H, d), 5.95–6.06 (1H, m), 6.74 (2H, m), 7.09 (1H, d).

(iii) Preparation of 1,3-dihydro-2-benzothiophen-5-ol

The allyl ether from stage (ii) (800 mg, 4.16 mmol) was dissolved in THF (10 mL) and treated with palladium tetrakis(triphenylphosphine) (481 mg, 0.42 mmol) followed by sodium borohydride (944 mg, 25 mmol). The mixture was then heated to 45° C. and stirred at this temperature for 15 h. After cooling to room temperature the THF was evaporated and the residue partitioned between 2M NaOH solution (25 mL) and diethyl ether (25 mL). The aqueous layer was separated and the organic layer re-extracted with 2M NaOH solution (25 mL). The combined aqueous layers were neutralised to pH 7–8 with concentrated hydrochloric acid and extracted with EtOAc (2×25 mL). The combined organic extracts were dried (MgSO$_4$) and evaporated to a clear oil of the title phenol which solidified upon standing (540 mg, 85%); 4.14 (2H, s), 4.17 (2H, s), 6.63–6.68 (2H, m), 7.04 (1H, d)

Preparation 12

4-(Methylsulfanyl)-3-(trifluoromethyl)phenol

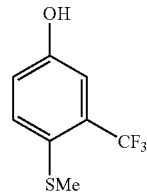

(i) Sulfide formation: 1-(methylsulfanyl)-4-nitro-2-(trifluoromethyl)benzene 2-Fluoro-5-nitrobenzotrifluoride (30 mL, 218 mmol) was dissolved in DMF (218 mL) and treated with 4,4'-thiobis-(6-tert-butyl-meta-cresol) (150 mg, 0.4 mmol) then sodium methanethiolate (15 g, 214 mmol). The reaction mixture was stirred at room temperature overnight, after which time it was evaporated to a low volume. The residue was partitioned between diethyl ether and water (1000 mL each). The organic fraction was washed sequentially with water and brine (750 ml each), dried (MgSO$_4$) and evaporated to a yellow oil. Purification by flash chromatography [SiO$_2$; EtOAc/pentane (5:95→10:90)] afforded a mixture of two compounds which was further purified by flash chromatography [SiO$_2$; DCM/pentane (10:90→40:60)] to afford the title sulfide (7.96 g, 15%); $\delta_H$ (CDCl$_3$, 400 MHz) 2.58 (3H, s), 7.39 (1 h, d), 8.28 (1H, dd), 8.46 (1H, d).

(ii) Nitro reduction:
4-(methylsulfanyl)-3-(trifluoromethyl)aniline

A suspension of the sulfide from stage (i) in acetic acid (168 mL) and water (25 mL) was treated with iron powder (11.25 g, 201 mmol). The mixture was stirred at room temperature for 2 hours before being evaporated to a small volume. The residue was partitioned between saturated NaHCO$_{3(aq)}$ and EtOAc (200 mL each) then filtered through a plug of Arbacele®. The organic layer was separated and the aqueous layer was re-extracted with EtOAc (2×100 mL). The combined organic layers were dried (MgSO$_4$) and evaporated to a brown oil of the title aniline slightly contaminated with acetic acid (8 g ca. 100%); $\delta_H$ (CDCl$_3$, 400 MHz) 2.40 (3H, s), 6.77 (1H, dd), 6.95 (1H, d), 7.32 (1H, d).

(iii) Diazonium salt formation/hydrolysis:
4-(methylsulfanyl)-3-(trifluoromethyl)phenol A suspension of the aniline from stage (ii) (8.00 g, 38.2 mmol) in water was treated with conc. sulfuric acid (20 mL) and cooled to 0° C. with vigorous stirring. A solution of sodium nitrite (2.9 g, 42.1 mmol) in water (15 mL) was added dropwise, and upon completion of the addition the mixture was stirred at this temperature for a further 30 min by which time dissolution had occurred. A solution of copper(II) nitrate hemipentahydrate (120 g, 516 mmol) in water (900 mL) was added followed by solid copper(I) oxide (4.9 g, 34.4 mmol). Vigorous stirring was continued until nitrogen evolution subsided (10–15 min). The reaction mixture was extracted with diethyl ether (2×400 mL) and the combined organics were extracted with 1M NaOH (3×100 mL). The combined NaOH fractions were acidified to pH 2 with conc. HCl, and extracted with diethyl ether (2×150 mL). The combined organic fractions were washed with brine, dried (MgSO$_4$) and evaporated to a brown oil (3.5 g, 44%): $\delta_H$ (CDCl$_3$, 400 MHz) 2.44 (3H, s), 5.50 (1H, brs), 6.97 (1H, dd), 7.16 (1H, d), 7.38 (1H, d); MS m/z (ES$^-$) 207 (M−H$^+$).

Preparation 13

3-Methoxy-4-(methylsulfanyl)phenol

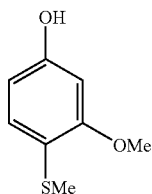

(i) Formation of benzylether:
6-(benzyloxy)-1,3-benzoxathiol-2-one

6-Hydroxy-1,3-benzoxathiol-2-one (50 g, 297 mmol) was dissolved in DMF (500 mL), and treated with benzyl bromide (53 mL, 446 mmol) and potassium carbonate (82 g, 595 mmol). The mixture was heated at 60° C. under a nitrogen atmosphere overnight before being evaporated to dryness. The residue was partitioned between diethyl ether (700 mL) and water (400 mL) and the organic layer was separated. The aqueous layer was re-extracted with diethyl ether (2×800 mL) and the combined organic fractions were washed with water (2×500 mL), dried (MgSO$_4$), and evaporated to a yellow oil. Purification by flash chromatography [SiO$_2$; EtOAc/pentane (1:19→1:9)] gave a gummy white solid which was triturated with Et$_2$O/pentane to give a white solid of the desired benzylether (17.65 g, 23%); $\delta_H$ (CDCl$_3$, 300 MHz) 5.10 (2H, s), 6.92 (1H, d), 6.98 (1H, s), 7.28 (1H, d), 7.35–7.45 (5H, m); MS m/z (TS$^+$) 276 (MNH$_4{}^+$).

(ii) Hydrolysis of the Thioxolone Ring:
5-(benzyloxy)-2-sulfanylphenol

The benzylether from step (i) (17.55 g, 67.9 mmol) was dissolved in THF (125 mL) and treated with aqueous sodium hydroxide (2M; 125 mL). After stirring at room temperature for 2 hours the mixture was evaporated to remove THF and the remaining aqueous solution was washed with diethyl ether (3×100 mL). The aqueous layer was then acidified with conc. HCl to pH 1 causing the mixture to effervesce. The mixture was then extracted with diethyl ether (3×100 mL) and the combined extracts were washed with brine (100 mL), dried (MgSO$_4$) and evaporated to a yellow oil (13.65 g, 86%); $\delta_H$ (CDCl$_3$, 300 MHz) 5.08 (2H, s), 6.40 (1H, s), 6.55 (1H, d), 6.63 (1H, s), 7.30–7.45 (5H, m); MS m/z (TS$^+$) 250 (MNH$_4{}^+$).

(iii) Methylation of the Phenol and Thiophenol:
4-(benzyloxy)-2-methoxy-1-(methylsulfanyl)benzene A mixture of the thiophenol-phenol from stage (ii) (13.5 g, 58.1 mmol) and potassium carbonate (9.64 g, 69.7 mmol) in DMF (150 mL) at 0° C. was treated with methyl iodide (7.97 mL, 128 mmol). The mixture was allowed to reach room temperature and stirred for 3 days. The reaction was evaporated to dryness and the residue was partitioned between water (150 mL) and diethyl ether (150 mL). The aqueous layer was removed and extracted further with diethyl ether (2×75 mL), the combined organic layers were washed with water (2×50 mL), brine (50 mL), dried (MgSO$_4$) and evaporated to a yellow oil. Purification by flash chromatography [SiO$_2$; EtOAc in pentane (2% →4%)] afforded an oil which solidified to a white solid after drying under vacuum (11.5 g, 65%); $\delta_H$ (CDCl$_3$, 300 MHz) 2.40 (3H, s), 3.90 (3H, s), 5.08 (2H, s), 6.57 (2H, s), 7.20 (1H, dd), 7.35–7.45 (5H, m); MS m/z (TS$^+$) 261 (MH$^+$).

(iv) Cleavage of the Benzylether:
3-methoxy-4-(methylsulfanyl)phenol

The benzylether from stage (iii) (9.27 g, 39.5 mmol) was dissolved in DCM (5 mL), ethanethiol (5 mL) and BF$_3$.OEt$_2$ (5 mL, 39.5 mol) were then added at room temperature under a nitrogen atmosphere. The mixture was stirred overnight before the reaction was quenched with 2M HCl and stirred for a further 30 min. The mixture was then basified by the addition of 2M NaOH until pH 10 was attained. The mixture was then washed with EtOAc (3×50 mL). The aqueous layer was re-acidified by the addition of 2M HCl to pH 1 and extracted with EtOAc (4×50 mL). The extracts were combined, dried (MgSO$_4$) and evaporated to an oil. Purification by flash chromatography [SiO$_2$; EtOAc/pentane (1:9→1:4)] afforded the desired phenol compound as a colourless solid (1.73 g, 28%); $\delta_H$ (CDCl$_3$, 400 MHz) 2.21 (3H, s), 3.70 (3H, s), 6.30 (1H, d), 6.35 (1H, s), 6.96 (1H, d), 9.39 (1H, brs).

Preparation 14

4-Methoxy-3-(methylsulfanyl)phenol

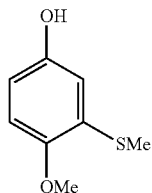

(i) Formation of Allylether:
5-(allyloxy)-1,3-benzoxathiol-2-one

5-Hydroxy-1,3-benzoxathiol-2-one (2 g, 11.9 mmol) [prepared according to *J. Org. Chem.* 1990, 55, 27361] was dissolved in acetone (13 mL) and treated with potassium carbonate (3.29 g, 23.8 mmol) followed by allyl bromide (1.13 mL, 13.1 mmol). The mixture was then stirred under nitrogen atmosphere for 24 h. The reaction mixture was evaporated to dryness and the residue was partitioned between water and diethyl ether (50 mL each). The organic fraction was separated and the aqueous layer was re-extracted with diethyl ether (50 mL). The combined organic fractions were dried (MgSO$_4$) and evaporated to a brown oil. Purification by flash chromatography [SiO$_2$; pentane/EtOAc (95:5→90:10)] afforded the desired compound as a colourless oil (1.9 g, 77%); $\delta_H$ (CDCl$_3$, 400 MHz) 4.50 (2H, d), 5.28 (1H, d), 5.38 (1H, d), 6.00 (1H, ddt), 6.83 (1H, dd), 6.91 (1H, d), 7.15 (1H, d).

(ii) Hydrolysis of the Thiocarbonate:
4-(allyloxy)-2-sulfanylphenol

The allyl ether from stage (i) (834 mg) was dissolved in degassed THF (5 mL) and treated with degassed aqueous sodium hydroxide (2M; 5 mL, 10 mmol). After stirring for 30 minutes the solution was acidified with 2M HCl to pH 1 causing the mixture to effervesce. The mixture was extracted with diethyl ether (2×30 mL) and the combined extracts were dried (MgSO$_4$) and evaporated to a clear oil which used directly in the next stage; $\delta_H$ (CDCl$_3$, 300 MHz) 3.13 (1H, s), 4.49 (2H, d), 5.30 (1H, d), 5.44 (1H, dt), 5.76 (1H, s), 5.97–6.12 (1H, m), 6.79–6.96 (2H, m), 7.16–7.25 (1H, m).

(iii) Methylation of the Phenol and Thiophenol:
4-(allyloxy)-1-methoxy-2-(methylsulfanyl)benzene The thiophenol from stage (ii) was added as a solution in acetone (4 mL) to a slurry of potassium carbonate (1.66 g, 12 mmol) in acetone (4 mL) and methyl iodide (623 μL, 10 mmol). The mixture was stirred at room temperature overnight and then evaporated to a gummy solid. This residue was partitioned between diethyl ether and water (50 mL each) and the organic layer was separated. The aqueous layer was re-extracted with diethyl ether (50 mL) and the combined organic fractions were dried (MgSO$_4$) and evaporated to an oil. Purification by flash chromatography [SiO$_2$, pentane/EtOAc (19:1→10:1)] afforded the title ally ether as an oil (556 mg, 66%); $\delta_H$ (CDCl$_3$, 400 MHz) 2.38 (3H, s), 3.81 (3H, s), 4.44 (2H, d), 5.23 (1H, d), 5.36 (1H, d), 6.00 (1H, ddt), 6.61 (1H, d), 6.69–6.72 (2H, m).

(iv) Deallylation of Allylether:
4-methoxy-3-(methylsulfanyl)phenol

The allyl ether from stage (iii) (556 mg, 2.64 mmol) was dissolved in dry THF (26 mL) together with palladium tetrakis(triphenylphosphine) (153 mg, 0.13 mmol) and the mixture was cooled to 0° C. Sodium borohydride (600 mg, 15.9 mmol) was added and the mixture was allowed to reach room temperature and stirred overnight. The reaction had proceeded to ca. 50% conversion as judged by TLC analysis and so a further batch of palladium tetrakis(triphenylphosphine) (153 mg, 0.13 mmol) was added and the mixture was warmed to 45° C. and stirred for a further 12 h. The reaction was quenched by the cautious addition of sat. NH$_4$Cl$_{(aq)}$ (until effervescence ceased) and the resulting mixture was extracted with EtOAc (3×50 mL). The combined extracts were dried (MgSO$_4$) and evaporated to a yellow-orange oil. Purification by flash chromatography [SiO$_2$; DCM/MeOH/ 880 NH$_3$ (93:7:1)] afforded the desired title phenol as a colourless oil (425 mg, 90%); $\delta_H$ (CDCl$_3$, 400 MHz) 2.39 (3H, s), 3.83 (3H, s), 4.97 (1H, s), 6.57 (1H, dd), 6.67 (1H, S), 6.68 (1H, d).

Preparation 15

2.3-Dihydro-1-benzothiophen-6-ol

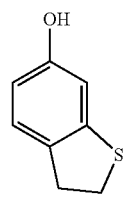

(i) Preparation of 2,3-dihydro-1-benzothiophen-6-ol 1,1-dioxide

A suspension of 2,3-dihydro-1-benzothiophen-6-amine 1,1-dioxide [prepared according to *J. Am. Chem. Soc.* 1955, 77, 5939] (15.73 g, 85.8 mmol) in water (500 mL) and conc. H$_2$SO$_4$ (35 mL) was warmed until solution was achieved. The mixture was cooled to 0° C. and a solution of NaNO$_2$ (6.22 g, 90 mmol) in water (15 mL) was then added over 5 min. The reaction was stirred at 0° C. for 1 h then urea was added, to remove excess nitrite, until a negative test with starch/KI paper was obtained. The mixture was allowed to warm to room temperature then added with stirring to a mixture of conc. $H_2SO_4$ (55 mL) and water (750 mL) at 90° C. The reaction was re-heated to 90° C. and stirred at this temperature for 30 min. The hot reaction mixture was filtered through Arbacel® then stirred at room temperature overnight. The aqueous mixture was extracted with ether (2.5 L) and then EtOAc (5×500 mL) and the combined organic layers were dried (MgSO4) and evaporated to give the desired phenol (12.7 g, 80%) which was used without further purification; $\delta_H$ (CDCl$_3$, 400 MHz) 3.30 (2H, m), 3.50 (2H, m), 7.05 (1H, m), 7.14 (1H, s), 7.23 (1H, m); MS m/z (ES⁻) 183 (M–H⁺).

(ii) Preparation of
2,3-dihydro-1-benzothiophen-6-ol

A solution of the sulfone from stage (i) (4.84 g, 26.3 mmol) in toluene (100 mL) and THF (70 mL) was added to a solution of DIBAL in toluene (1M, 100 mL, 100 mmol) and the mixture was then heated at reflux for 16 h. After cooling to room temperature EtOH (75 mL) was added cautiously followed by water (100 mL) with stirring. 6M HCl was added to the resulting thick suspension and the organic layer was separated. The aqueous layer was extracted with EtOAc (3×150 mL) and the combined organic layers were dried (MgSO$_4$) and evaporated to a beige solid. Purification by column chromatography [SiO$_2$; DCM/MeOH/880 NH$_3$ (97:3:0.25) increasing polarity to (95:5:0.5)] afforded the desired title phenol as a beige solid (1.85 g, 53%); $\delta_H$ (CD$_3$OD, 400 MHz) 3.13 (2H, t), 3.30 (2H, m), 6.41 (1H, d), 6.60 (1H, s), 6.98 (1H, d); MS m/z (ES⁻) 151 (M–H⁺).

Preparation 16

4-Ethyl-3-(methylsulfanyl)phenol

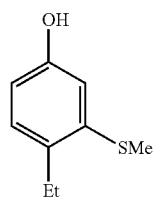

(i) Preparation of 2-bromo-5-methoxyaniline

4-Bromo-3-nitroanisole (10 g, 43 mmol) and iron powder (21.72 g, 385 mmol) were stirred in a mixture of water (10 mL) and acetic acid (100 mL) for 1.5 h. The solvent was removed in vacuo, the brown residue was taken up in water (200 mL) and treated with 10% aq K$_2$CO$_3$ until pH 10. The mixture was extracted with EtOAc (4×150 mL) and the combined organic extracts were dried (MgSO4) and evaporated to give the desired aniline (5.0 g, 57%) as a brown oil; $\delta_H$ (CDCl$_3$, 400 MHz) 3.72 (3H, s), 4.05 (2H, br), 6.22 (1H, dd), 6.32 (1H, d), 7.26 (1H, d); MS m/z (TS⁺) 202, 204 (MH⁺).

(ii) Preparation of
1-bromo-4-methoxy-2-(methylsulfanyl)benzene

The preceding aniline (16.4 g, 81 mmol) was taken up in THF (5 mL) 2M HCl (5 mL) and added slowly to vigorously stirred 2M HCl (150 mL) before being cooled to 0° C. A solution of NaNO$_2$ (5.6 g, 81 mmol) in water (25 mL) was then added dropwise and the mixture was stirred at 0° C. for 1 h. The mixture was transferred to a pressure-equalised dropping funnel and added dropwise to a vigorously stirred mixture of dimethyldisulfide (10.97 mL, 0.12 mol) and CuCl (16.07 g, 0.16 mol) in water (25 mL). Once the addition was complete the mixture was allowed to warm to room temperature and stirred overnight. The reaction mixture was filtered, the filtrate was extracted with EtOAc (3×150 mL) and the combined organic layers were dried (MgSO$_4$) and evaporated. The residue was purified by column chromatography [SiO$_2$; 5% EtOAc in pentane increasing polarity to 7.5%] to give the desired thioether (4.38 g, 23%) as an orange oil; $\delta_H$ (CDCl$_3$, 400 MHz) 2.44 (3H, s), 3.79 (3H, s), 6.55 (1H, d), 6.68 (1H, s), 7.39 (1H, d).

(iii) Preparation of
4-methoxy-2-(methylsulfanyl)-1-vinylbenzene

Triethylamine (0.49 mL, 3.52 mmol), tributyl(vinyl)tin (1.88 mL, 6.4 mmol) and Pd(PPh$_3$)$_4$ (372 mg, 0.32 mmol) were added to a solution of the preceding bromo compound (750 mg, 3.2 mmol) in toluene (15 mL) and the mixture was heated at reflux under nitrogen overnight. The solvent was removed in vacuo and the residue was partitioned between water (50 mL) and EtOAc (50 mL). The aqueous layer was extracted with EtOAc (50 mL) and the combined organic layers were dried (MgSO$_4$) and evaporated. Purification by column chromatography [SiO$_2$; 2% EtOAc in pentane] gave the desired alkene (650 mg) as a pale yellow oil contaminated with traces of tin residues; ($\delta_H$ (CDCl$_3$, 300 MHz) (Product peaks) 2.46 (3H, s), 3.83 (3H, s), 5.24 (1H, d), 5.60 (1H, d), 6.72 (1H, dd), 6.81 (1H, d), 7.06 (1H, dd), 7.44 (1H, d).

(iv) Preparation of
1-ethyl-4-methoxy-2-(methylsulfanyl)benzene

10% Pd on carbon (150 mg) was added to a solution of the preceding alkene (640 mg) in EtOH (30 mL) and the mixture was heated at 50° C. under 40 psi pressure of hydrogen overnight. The reaction mixture was filtered through Arbacel®, washing with EtOH and the CH$_2$Cl$_2$ and evaporated to give the product (614 mg) as a yellow oil containing trace impurities from the previous step; $\delta_H$ (CDCl$_3$, 400 MHz) (Product peaks) 1.20 (3H, t), 2.44 (3H, s), 2.65 (2H, q), 3.79 (3H, s), 6.64 (1H, d), 6.76 (1H, s), 7.06 (1H, d).

(v) Preparation of 4-ethyl-3-(methylsulfanyl)phenol

30% HBr in AcOH (2 mL) and conc hydrobromic acid (0.5 mL) were added to the ether from the preceding step (614 mg) and the mixture was heated at reflux overnight. The reaction mixture was cautiously diluted with water (50 mL) and extracted with Et$_2$O (4×30 mL). The combined organic layers were dried (MgSO4) and evaporated to give a black oil. Purification by column chromatography [SiO$_2$; 10% EtOAc in pentane] gave the title phenol (349 mg) as a reddish oil; $\delta_H$ (CDCl$_3$, 400 MHz) 1.21 (3H, t), 2.42 (3H, s), 2.63 (2H, q), 4.95 (1H, br), 6.56 (1H, dd), 6.67 (1H, d), 7.00 (1H, d); MS m/z (ES$^-$) 167 (M–H$^+$).

EXAMPLE 17

4-Chloro-3-(methylsulfanyl)phenol

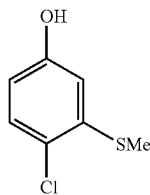

(i) Preparation of 1-chloro-4-methoxy-2-(methylsulfanyl)benzene

2-Chloro-5-methoxyaniline (13.83 g, 87.8 mmol) (prepared according to H. F. Faith, M. F. Bahler, H. J. Florestano, *J. Am. Chem. Soc.*, 1955, 77, 543) was dissolved in 2M HCl (160 mL) by heating to 50° C. and then cooled to 0° C. with stirring to produce a fine precipitate. A solution of NaNO$_2$ (6.66 g, 96.5 mmol) in water (60 mL) was then added dropwise and the mixture was stirred at 0° C. for 1 h. The reaction mixture was then transferred to a pressure equalized dropping funnel containing ice and added dropwise to a solution of NaSMe (12.3 g, 175 mmol) in water (352 mL) [Caution, this reaction can generate potentially explosive methylsulfanyldiazenes]. Mixture stirred overnight, then extracted with ether (2×500 mL) and the combined organic extracts were dried (MgSO$_4$) and evaporated. The residue was partitioned between ether (750 mL) and 2M NaOH (750 mL) and the organic phase was dried (MgSO4) and evaporated to give crude thioether (~80% pure) (13.22 g, 80%) as a brown oil which was used without further purification; $\delta_H$ (CDCl$_3$, 400 MHz) 2.41 (3H, s), 3.75 (3H, s), 6.58 (1H, dd), 6.67 (1H, d), 7.20 (1H, d).

(ii) Preparation of 4-Chloro-3-(methylsulfanyl)phenol

The preceding ether (13.22 g, 70 mmol) was dissolved in a mixture of conc. hydrobromic acid (9 mL) and 30% HBr in acetic acid (35 mL) and heated at reflux for 6 h. After cooling to room temperature and standing overnight the reaction wa diluted with water (500 mL) and extracted with EtOAc (500 mL). The organic layer was extracted with 2M NaOH (600 mL) then 6M NaOH (200 mL) and the combined basic extracts were acidified with conc. HCl before being extracted with EtOAc (1 L). The organic extract was dried (MgSO$_4$) and evaporated, dissolved in toluene (100 mL) and evaporated. The residue was purified by column chromatography [SiO$_2$; 5% EtOAc in pentane increasing polarity to 20%] to give the title phenol (2.2 g, 18%); $\delta_H$ (CDCl$_3$, 400 MHz) 2.41 (3H, s), 4.98 (1H, s), 6.52 (1H, dd), 6.62 (1H, d), 7.16 (1H, d); MS m/z (ES$^-$) 173 (M–H$^+$).

Preparation 18

4-[3-Methoxy-5-methyl-4-(methylsulfanyl)phenoxy]nicotinaldehyde

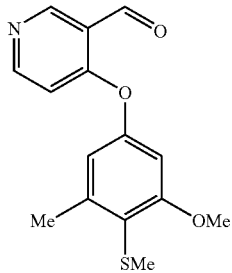

4-Chloronicotinaldehyde [prepared according to D. Albanese, M. Penso, M. Zenoni, *Synthesis* 1999, 1294–1296] (77 mg, 0.54 mmol), the phenol from preparation 6 (100 mg, 0.54 mmol) potassium carbonate (150 mg, 1.08 mmol), and DMF (0.5 mL) were combined and the mixture was heated together at 60° C. for 15 h. After cooling to room temperature the mixture was diluted with water 5 mL and extracted with diethyl ether (2×5 mL. The combined organic fractions were dried (MgSO$_4$) and evaporated to a brown oil of the title compound (150 mg, 95%). $^1$H NMR showed the material to be of sufficient purity (90–95%) to be used without further purification; $\delta_H$ (CDCl$_3$, 400 MHz) 2.29 (3H, s), 2.49 (3H, s), 3.85 (3H, s), 6.52 (1H, s), 6.61 (1H, s), 6.71 (1 h, d), 8.52 (1H, d), 8.96 (1H, s), 10.55 (1H, s); MS m/z (ES$^+$) 290 (MH$^+$).

Preparation 19–37

The following compounds of formula IIa, i.e. compounds of general formula II where L is —C(H)—, M is —N—, Q is —C(H)—, U is —C(H)— and T is CHO, were prepared in an analogous fashion to preparation 18 from 4-chloronicotinaldehyde and the phenol indicated. Unless otherwise stated, starting phenols are either commercially available or their preparations are described herein. The crude product was generally of sufficient purity to use in the next stage without further purification.

(IIa)

| Prep | Prec phenol | W | Y | Z | Data |
|---|---|---|---|---|---|
| 19 | commercially available | | 4-CF₃-phenyl | | δ_H(CDCl₃, 400MHz) 6.73(1H, d), 7.25(2H, d), 7.78(2H, d), 8.61 (1H, d), 9.07(1H, s), 10.59(1H, s); MS m/z(TS⁺)268(MH⁺) |
| 20 | commercially available | | 4-OCF₃-phenyl | | δ_H(CDCl₃, 400MHz) 6.67(1H, d), 7.20(2H, d), 7.35(2H, d), 8.58 (1H, d), 9.05(1H, s), 10.60(1H, s); MS m/z(TS⁺)284(MH⁺) |
| 21 | Ref^a | | 2,3-dihydrobenzothiophen-5-yl | | Used crude as a 75:25 mixture with starting aldehyde: δ_H(CDCl₃, 400MHz)3.31–3.34(2H, m), 3.43–3.50(2H, m), 6.70(1H, d), 6.91(1H, dd), 6.99(1H, s), 7.26 (1H, m), 8.52(1H, d), 8.98(1H, s), 10.60(1H, s); MS m/z(TS⁺) 258(MH⁺) |
| 22 | commercially available | | 3-Me, 4-SMe-phenyl | | δ_H(CDCl₃, 300MHz) 2.39(3H, s), 2.52(3H, s), 6.67(1H, d), 7.00 (2H, d+s), 7.25(1H, obs), 8.57 (1H, d), 9.01(1H, s), 10.62(1H, s); MS m/z(ES⁺)260(MH⁺) |
| 23 | Prep 8 | | 3-F, 4-SMe-phenyl | | Used crude as a 75:25 mixture with starting aldehyde: δ_H(CDCl₃, 400MHz) 2.47(3H, s), 6.69(1H, m), 6.91(2H, m), 7.35(1H, m), 8.57(1H, brs), 9.00(1H, brs), 10.55(1H, s); MS m/z(TS⁺)264 (MH⁺) |

-continued (IIa)

| Prep | Prec phenol | W | Y | Data |
|---|---|---|---|---|
| 24 | Prep 10 | (benzo-dioxin/thiane ring, S and O) | | δ$_H$(CDCl$_3$, 400MHz) 3.15(2H, m), 4.48(2H, m), 6.65(2H, m), 6.73(1H, m), 7.11(1H, m), 8.54 (1H, d), 8.99(1H, s), 10.57(1H, s); MS m/z(TS$^+$)274(MH$^+$) |
| 25 | commercially available | | SMe (para) | δ$_H$(CDCl$_3$, 300MHz) 2.50(3H, s), 6.65(1H, d), 7.08(2H, d), 7.36 (2H, d), 8.52(1H, d), 8.97(1H, s), 10.58(1H, s); MS m/z(TS$^+$)246 (MH$^+$) |
| 26 | Prep 12 | CF$_3$ | SMe | δ$_H$(CDCl$_3$, 400MHz) 2.53(3H, s), 6.63(1H, d), 7.26(1H, dd) 7.45 (2H, d), 8.58(1H, d), 9.01(1H, s), 10.57(1H, s); MS m/z(TS$^+$)314 (MH$^+$) |
| 27 | Prep 7 | Cl | SMe | δ$_H$(CDCl$_3$, 400MHz) 2.48(3H, s), 6.64(1H, d), 6.05(1H, d), 7.19 (1H, s), 7.28(1H, d), 8.57(1H, d), 8.99(1H, s), 10.56(1H, s); MS m/z(TS$^+$)280, 282(MH$^+$) |
| 28 | Prep 13 | OMe | SMe | δ$_H$(CDCl$_3$, 400MHz) 2.45(3H, s), 3.87(3H, s), 6.62(1H, d), 6.69 1H, d), 6.73(1H, dd), 7.20(1H, d), 8.53(1H, d), 8.99(1H, s), 10.58(1H, s); MS m/z(TS$^+$)276 (MH$^+$) |

-continued (IIa)

| Prep | Prec phenol | W, Y, Z (ring B) | Data |
|---|---|---|---|
| 29 | commercially available | 4-Et-phenyl | δ$_H$(CDCl$_3$, 400MHz) 1.23(3H, t), 2.67(2H, q), 6.62(1H, d), 7.04(2H, d), 7.22(2H, d), 8.47(1H, d), 8.96(1H, s); MS m/z(TS$^+$)228 (MH$^+$) |
| 30 | Prep 11 | 1,3-dihydrobenzo[c]thiophene | δ$_H$(CDCl$_3$, 400MHz) 4.25(4H, s), 6.63(1H, d), 6.96(1H, d), 7.00(1H, s), 7.29(1H, d), 8.51(1H, d), 8.97(1H, s), 10.57(1H, s) |
| 31 | Prep 5 | 8-Me-2,3-dihydro-benzo[1,4]oxathiine | δ$_H$(CDCl$_3$, 400MHz) 2.21(3H, s), 3.14(2H, m), 4.38(2H, m), 6.50(1H, d), 6.55(1H, d), 6.72(1H, d), 8.50(1H, d), 8.94(1H, s) |
| 32 | Prep 15 | 2,3-dihydrobenzo[b]thiophene | δ$_H$(CDCl$_3$, 400MHz) 3.32(2H, m), 3.44(2H, m), 6.71(1H, d), 6.77(1H, dd), 6.99(1H, s), 7.25(1H, d), 8.53(1H, d), 8.99(1H, s), 10.60(1H, s); MS m/z(ES$^+$)258 (MH$^+$) |
| 33 | Prep 9 | 2,3-dihydro-benzo[1,4]oxathiine | δ$_H$(CDCl$_3$, 400MHz) 3.17(2H, m), 4.45(2H, m), 6.69(1H, d), 6.77(1H, d), 6.89(2H, m), 8.56(1H, d), 8.99(1H, s), 10.59(1H, s); MS m/z(TS$^+$)274(MH$^+$) |

-continued (IIa)

| Prep | Prec phenol | Structure (W, Y, Z on ring B) | Data |
|---|---|---|---|
| 34 | Commercially available | quinolin-6-yl | δ_H(CDCl_3, 400MHz) 6.72(1H, d), 7.44–7.60(3H, m), 8.16(1H, d), 8.23(1H, d), 8.58(1H, d), 8.98 (1H, d), 9.07(1H, s), 10.67(1H, s); MS m/z(TS$^+$)251(MH$^+$) |
| 35 | Prep 16 | Y=Et, Z=SMe | δ_H(CDCl_3, 400MHz) 1.26(3H, t), 2.42(3H, s), 2.63(2H, q), 6.68 (1H, d), 6.84(1H, d), 6.91(1H, s), 7.24(1H, d), 8.52(1H, d), 8.99 (1H, s), 10.60(1H, s); MS m/z (TS$^+$)274(MH$^+$) |
| 36 | Ref$^b$ | Z=Et, Y=SMe | δ_H(CDCl_3, 300MHz) 1.28(3H, t), 2.52(3H, s), 2.78(2H, q), 6.68 (1H, d), 7.00(2H, m), 7.28(1H, d), 8.55(1H, d), 9.00(1H, s), 10.63(1H, s); MS m/z(TS$^+$)274 (MH$^+$) |
| 37 | Prep 17 | Y=Cl, Z=SMe | δ_H(CDCl_3, 400MHz) 2.41(3H, s), 6.64(1H, d), 6.82(1H, dd), 6.90 (1H, s), 7.40(1H, d), 8.53(1H, d), 8.98(1H, s), 10.55(1H, s); MS m/z(ES$^+$)312(MNa$^+$) |

$^a$2,3-dihydro-1-benzothiophen-5-ol prepared according to Synth. Commun. 1991, 21, 959–964.
$^b$3-ethyl-4-(methylsulfanyl)phenol prepared according to J. Med. Chem. 1983, 26, 746.

Preparation 38–39

The following compounds of formula IIb, i.e. compounds of general formula II where L is —C(H)—, M is —C(H)—, Q is —C(H)—, U is —N— and T is CHO, were prepared in an analogous fashion to preparation 18 from 2-chloronicotinaldehyde (prepared according to *Chem. Pharm. Bull.*, 2000, 48, 694) and the commercially available phenols indicated. The crude product was generally of sufficient purity to use in the next stage without further purification.

(IIb)

| Prep | Prec phenol | W | Y | Data |
|---|---|---|---|---|
| 38 | commercially available | | SMe (para) | $\delta_H$ (CDCl$_3$, 400 MHz) 2.50 (3H, s), 7.13 (3H, m), 7.35 (2H, d), 8.24 (1H, d), 8.35 (1H, dd), 10.55 (1H, s); MS m/z (TS$^+$) 246 (MH$^+$) |
| 39 | commercially available | | Me (3), SMe (4) | $\delta_H$ (CDCl$_3$, 400 MHz) 2.38 *3H, s), 2.47 (3H, s), 7.02 (2H, m), 7.12 (1H, dd), 7.24 (1H, obs), 8.23 (1H, d), 8.35 (1H, dd), 10.53 (1H, s); MS m/z (TS$^+$) 260 (MH$^+$) |

Preparation 40

4-(2,3-Dihydro-1,4-benzoxathiin-7-yloxy)-N,6-dimethylnicotinamide

The product from Preparation 1 (1.00 g, 5.42 mmol) was combined with the product from Preparation 9 (911 mg, 5.42 mmol), potassium carbonate (1.49 g, 10.8 mmol) and DMF (5 mL). The mixture was then heated to 90–100° C. and then stirred at this temperature for 20 h. The solvent was removed under high vacuum and the residue was slurried in a mixture of DCM/methanol/880 NH$_3$ (93:7:1). The mixture was filtered through a short plug of SiO$_2$ eluting with the same solvent mixture, and the filtrate was evaporated to an off white solid. Trituration with ether afforded the title compound (1.23 g, 72%); $\delta_H$ (CDCl$_3$, 400 MHz) 2.44 (3H, s), 3.01 (3H, d), 3.18 (2H, m), 4.46 (2H, m), 6.46 (1H, s), 6.63 (2H, s+d), 7.12 (1H, d), 7.39 (1H, brs), 9.10 (1H, s); MS m/z (TS$^+$) 317 (MH$^+$).

Preparation 41–44

The following compounds of formula IIc, i.e. compounds of general formula II where L is —C(H)—, M is —N—, Q is —C(Me)-, R is —C(H)— and T is —C(O)NHMe, were prepared in an analogous fashion to Preparation 40 from the product of Preparation 1 and the phenol indicated. In some cases the product was purified by flash chromatography on silica gel.

(IIc)

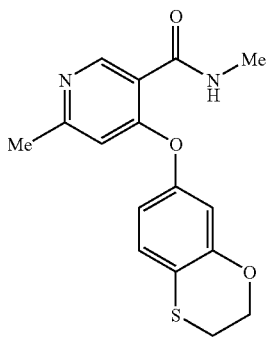

| Prep | Prec phenol | W | Y | Data |
|---|---|---|---|---|
| 41 | commercially available | | SMe (para) | $\delta_H$ (CDCl$_3$, 400 MHz) 2.43 (3H, s), 2.57 (3H, s), 3.02 (3H, d), 6.40 (1H, s), 7.05 (2H, d), 7.38 (3H, m), 9.21 (1H, s); MS m/z (TS$^+$) 289 (MH$^+$) |
| 42 | Prep 13 | | OMe (3), SMe (4) | $\delta_H$ (CDCl$_3$, 400 MHz) 2.13 (3H, s), 2.30 (3H, s), 3.29 (3H, s), 3.70 (3H, s), 6.02 (1H, brs), 6.71 (2H, s+d), 6.91 (1H, d), 7.45 (1H, brs); MS m/z (TS$^+$) 318 (MH$^+$) |

-continued

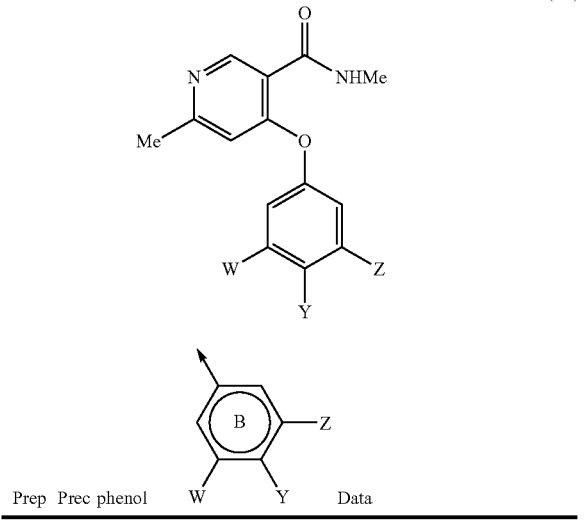

| Prep | Prec phenol | W | Y | Data |
|---|---|---|---|---|
| 43 | Prep 9 | 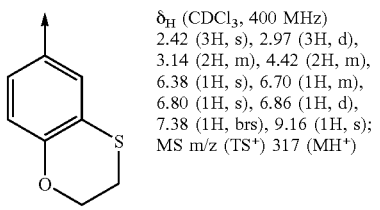 | | $\delta_H$ (CDCl$_3$, 400 MHz) 2.42 (3H, s), 2.97 (3H, d), 3.14 (2H, m), 4.42 (2H, m), 6.38 (1H, s), 6.70 (1H, m), 6.80 (1H, s), 6.86 (1H, d), 7.38 (1H, brs), 9.16 (1H, s); MS m/z (TS$^+$) 317 (MH$^+$) |
| 44 | commercially available | 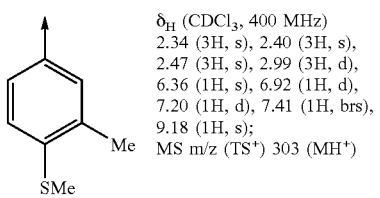 | | $\delta_H$ (CDCl$_3$, 400 MHz) 2.34 (3H, s), 2.40 (3H, s), 2.47 (3H, s), 2.99 (3H, d), 6.36 (1H, s), 6.92 (1H, d), 7.20 (1H, d), 7.41 (1H, brs), 9.18 (1H, s); MS m/z (TS$^+$) 303 (MH$^+$) |

Preparation 45

6-Methyl-4-[4-methyl-3-(methylsulfanyl)phenoxy]nicotinamide

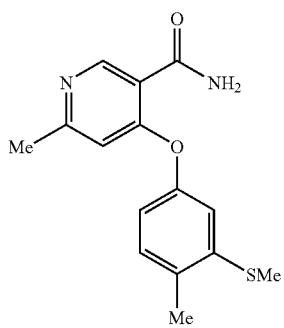

The title compound was prepared in an analogous fashion to Preparation 40 from the product of preparation 2 and 4-Methyl-3-(methylsulfanyl)phenol (prepared according to L. Testaferri, M. Tiecco, M. Tingoli, D. Chianelli, F. Maiolo, *Tetrahedron*, 1982, 38, 2721–2724); $\delta_H$ (CD$_3$OD, 400 MHz) 2.31 (3H, s), 2.40 (3H, s), 2.44 (3H, s), 6.57 (1H, s), 6.87 (1H, dd), 7.05 (1H, d), 7.26 (1H, d), 8.81 (1H, s); MS m/z (TS$^+$) 289 (MH$^+$).

Preparation 46

6-Methyl-4-[4-chloro-3-(methylsulfanyl)phenoxy]nicotinamide

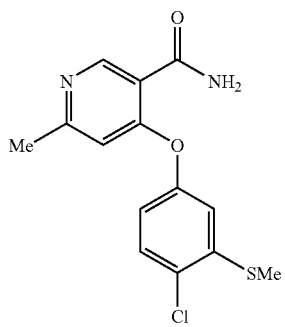

The title compound was prepared in an analogous fashion to Preparation 40 from the product of preparation 2 and the phenol of preparation 17; $\delta_H$ (CDCl$_3$, 400 MHz) 2.42 (3H, s), 2.44 (3H, s), 5.85 (1H, br), 6.40 (1H, s), 6.80 (1H, dd), 6.86 (1H, d), 7.24 (1H, br), 7.40 (1H, d), 9.19 (1H, s); MS m/z (ES$^+$) 309 (MH$^+$).

Preparation 47

3-(3-Methyl-4-sulfanylphenoxy)isonicotinonitrile

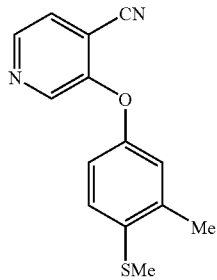

The product of Preparation 71 (500 mg, 3.61 mmol) was combined with 3-methyl-4-sulfanylphenol (556 mg, 3.61 mmol) and potassium carbonate (748 mg, 5.41 mmol) in DMF (20 mL). The mixture was stirred and heated to 110° C. for 15 h. After cooling to room temperature, the mixture was diluted with water (150 mL) and extracted with EtOAc (3×100 mL). The combined organic layers were dried (MgSO$_4$), filtered and evaporated to dryness. The residue was purified by flash chromatography [SiO$_2$; DCM/MeOH (100:0 to 99:1)] to afford the title compound as a colourless oil (840 mg, 91%); $\delta_H$ (CDCl$_3$, 400 MHz) 2.32 (3H, s), 2.44 (3H, s), 6.92 (2H, m), 7.18 (1H, d), 7.47 (1H, d), 8.27 (1H, s), 8.40 (1H, d); MS m/z (TS$^+$) 257 (MH$^+$).

Preparations 48–63

The following compounds of formula IId, i.e. compounds of general formula II where T is cyano, were prepared in an analogous fashion to Preparation 47 from the compound of preparation 71 and the phenol indicated.

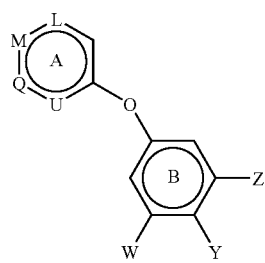
(IId)
| Prep | Prec phenol | L | M | Q | U | W, Y, Z (B ring) | Data |
|---|---|---|---|---|---|---|---|
| 48[a] | commercial | —N— | —C(H)— | —C(H)— | —N— | 4-CF₃-phenyl | δ_H (CDCl₃, 400 MHz) 7.37 (2H, d), 7.74 (2H, d), 8.28 (1H, s), 8.44 (1H, s); MS m/z (TS⁺) 283 (MNH₄⁺) |
| 49 | commercial | —C(H)— | —C(H)— | —N— | —C(H)— | 4-SMe-phenyl | δ_H (CDCl₃, 300 MHz) 2.54 (3H, s), 7.08 (2H, d), 7.37 (2H, d), 7.57 (1H, d), 8.35 (1H, s), 8.48 (1H, d); MS m/z (TS⁺) 243 (MH⁺) |
| Prep | Prec phenol | L | M | Q | U | W, Y, Z (B ring) | Data |
|---|---|---|---|---|---|---|---|
| 50[b] | commercial | —N— | —C(H)— | —C(H)— | —C(H)— | 4-SMe-phenyl | δ_H (CDCl₃, 400 MHz) 2.46 (3H, s), 7.00 (2H, d), 7.19 (1H, d), 7.28 (2H, d), 7.37 (1H, m), 8.36 (1H, d); MS m/z (TS⁺) 243 (MH⁺) |
| 51 | Prep 8 | —C(H)— | —C(H)— | —N— | —C(H)— | 3-F-4-SMe-phenyl | δ_H (CDCl₃, 400 MHz) 6.82–6.89 (2H, m), 7.31 (1H, t), 7.49 (1H, m), 8.36 (1H, s), 8.49 (1H, m) |

-continued (IId)

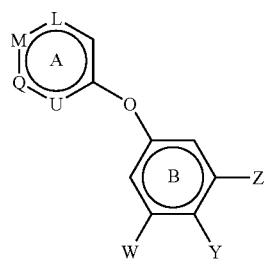

| # | | L | M | Q | U | B-substituent | NMR/MS |
|---|---|---|---|---|---|---|---|
| 52 | Prep 9 | —C(H)— | —C(H)— | —N— | —C(H)— | benzo[1,4]oxathiine-6-yl | δ$_H$ (CDCl$_3$, 400 MHz) 3.10 (2H, m), 4.38 (2H, m), 6.70 (1H, m), 6.80 (2H, m), 7.44 (1H, d), 8.25 (1H, s), 8.37 (1H, d); MS m/z (TS$^+$) 271 (MH$^+$) |
| 53 | commercial | —C(H)— | —C(H)— | —N— | —C(H)— | 4-ethylphenyl | δ$_H$ (CDCl$_3$, 400 MHz) 1.23 (3H, t), 2.61 (2H, q), 7.00 (2H, d), 7.22 (2H, d), 7.48 (1H, d), 8.27 (1H, s), 8.40 (1H, d); MS m/z (TS$^+$) 225 (MH$^+$) |
| 54 | Prep 12 | —C(H)— | —C(H)— | —N— | —C(H)— | 4-SMe-3-CF$_3$-phenyl | δ$_H$ (CDCl$_3$, 400 MHz) 2.50 (3H, s), 7.22 (1H, m), 7.37 (1H, d), 7.42 (1H, d), 7.53 (1H, d), 8.31 (1H, brs), 8.49 (1H, brs); MS m/z (TS$^+$) 311 (MH$^+$) |
| 55 | Ref$^c$ | —C(H)— | —C(H)— | —N— | —C(H)— | 3-SMe-4-Me-phenyl | δ$_H$ (CDCl$_3$, 400 MHz) 2.32 (3H, s), 2.44 (3H, s), 6.77 (1H, dd), 6.89 (1H, d), 7.17 (1H, d), 7.51 (1H, d), 8.31 (1H, s), 8.43 (1H, d) |
| 56 | commercial | —C(H)— | —C(H)— | —N— | —C(H)— | indan-5-yl | δ$_H$ (CDCl$_3$, 400 MHz) 2.09 (2H, m), 2.89 (4H, m), 6.94 (1H, d), 7.21 (1H, d), 7.48 (1H, d), 8.26 (1H, s), 8.38 (1H, d) |
| 57 | Prep 13 | —C(H)— | —C(H)— | —N— | —C(H)— | 3-OMe-4-SMe-phenyl | δ$_H$ (CDCl$_3$, 300 MHz) 2.49 (3H, s), 3.92 (3H, s), 6.70 (1H, s), 6.71 (1H, d), 7.21 (1H, d), 7.55 (1H, d), 8.37 (1H, s), 8.47 (1H, d) |

-continued
(IId)
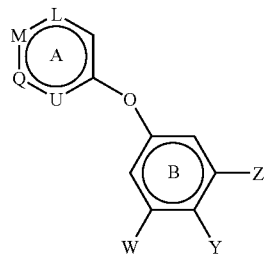
| | | L | M | Q | U | Z | δ_H |
|---|---|---|---|---|---|---|---|
| 58 | Prep 15 | —C(H)— | —C(H)— | —N— | —C(H)— | 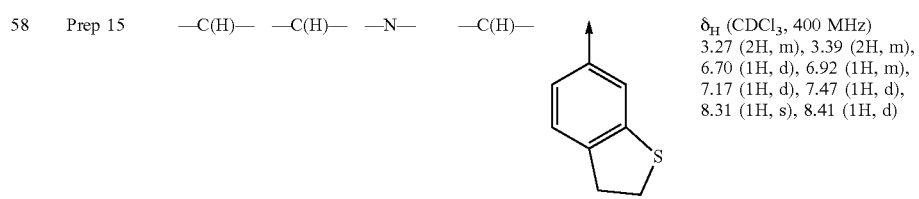 | δ_H (CDCl_3, 400 MHz) 3.27 (2H, m), 3.39 (2H, m), 6.70 (1H, d), 6.92 (1H, m), 7.17 (1H, d), 7.47 (1H, d), 8.31 (1H, s), 8.41 (1H, d) |
| 59 | Ref[d] | —C(H)— | —C(H)— | —N— | —C(H)— | 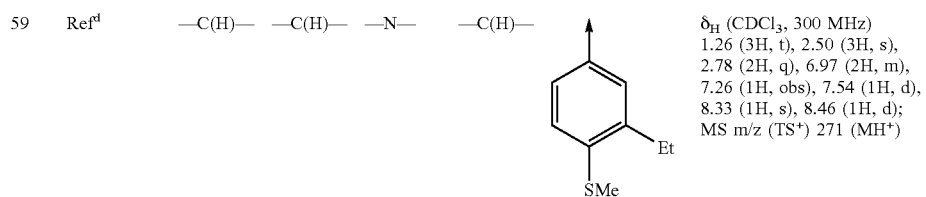 | δ_H (CDCl_3, 300 MHz) 1.26 (3H, t), 2.50 (3H, s), 2.78 (2H, q), 6.97 (2H, m), 7.26 (1H, obs), 7.54 (1H, d), 8.33 (1H, s), 8.46 (1H, d); MS m/z (TS+) 271 (MH+) |
| 60 | Prep 11 | —C(H)— | —C(H)— | —N— | —C(H)— | 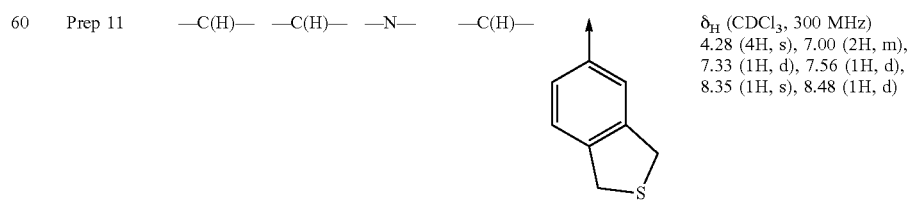 | δ_H (CDCl_3, 300 MHz) 4.28 (4H, s), 7.00 (2H, m), 7.33 (1H, d), 7.56 (1H, d), 8.35 (1H, s), 8.48 (1H, d) |
| 61 | Ref[e] | —C(H)— | —C(H)— | —N— | —C(H)— | 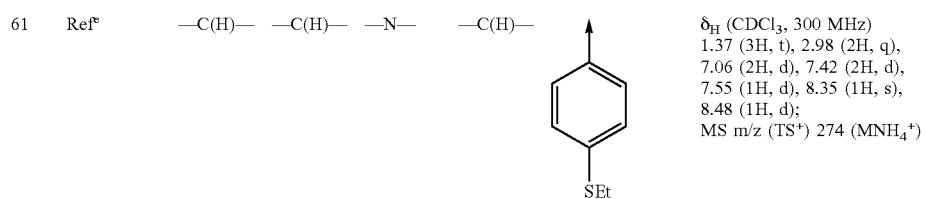 | δ_H (CDCl_3, 300 MHz) 1.37 (3H, t), 2.98 (2H, q), 7.06 (2H, d), 7.42 (2H, d), 7.55 (1H, d), 8.35 (1H, s), 8.48 (1H, d); MS m/z (TS+) 274 (MNH_4+) |
| 62 | Prep 7 | —C(H)— | —C(H)— | —N— | —C(H)— | 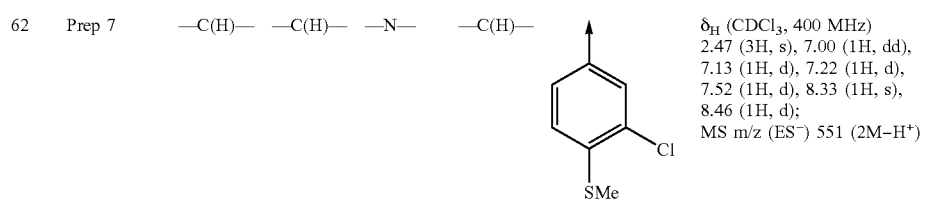 | δ_H (CDCl_3, 400 MHz) 2.47 (3H, s), 7.00 (1H, dd), 7.13 (1H, d), 7.22 (1H, d), 7.52 (1H, d), 8.33 (1H, s), 8.46 (1H, d); MS m/z (ES−) 551 (2M−H+) |

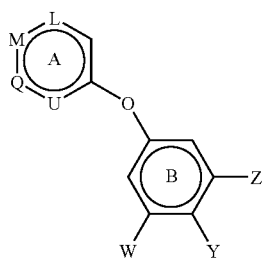

(IId)

| 63 | Prep 17 | —C(H)— | —C(H)— | —N— | —C(H)— | 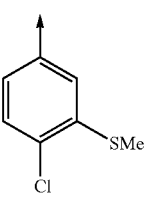 | δ_H (CDCl_3, 400 MHz) 2.42 (3H, s), 6.76 (1H, dd), 6.92 (1H, d), 7.36 (1H, d), 7.53 (1H, d), 8.32 (1H, s), 8.46 (1H, d) |

[a]Prepared from commercially available 3-chloro-2-pyrazinecarbonitrile and 4-trifluoromethylphenol.

[b]Prepared from the commercially available phenol and 3-chloro-2-pyridinecarbonitrile [prepared according to W. K. Fife, Heterocycles 1984, 22, 93–96].

[c]4-Methyl-3-(methylsulfanyl)phenol prepared according to L. Testaferri, M. Tiecco, M. Tingoli, D. Chianelli, F. Maiolo, Tetrahedron, 1982, 38, 2721–2724.

[d]3-Ethyl-4-(methylsulfanyl)phenol prepared according to P. Jacob III, A. T. Shulgin, J. Med. Chem. 1983, 26, 746.

[e]4-(Ethylsulfanyl)phenol prepared according to E. Miller, R. R. Reed, J. Am. Chem. Soc. 1933, 55, 1224.

Preparation 64

3-[3-Methyl-4-(methylsulfanyl)phenoxy]isonicotinamide

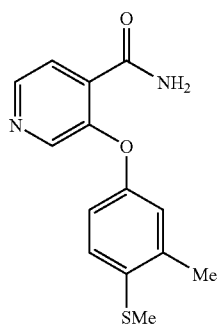

(i) Preparation of 3-[3-methyl-4-(methylsulfanyl)phenoxy]isonicotinic acid

6M NaOH (200 mL) was added to a solution of the nitrile of preparation 47 (32.3 g of uncolumned material prepared from 0.12 mmol of 3-chloroisonicotinonitrile) in EtOH (200 mL) and the mixture was heated at reflux for 7 h. After cooling to room temperature the volume was reduced to approximately 200 mL and the mixture was diluted with water (800 mL). The pH was adjusted to 1 with conc. HCl, keeping the temperature below 35° C. using an ice bath, and the resulting cream precipitate was filtered. The water wet paste was transferred to a 2 L round bottomed flask, suspended in toluene and concentrated in vacuo (3×500 mL). Drying in vacuo overnight at 50° C. then gave the title acid (35 g) as a light brown powder which was carried into the following step without further purification; $\delta_H$ (CD_3OD, 400 MHz) 2.27 (3H, s), 2.40 (3H, s), 6.87 (2H, m), 7.24 (1H, d), 7.95 (1H, br), 8.28 (1H, s), 8.47 (1H, d).

(ii) Preparation of 3-[3-methyl-4-(methylsulfanyl)phenoxy]isonicotinamide

CDI (19.46 g, 0.12 mol) was added to a suspension of the preceding acid (35 g) in THF (600 mL) and the mixture was stirred at room temperature for 80 min. The surface of the reaction was flushed with nitrogen to remove $CO_2$ and a 2M solution of methylamine in THF (88 mL, 0.176 mol) was added dropwise over 15 min. The mixture was stirred overnight and the solvent was then removed in vacuo. The residue was taken up in ether (1 L), washed with saturated $NH_4Cl$ (aq) (2×300 mL), 2M NaOH (2×300 mL) and brine, dried (MgSO_4) and evaporated to give the title amide (28.3 g, 82% from 3-chloroisonicotinonitrile) as an orange foam; $\delta_H$ (CDCl_3, 400 MHz) 2.37 (3H, s), 2.48 (3H, s), 3.02 (3H, d), 6.93 (2H, m), 7.21 (1H, d), 7.60 (1H, br), 8.07 (1H, d), 8.20 (1H, s), 8.44 (1H, d); MS m/z (ES+) 211 (MNa+).

Preparation 65

2-(3,4-Dichlorophenoxy)nicotinaldehyde

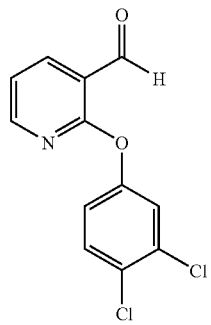

Under N₂ in a 250 mL round-bottomed flask fitted with a reflux condenser and magnetic stirrer, 3,4-dichlorophenol (2.9 g, 17.8 mmol) was added to a suspension of $K_2CO_3$ (7.0 g, 51 mmol) in 70 mL of anhydrous DMF. After stirring the mixture for 15 min., 2-chloronicotinaldehyde (2.4 g, 17 mmol prepared according to the method in *J. Heterocycl. Chem.* 1995, 32, 1595) was added and the mixture was heated to 90–100° C. for 5 h. After allowing the reaction to cool to room temperature overnight, the mixture was diluted with water and extracted three times with EtOAc. The aqueous layer was then extracted with additional EtOAc and the organic layers were combined, washed with water and brine and dried over $Na_2SO_4$. Removal of the solvent in vacuo gave a brown solid which was further dried under vacuum overnight and then recrystallized from EtOAc to give the title product as tan crystals, 1.6 g; m.p. 97–99° C. A second crop of tan crystals weighing 0.716 g was later obtained, and concentration of the filtrate provided an additional 2.65 g of nearly pure title product; $\delta_H$ (CDCl₃, 400 MHz) 7.08 (1H, dd), 7.17 (1H, m), 7.43 (1H, d), 7.49 (1H, d), 8.25 (1H, dd), 8.33 (1H, dd), 10.50 (1H, s).

Preparation 66

4-(3,4-dichlorophenoxy)nicotinaldehyde

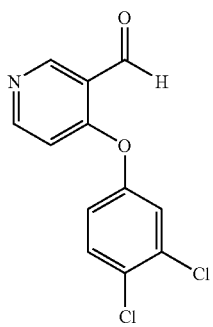

The title compound was prepared according to Preparation 65 starting from 3,4-dichlorophenol and 4-chloronicotinaldehyde (prepared according to D. Albanese, M. Penso, M. Zenoni, *Synthesis* 1999, 1294–1296); $\delta_H$ (CDCl₃, 400 MHz) 6.71 (1H, d), 7.04 (1H, dd), 7.27 (1H, m), 7.55 (1H, d), 8.02 (1H, s), 8.60 (1H, dd), 10.54 (1H, s); MS m/z268 (MH⁺).

Preparation 67

2-(3,4-dichlorophenoxy)-3-quinolinecarbaldehyde

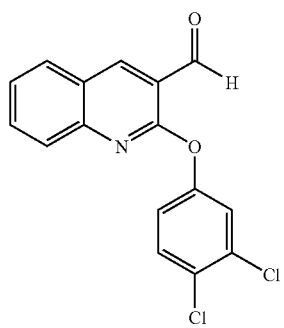

The title compound was prepared according to preparation 65 starting from 3,4-dichlorophenol and 2-chloro-3-quinoline carboxaldehyde (Aldrich Chemical Co.); $\delta_H$ (CDCl₃, 400 MHz) 7.19 (1H, m), 7.50 (3H, m), 7.74 (2H, m), 7.91 (1H, dd), 8.75 (1H, s), 10.59 (1H, s); MS m/z318, 320 (MH⁺).

Preparation 68

2-(4-Chlorophenoxy)-N,N-dimethylnicotinamide

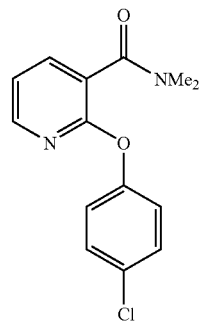

To a rapidly stirred mixture of 10 mL of benzene and dimethylamine (2.6 mL of a 40% solution) was added a slurry of 2-(4-chlorophenoxy)nicotinoyl chloride (0.536 g, 2 mmol, Maybridge Chemical Co.) over 5 min. The biphasic mixture was stirred at room temperature for 18 h and then diluted with water and benzene. The aqueous layer was further extracted with benzene and the organic layers were combined and washed (brine, water), dried ($Na_2SO_4$) and concentrated in vacuo to produce the product as a pale yellow oil (0.432 g); $\delta_H$ (CDCl₃, 400 MHz) 8.14 (dd, 1H), 7.72 (dd, 1H), 7.33 (m, 2H), 7.03 (m, 3H), 3.12 (s, 3H), 2.99 (s, 3H); MS m/z279, 277 (MH⁺).

Preparation 69

5-Bromo-2-[4-(trifluoromethoxy)phenoxy]nicotinic Acid

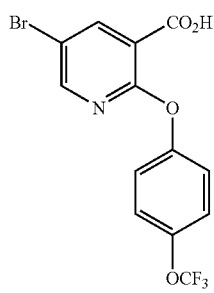

A mixture of 5-bromo-2-chloronicotinic acid (2.36 g, 10 mmol), 4-trifluoromethoxyphenol (2.14 g, 12 mmol) and K$_2$CO$_3$ (4.14 g, 30 mmol) in DMF (30 mL) was heated at 140° C. for 24 h. After cooling to room temperature the mixture was diluted with water (150 mL) and the pH was adjusted to 6 with acetic acid. The mixture was extracted with EtOAc (3×50 mL) and the combined organic extracts were dried (MgSO$_4$) and evaporated to give an oil. This was triturated with water to give a sticky solid which was filtered and washed with water and then pentane. The resulting beige solid was suspended in further pentane, sonicated, filtered and dried in vacuo at 60° C. to give the product (0.92 g, 24%) as a beige solid; ($\delta_H$ (CDCl$_3$, 300 MHz) 7.19 (2H, m), 7.28 (2H, m), 8.35 (1H, s), 8.58 (1H, s); MS m/z (TS$^+$) 378, 380 (MH$^+$).

Preparation 70

5-Bromo-N,N-dimethyl-2-[4-(trifluoromethoxy)phenoxy]nicotinamide

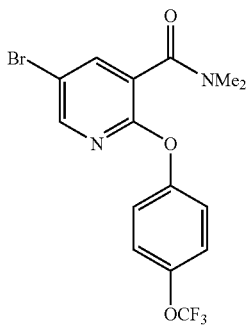

N-N-Diisopropylethylamine (1.83 mL, 10.5 mmol), HOBt (472 mg, 3.5 mmol) and WSCDI (537 mg, 2.8 mmol) were added to a solution of preparation 69 (880 mg, 2.3 mmol) in CH$_2$Cl$_2$ (50 mL) to give a brown solution. MgSO$_4$ (2 g) was added followed by dimethylamine hydrochloride (380 mg, 4.7 mmol) and the mixture was stirred at room temperature for 2 h. Tlc analysis indicated starting material remaining so a further portion of WSCDI (100 mg, 0.5 mmol) and dimethylamine hydrochloride (190 mg, 2.3 mmol) was added and stirring was continued for 2 h. Water (50 mL) was added, the organic layer was separated and the aqueous layer was extracted with CH$_2$Cl$_2$ (2×50 mL). The combined organic layers were washed with brine, dried (MgSO$_4$) and evaporated. The residue was purified by column chromatography [SiO$_2$; DCM/MeOH/880 NH$_3$ (99:1:0.1)] to give the desired product (355 mg, 38%); $\delta_H$ (CDCl$_3$, 300 MHz) 3.02 (3H, s), 3.14 (3H, s), 7.15 (2H, m), 7.23 (2H, m), 7.85 (1H, d), 8.19 (1H, d); MS m/z (ES+) 405, 407 (MH$^+$).

Preparation 71

3-Chloro-isonicotinonitrile

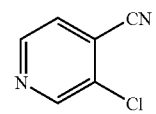

The title compound was prepared by a modified procedure based on the method of J. Rokach and Y. Girard, *J. Heterocycl. Chem.* 1978, 15, 683–684. 4-Cyanopyridine-N-oxide (250 g, 2.08 mol) was added portionwise to a stirred suspension of PCl$_5$ (599.94 g, 2.88 mol) and POCl$_3$ (800 mL, 8.71 mol) at 20° C. under nitrogen, in a reactor fitted with a reflux condensor. During the addition the temperature rose to 41° C. The mixture was stirred at 100° C. for 3 h then cooled to 95° C. and transferred to a mixture of 6M HCl (200 mL) and a 6:4 mixture of ice and water (5994 g) at such a rate that the temperature stayed below 15° C. (about 35 min). The resulting brown solution was cooled to below 5° C. and taken to pH 4.15 by adding 33% aqueous NaOH (about 4.5 L), keeping the temperature below 5° C. The resulting beige precipitate was filtered and washed thoroughly with water (4×500 mL), sucking as dry as possible. The residue was suspended in water (1.5 L) and n-heptane (7 L) and stirred at 30° C. for 1 h. The aqueous phase was separated and extracted further with n-heptane (2×2 L), stirring for 30 min each time at 30° C. The combined heptane layers were combined, dried (Na$_2$SO$_4$, 136 g), filtered and the resulting solution was concentrated under reduced pressure to a weight of 1.9 kg (about 3 L), at which point the product began to crystallise. The mixture was cooled to 0° C., stirred for 1.5 h then the product was filtered, washed with cold n-heptane (2×125 mL) and dried at room temperature in a circulating air drier to give the product (129.08 g, 44.8%) as a crystalline solid; m.p. 73.4° C.

Biological Activity

A number of compounds were tested for biological activity by their ability to inhibit the uptake of serotonin by human serotonin transporters as follows.

(i) Cell Culture

Human embryonic kidney cells (HEK-293) stably transfected with either the human serotonin transporter (hSERT), noradrenaline transporter (hNET) or dopamine transporter (hDAT) were cultured under standard cell culture techniques (cells were grown at 37° C. and 5% CO$_2$ in DMEM-culture media (supplemented with 10% dialysed foetal calf serum (FCS), 2 mM I-glutamine and 250 μg/ml geneticin)). Cells were harvested for the assay to yield a cell suspension of 750,000 cells/ml.

(i) Determination of Inhibitor Potency

All test compounds were dissolved in 100% DMSO and diluted down in assay buffer to give appropriate test concentrations. Assays were carried out in 96-well filter bottom plates. Cells (7500 cells/assay well) were pre-incubated in standard assay buffer containing either test compound, standard inhibitor or compound vehicle (1% DMSO) for 5 minutes. Reactions were started by addition of either $^3$H-Serotonin, $^3$H-Noradrenaline or $^3$H-Dopamine substrates. All reactions were carried out at room temperature in a shaking incubator. Incubation times were 5 minutes for the hSERT and hDAT assays and 15 minutes for the hNET assay. Reactions were terminated by removal of the reaction mixture using a vacuum manifold followed by rapid washing with ice cold assay buffer. The quantity of $^3$H-substrate incorporated into the cells was then quantified.

Assay plates were dried in a microwave oven, scintillation fluid added, and radioactivity measured. Potency of test compounds was quantified as $IC_{50}$ values (concentration of test compound required to inhibit the specific uptake of radiolabelled substrate into the cells by 50%).

(iii) Standard Assay Buffer Composition:
Trizma hydrochloride (26 mM)
NaCl (124 mM)
KCl (4.5 mM)
$KH_2PO_4$ (1.2 mM)
$MgCl_2.6H_2O$ (1.3 mM)
Ascorbic acid (1.136 mM)
Glucose (5.55 mM)
pH 7.40
$CaCl_2$ (2.8 mM)
Pargyline (100 μM)
Note: The pH of the buffer was adjusted to 7.40 with 1M NaOH before addition of $CaCl_2$ and pargyline.

(iv) Summary of Assay Parameters

| | hSERT Assay | hDAT Assay | hNET Assay |
|---|---|---|---|
| Cell concentration per assay well. | 75,000 | 75,000 | 75,000 |
| Substrate Concentration. | $^3$H-5HT (50 nM) | $^3$H-Dopamine (200 nM) | $^3$H-Noradrenaline (200 nM) |
| Incubation time (minutes) | 5 | 5 | 15 |

The compounds of the invention are potent and selective inhibitors of serotonin re-uptake.

Compounds having a serotonin re-uptake inhibition (SRI) $IC_{50}$ value of less than or equal to 50 nM include the title compounds of Examples 18–28, 30–44, 46–49, 51–52, 55, 58–72, 74–78, 80–88, 90–106 and 108.

Compounds having an serotonin re-uptake inhibition (SRI) $IC_{50}$ value of less than or equal to 25 nM and which are more than 100-fold as potent in the inhibition of serotonin re-uptake than in the inhibition of dopamine re-uptake or noradrenaline re-uptake include the title compounds of Examples 18–23, 25, 27–28, 30–35, 38, 40, 42, 44, 46–49, 51–52, 55, 58–62, 64–68, 70, 72, 78, 80–85, 87–88, 90–92, 94–98, 101, 105 and 108.

Compounds having an serotonin re-uptake inhibition (SRI) $IC_{50}$ value of less than or equal to 25 nM and which are more than 100-fold as potent in the inhibition of serotonin re-uptake than in the inhibition of dopamine re-uptake and noradrenaline re-uptake include the title compounds of Examples 18–22, 27–28, 30–35, 38, 44, 46–48, 51, 59, 61, 64–67, 78, 80, 82, 84, 87–88, 90–92, 95–98 and 101.

The invention claimed is:

1. A compound of general formula (I), or pharmaceutically acceptable salts thereof;

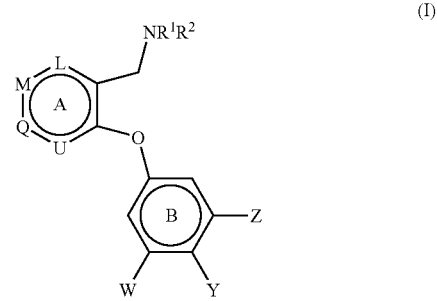

wherein;

L and U, which may be the same or different, are —N—, —N$^+$(—O$^-$)— or —C(H)—;

M and Q, which may be the same or different, are —N—, —N$^+$(—O$^-$)— or —C(R$^4$)—;

wherein ring A contains 1 nitrogen atoms;

R$^1$ and R$^2$, which may be the same or different, are hydrogen, $C_{1-6}$alkyl, $(CH_2)_m(C_{3-6}$cycloalkyl) wherein m=0, 1, 2 or 3, or R$^1$ and R$^2$ together with the nitrogen to which they are attached form an azetidine ring;

W, Y and Z, which may be the same or different, are hydrogen, halogen, $C_{1-6}$alkyl, $CF_3$, $OCF_3$, $C_{1-4}$alkylthio or $C_{1-4}$alkoxy; or Y and Z are linked so that, together with the interconnecting atoms, Y and Z form a fused 5 to 7-membered carbocyclic or heterocyclic ring which may be saturated, unsaturated or aromatic, and wherein when Y and Z form a heterocyclic ring, in addition to carbon atoms, the linkage contains one or two heteroatoms independently selected from oxygen, sulfur and nitrogen; and wherein W, Y and Z are not all hydrogen; and each R$^4$ is independently:

A-X, wherein A=—(CH$_2$)$_p$— where p is 0, 1 or 2; X is hydrogen, CONR$^6$R$^7$, SO$_2$NR$^6$R$^7$, SO$_2$NHC(=O)R$^6$, hydroxy, $C_{1-4}$alkoxy, NR$^8$SO$_2$R$^9$, NO$_2$, NR$^6$R$^{11}$, CN, CO$_2$R$^{10}$, SR$^{10}$, S(O)R$^9$ or SO$_2$R$^{10}$; R$^6$, R$^7$, R$^8$ and R$^{10}$ which may be the same or different, are hydrogen or $C_{1-6}$alkyl optionally substituted independently by one or more R$^{12}$; R$^9$ is $C_{1-6}$ alkyl optionally substituted independently by one or more R$^{12}$; R$^{11}$ is hydrogen, $C_{1-6}$ alkyl optionally substituted independently by one or more R$^{12}$, C(O)R$^6$, CO$_2$R$^9$, C(O)NHR$^6$ or SO$_2$NR$^6$R$^7$; R$^{12}$ is fluoro, hydroxy, CO$_2$H, $C_{3-6}$cycloalkyl, NH$_2$, CONH$_2$, $C_{1-6}$alkoxy, $C_{1-6}$alkoxycarbonyl or a 5- or 6-membered heterocyclic ring containing 1, 2 or 3 heteroatoms selected from N, S and O optionally substituted independently by one or more R$^{13}$; or R$^6$ and R$^7$, together with the nitrogen to which they are attached, form a 4-, 5- or 6-membered heterocyclic ring optionally substituted independently by one or more R$^{13}$; or a 5- or 6-membered heterocyclic ring containing 1, 2 or 3 heteroatoms selected from N, S and O, optionally substituted independently by one or more R$^{13}$; wherein R$^{13}$ is hydroxy, $C_1$–$C_4$alkoxy, fluoro, $C_1$–$C_6$alkyl, haloalkyl, haloalkoxy, —NH$_2$, —NH(C$_1$–C$_6$alkyl) or —N(C$_1$–C$_6$alkyl)$_2$.

2. A compound according to claim 1 wherein L is —C(H)—.

3. A compound according to claim 1 wherein $R^1$ and $R^2$, which may be the same or different, are hydrogen or $C_1$–$C_6$alkyl, or $R^1$ and $R^2$, together with the nitrogen to which they are attached, form an azetidine ring.

4. A compound according claim 1 wherein $R^1$ is methyl and $R^2$ is hydrogen or methyl, or $R^1$ and $R^2$, together with the nitrogen to which they are attached, form an azetidine ring.

5. A compound according to claim 1 wherein $R^1$ is methyl and $R^2$ is hydrogen or methyl.

6. A compound according to claim 1 wherein W is hydrogen, $C_{1-6}$alkyl, $C_{1-4}$ alkoxy or halogen.

7. A compound according to claim 1 wherein W is hydrogen, methyl or ethyl; and Y and Z, which may be the same or different, are hydrogen, methyl, ethyl, $CF_3$, $OCF_3$, methylthio, ethylthio, methoxy, ethoxy, chloro, fluoro or bromo; or Y and Z are linked so that, together with the interconnecting atoms, Y and Z form a fused 5 to 7-membered carbocyclic or heterocyclic ring which may be saturated, unsaturated or aromatic, and wherein when Y and Z form a heterocyclic ring, in addition to carbon atoms, the linkage contains one or two heteroatoms independently selected from oxygen, sulfur and nitrogen; wherein W, Y and Z are not all hydrogen.

8. A compound according to claim 1 wherein W is hydrogen; and Y and Z, which may be the same or different, are hydrogen, fluoro, chloro, methyl, ethyl, methylthio, ethylthio, methoxy or ethoxy; or Y and Z are linked so that, together with the interconnecting atoms, Z and Y form a fused 5 to 7-membered heterocyclic ring containing one or more sulfur atoms; wherein Y and Z are not both hydrogen.

9. A compound according to claim 1 wherein when Y and Z are linked so that, together with the interconnecting atoms, Z and Y form a fused 5 to 7-membered heterocyclic ring containing one or more sulfur atoms, the linkages forming the fused ring are —S(CH$_2$)$_2$—, —CH$_2$S—CH$_2$— or —S(CH$_2$)$_2$O— wherein either end of these linkages correspond to either group Y or Z.

10. A compound according to claim 1 wherein, when present, each $R^4$ is independently —(CH$_2$)$_p$—X, where p is 0, 1 or 2; X is hydrogen, CONR$^6$R$^7$, SO$_2$NR$^6$R$^7$, SO$_2$NH(C=O)R$^6$, hydroxy, $C_{1-4}$alkoxy, NR$^8$SO$_2$R$^9$, NO$_2$, NR$^6$R$^{11}$, CN, CO$_2$R$^{10}$, SR$^{10}$, S(O)R$^9$ or SO$_2$R$^{10}$; wherein R$^6$, R$^7$, R$^8$, R$^{10}$ or R$^{11}$, which may be the same or different, are hydrogen or $C_{1-6}$alkyl; and R$^9$ is $C_{1-6}$alkyl.

11. A compound according to claim 1 wherein, when present each $R^4$ is independently —(CH$_2$)$_p$—X, where p is 0 or 1; X is hydrogen, CONR$^6$R$^7$, SO$_2$NR$^6$R$^7$, NR$^8$SO$_2$R$^9$, hydroxy or NR$^6$R$^{11}$; wherein R$^6$, R$^7$, R$^8$, or R$^{11}$, which may be the same or different, are hydrogen or $C_{1-6}$alkyl; and R$^9$ is $C_{1-6}$alkyl.

12. A compound according to claim 1 wherein the compound is selected from:
N-methyl-N-({4-[4-(methylsulfanyl)phenoxy]-3-pyridinyl}methyl)amine,
N-{[4-(2,3-dihydro-1-benzothien-5-yloxy)-3-pyridinyl]methyl}-N-methylamine,
N-({4-[3-chloro-4-(methylsulfanyl)phenoxy]-3-pyridinyl}methyl)-N-methylamine,
N-methyl-N-({3-[4-(methylsulfanyl)phenoxy]-4-pyridinyl}methyl)amine,
N-methyl-N-({3-[3-methyl-4-(methylsulfanyl)phenoxy]-4-pyridinyl}-methyl)amine,
N-{[4-(2,3-Dihydro-1,4-benzoxathiin-7-yloxy)-6-methyl-3-pyridinyl]methyl}-N-methylamine,
N-methyl-N-({6-methyl-4-[3-methyl-4-(methylsulfanyl)phenoxy]-3-pyridinyl}methyl)amine,
N-({4-[3-chloro-4-(methylsulfanyl)phenoxy]-3-pyridinyl}methyl)-N,N-dimethylamine,
N-({4-[3-fluoro-4-(methylsulfanyl)phenoxy]-3-pyridinyl}methyl)-N,N-dimethylamine,
N,N-dimethyl-N-({3-[4-(methylsulfanyl)phenoxy]-4-pyridinyl}methyl)amine,
N-{[4-(2,3-dihydro-1-benzothien-5-yloxy)-3-pyridinyl]methyl}-N,N-dimethylamine,
N-({4-[3-Methoxy-4-(methylsulfanyl)phenoxy]-3-pyridinyl}methyl)-N,N-dimethylamine,
N,N-dimethyl-N-({4-[4-(trifluoromethyl)phenoxy]-3-pyridinyl}methyl)amine,
N,N-dimethyl-N-({4-[4-(methylsulfanyl)phenoxy]-3-pyridinyl}methyl)amine, and
N,N-dimethyl-N-({4-[3-methyl-4-(methylsulfanyl)phenoxy]-3-pyridinyl}-methyl)amine.

13. The compound N-methyl-N-({3-[3-methyl-4-(methylsulfanyl)phenoxy]-4-pyridinyl}-methyl)amine or a pharmaceutically acceptable salt thereof.

14. The tartrate salt of the compound of claim 13.

15. The compound N-methyl-N-({3-[4-(methytsulfanyl)phenoxy]-4-pyridinyl}-methyl)amine or a pharmaceutically acceptable salt thereof.

16. The tartrate salt of the compound of claim 15.

17. A composition comprising a compound of formula (I) of any one of claims 1, and 2–12, or pharmaceutically acceptable salts thereof, and a pharmaceutically acceptable diluent or carrier.

18. A therapeutic method of treating premature ejaculation comprising administering a therapeutically effective amount of a compound of formula (I) of any one of claims 1, and 2–12, or a pharmaceutically acceptable salt thereof to a subject having a need of treatment or prevention of premature ejaculation.

* * * * *